United States Patent
Ye et al.

(10) Patent No.: US 10,844,065 B2
(45) Date of Patent: Nov. 24, 2020

(54) HETEROCYCLIC COMPOUND, AND ORGANIC ELECTROLUMINESCENCE DEVICE AND ORGANIC ELECTROLUMINESCENCE DISPLAY DEVICE INCLUDING THE SAME

(71) Applicant: Samsung Display Co., Ltd., Yongin-si, Gyeonggi-do (KR)

(72) Inventors: Jimyoung Ye, Suwon-si (KR); Myeongsuk Kim, Hwaseong-si (KR); Seulong Kim, Hwaseong-si (KR); Byeongwook Yoo, Hwaseong-si (KR); Jaehoon Hwang, Seoul (KR); Soo-byung Ko, Yongin-si (KR); Jihwan Yoon, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 322 days.

(21) Appl. No.: 15/963,036

(22) Filed: Apr. 25, 2018

(65) Prior Publication Data

US 2019/0084986 A1 Mar. 21, 2019

(30) Foreign Application Priority Data

Sep. 21, 2017 (KR) .................. 10-2017-0122054

(51) Int. Cl.
*C07D 487/04* (2006.01)
*C07D 403/14* (2006.01)
(Continued)

(52) U.S. Cl.
CPC ......... *C07D 487/04* (2013.01); *C07D 403/14* (2013.01); *C07D 409/14* (2013.01);
(Continued)

(58) Field of Classification Search
CPC .................................................. H01L 51/0061
See application file for complete search history.

(56) References Cited

U.S. PATENT DOCUMENTS

| 8,283,052 B2 | 10/2012 | Egawa et al. |
| 2007/0132372 A1 | 6/2007 | Inoue et al. |

(Continued)

FOREIGN PATENT DOCUMENTS

| CN | 102140083 A | 8/2011 |
| CN | 106047337 A | 10/2016 |

(Continued)

OTHER PUBLICATIONS

English machine translation of Liu et al,, CN106831791A (Year: 2017).*

(Continued)

*Primary Examiner* — Peter F Godenschwager
(74) *Attorney, Agent, or Firm* — Lewis Roca Rothgerber Christie LLP

(57) ABSTRACT

Provided are a heterocyclic compound represented by Formula 1 and an organic electroluminescence device and an organic electroluminescence display device including the heterocyclic compound represented by Formula 1 in an emission layer. In Formula 1, A is represented by Formula 2, $D_1$ is represented by Formula 3, and $D_2$ is represented by Formula 4.

Formula 1

(Continued)

-continued

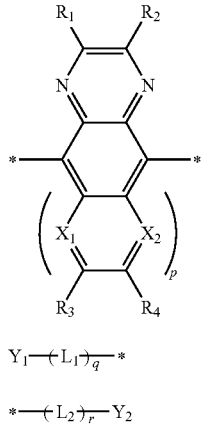

Formula 2

Y₁―(L₁)_q―*

Formula 3

*―(L₂)_r―Y₂

Formula 4

19 Claims, 7 Drawing Sheets

(51) Int. Cl.
- C07D 417/14 (2006.01)
- H01L 51/50 (2006.01)
- C07D 409/14 (2006.01)
- H01L 51/00 (2006.01)
- C07D 413/14 (2006.01)
- C07D 487/02 (2006.01)
- H01L 27/32 (2006.01)

(52) U.S. Cl.
CPC ......... *C07D 413/14* (2013.01); *C07D 417/14* (2013.01); *C07D 487/02* (2013.01); *H01L 51/0061* (2013.01); *H01L 51/0072* (2013.01); *H01L 51/5024* (2013.01); *H01L 27/3213* (2013.01); *H01L 51/0074* (2013.01); *H01L 51/5012* (2013.01)

(56) References Cited

U.S. PATENT DOCUMENTS

2009/0153030 A1* 6/2009 Huo .................. H01L 51/0061
313/504

2016/0133856 A1 5/2016 Yang et al.
2018/0282277 A1 10/2018 Cao et al.

FOREIGN PATENT DOCUMENTS

| CN | 106831791 A | * | 6/2017 |
| CN | 106967060 A | | 7/2017 |
| KR | 10-2008-0080099 | | 9/2008 |
| KR | 10-1426513 | | 7/2014 |
| KR | 10-2016-0056783 | | 5/2016 |
| KR | 10-1720079 | | 3/2017 |

OTHER PUBLICATIONS

Qin et al. "Multistimuli-Responsive Luminescence Switching of Pyrazine Derivative Based Donor—Acceptor—Donor Luminophores" Chem. Asian J. 2016, 11, 285-293. (Year: 2016).*
Hedstrom, Svante, et al., "Light-harvesting capabilities of low band gap donor-acceptor polymers", Phys. Chem. Chem. Phys., 2014, vol. 16, (13 pages).
Lee, Po-I, et al., "New Conjugated Copolymers Based on Benzo [1,2-b; 3,4-b'] dithiophene and Derivatives of Benzo[g]quinoxaline for Bulk Heterojunction Solar Cells", Journal of Polymer Science: Part A: Polymar Chemistry, 2011, vol. 49, (9 pages).
Schulz, Gisela, et al., "Synthesis and Photovoltaic Performance of Pyrazinoquinoxaline Containing Conjugated Thiophene-Based Dendrimers and Polymers", Macromolecules, 2013, vol. 46, (11 pages).
Tam, Teck Lip Dexter, et al., "From benzobisthiadiazole, thiadiazoloquinoxaline to pyrazinoquinoxaline based polymers: effects of aromatic substituents on the performance of organic photovoltaics", Journal of Materials Chemistry, 2012, vol. 22, (7 pages).
Tam, Teck Lip, et al., "Substituent effect on the electronic properties of pyrazino[2, 3-g] quinoxaline molecules", Journal of Materials Chemistry, 2011, vol. 21, (7 pages).
Wang, Ergang, et al., Small Band Gap Polymers Synthesized via a Modified Nitration of 4,7-Dibromo-2,1,3-benzothiadiazole, Organic Letters, 2010, vol. 12, No. 20, (4 pages).
Zhang, Fengling, et al., "High Photovoltage achieved in low band gap polymer solar cells by adjusting energy levels of a polymer with the LUMOs of fullerence derivatives" Journal of Materials Chemistry, 2008, vol. 18, (7 pages).
EPO Extended Search Report dated Mar. 18, 2019 for corresponding European Patent Application No. 18183515.8 (14 pages).
EPO Partial Search Report dated Nov. 14, 2018, for corresponding European Patent Application No. (10 pages).

* cited by examiner

HETEROCYCLIC COMPOUND, AND ORGANIC ELECTROLUMINESCENCE DEVICE AND ORGANIC ELECTROLUMINESCENCE DISPLAY DEVICE INCLUDING THE SAME

CROSS-REFERENCE TO RELATED APPLICATION

This application claims priority to and the benefit of Korean Patent Application No. 10-2017-0122054, filed on Sep. 21, 2017, the entire content of which is incorporated herein by reference.

BACKGROUND

The present disclosure herein relates to a heterocyclic compound, and an organic electroluminescence device and an organic electroluminescence display device including the same.

The development of an organic electroluminescence display as an image display is being actively conducted. The organic electroluminescence display is different from a liquid crystal display and is a so called self-luminescent display that displays an image via the recombination of holes and electrons injected from a first electrode and a second electrode in an emission layer and via light emission from a luminescent material including an organic compound in the emission layer.

As an organic electroluminescence device, an organic device including, for example, a first electrode, a hole transport layer disposed on the first electrode, an emission layer disposed on the hole transport layer, an electron transport layer disposed on the emission layer, and a second electrode disposed on the electron transport layer has been prepared. Holes are injected from the first electrode, and the injected holes move via the hole transport layer and are injected into the emission layer. Meanwhile, electrons are injected from the second electrode, and the injected electrons move via the electron transport layer and are injected into the emission layer. The holes and electrons injected into the emission layer recombine to produce excitons in the emission layer. The organic electroluminescence device emits light using light generated by the transition of the excitons to a ground state. In addition, an embodiment of the configuration of the organic electroluminescence device is not limited thereto, but various modifications may be possible.

SUMMARY

The present disclosure provides a heterocyclic compound, and an organic electroluminescence device and an organic electroluminescence display device including the same. For example, the present disclosure provides a heterocyclic compound used as a luminescent material emitting near-infrared rays, and an organic electroluminescence device and an organic electroluminescence display device including the same.

An embodiment of the present disclosure provides a heterocyclic compound represented by the following Formula 1:

$$D_1\text{-}A\text{-}D_2 \quad \text{Formula 1}$$

In Formula 1, A is represented by the following Formula 2, $D_1$ is represented by the following Formula 3, and $D_2$ is represented by the following Formula 4:

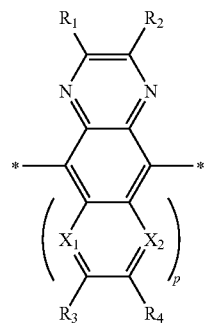

Formula 2

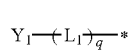

Formula 3

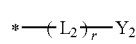

Formula 4

In Formulae 2 to 4, "q" and "r" are each independently an integer of 0 to 3, "p" is 0 or 1, $X_1$ and $X_2$ are each independently CR' or N, R' and $R_1$ to $R_4$ are each independently a hydrogen atom, a deuterium atom, a substituted or unsubstituted alkyl group having 1 to 10 carbon atoms, or a substituted or unsubstituted aryl group having 6 to 30 carbon atoms for forming a ring, $L_1$ and $L_2$ are each independently a substituted or unsubstituted arylene group having 6 to 30 carbon atoms for forming a ring, or a substituted or unsubstituted heteroarylene group having 2 to 30 carbon atoms for forming a ring, $Y_1$ and $Y_2$ are each independently a substituted or unsubstituted arylamine group, a substituted or unsubstituted aryl group having 6 to 30 carbon atoms for forming a ring, or a substituted or unsubstituted heteroaryl group having 2 to 30 carbon atoms for forming a ring, and at least one of $Y_1$ or $Y_2$ is an electron-donating group, in case "p" is 0, $Y_1$ and $Y_2$ are each independently represented by the following Formula 5:

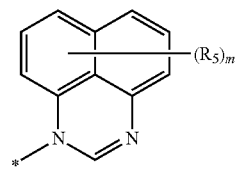

Formula 5

In Formula 5, $R_5$ is a hydrogen atom, a deuterium atom, a substituted or unsubstituted alkyl group having 1 to 10 carbon atoms, or a substituted or unsubstituted aryl group having 6 to 30 carbon atoms for forming a ring, and "m" is an integer of 0 to 6.

In an embodiment, "p" may be 1, and $X_1$ and $X_2$ may be N.

In an embodiment, at least one of $Y_1$ or $Y_2$ may be represented by one of the above Formula 5, the following Formula 6 or the following Formula 7:

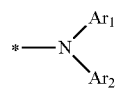

Formula 6

-continued

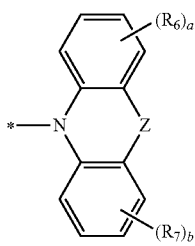

Formula 7

In Formula 6, $Ar_1$ and $Ar_2$ are each independently a substituted or unsubstituted aryl group having 6 to 30 carbon atoms for forming a ring.

In Formula 7, Z is a direct linkage, O, S, or $NR_8$, $R_6$ to $R_8$ are each independently a hydrogen atom, a deuterium atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, and "a" and "b" are each independently an integer of 0 to 4.

In an embodiment, at least one chosen from $R_1$ to $R_4$ may be a substituted or unsubstituted alkyl group having 1 to 10 carbon atoms, or a substituted or unsubstituted aryl group having 6 to 30 carbon atoms for forming a ring.

In an embodiment, at least one chosen from $R_1$ to $R_4$ may be a substituted or unsubstituted methyl group or a substituted or unsubstituted phenyl group.

In an embodiment, $D_1$ and $D_2$ may be symmetric about A. In this case, $X_1$ and $X_2$ may be the same.

In an embodiment, $L_1$ and $L_2$ may be each independently represented by one of the following Formulae 8-1 to 8-4:

Formula 8-1

Formula 8-2

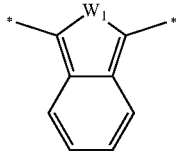

Formula 8-3

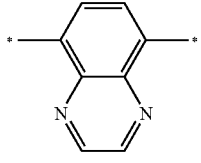

Formula 8-4

In Formulae 8-2 and 8-3, $W_1$ and $W_2$ are each independently $NR_9$, S, or O, and $R_9$ is a hydrogen atom, a deuterium atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring.

In an embodiment, $Y_1$ and $Y_2$ may be different from each other.

In an embodiment, the heterocyclic compound according to an embodiment of the present disclosure may emit near-infrared rays in a wavelength region of about 750 nm to about 1,000 nm.

In an embodiment of the present disclosure, an organic electroluminescence device includes a first electrode, a hole transport region provided on the first electrode, an emission layer provided on the hole transport region, an electron transport region provided on the emission layer, and a second electrode provided on the electron transport region, wherein the emission layer includes the heterocyclic compound according to an embodiment of the present disclosure.

In an embodiment, the emission layer may include a host and a dopant and may emit near-infrared rays in a wavelength region of about 750 nm to about 1,000 nm, and the dopant may include the heterocyclic compound according to an embodiment of the present disclosure.

In an embodiment of the present disclosure, an organic electroluminescence display device includes a first pixel including a first organic light emitting diode which emits first visible rays, a second pixel including a second organic light emitting diode which emits second visible rays, a third pixel including a third organic light emitting diode which emits third visible rays, and a fourth pixel including a fourth organic light emitting diode which emits near-infrared rays, wherein the fourth organic light emitting diode includes the heterocyclic compound according to an embodiment of the present disclosure.

BRIEF DESCRIPTION OF THE FIGURES

The accompanying drawings are included to provide a further understanding of the subject matter of the present disclosure, and are incorporated in and constitute a part of this specification. The drawings illustrate exemplary embodiments of the present disclosure and, together with the description, serve to explain principles of the subject matter of the present disclosure. In the drawings.

DETAILED DESCRIPTION

Figure 1:
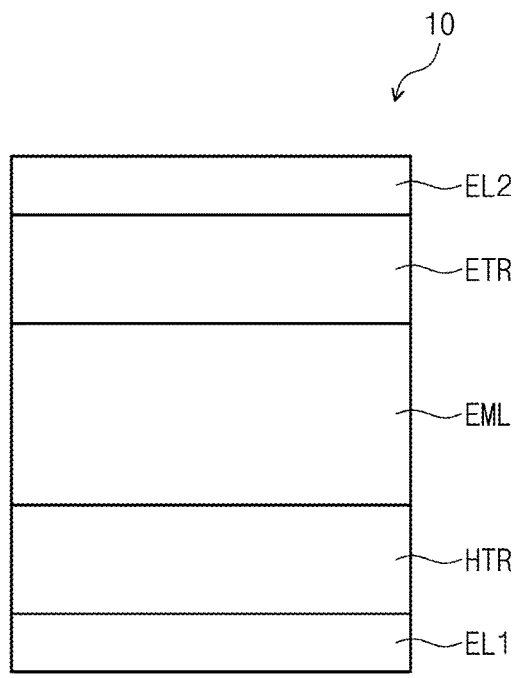
FIG. 1 is a cross-sectional view schematically illustrating an organic electroluminescence device according to an embodiment of the present disclosure.

The above objects, other objects, features and/or advantages of the present disclosure will be readily understood from exemplary embodiments with reference to the accompanying drawings. The present disclosure may, however, be embodied in different forms and should not be construed as limited to the embodiments set forth herein.

Like reference numerals refer to like elements for explaining each drawing. In the drawings, the sizes of elements may be enlarged for clarity of the present disclosure. It will be understood that, although the terms first, second, etc. may be used herein to describe various elements, these elements should not be limited by these terms. These terms are only used to distinguish one element from another element. For example, a first element discussed below could be termed a second element, and similarly, a second element could be termed a first element. As used herein, the singular forms are intended to include the plural forms as well, unless the context clearly indicates otherwise.

It will be further understood that the terms "comprises" or "comprising," when used in this specification, specify the presence of stated features, numerals, steps, operations, elements, parts, or a combination thereof, but do not preclude the presence or addition of one or more other features, numerals, steps, operations, elements, parts, or a combination thereof. It will also be understood that when a layer, a film, a region, a plate, etc. is referred to as being "on" another part, it can be "directly on" the other part, or intervening layers may also be present. On the contrary, when a layer, a film, a region, a plate, etc. is referred to as being "under" another part, it can be "directly under" the other part, or intervening layers may also be present.

In the present disclosure, —* means a part to be coupled or connected.

In the present disclosure, "substituted or unsubstituted" may mean substituted with at least one substituent selected from the group consisting of a deuterium atom, a halogen atom, a cyano group, a nitro group, an amino group, a silyl group, a boron group, a phosphine oxide group, a phosphine sulfide group, an alkyl group, an alkenyl group, an aryl group, and a heterocycle, or unsubstituted. In addition, each of the substituent illustrated above may be substituted or unsubstituted. For example, a biphenyl group may be interpreted as an aryl group, or a phenyl group substituted with a phenyl group.

In the present disclosure, a hydrocarbon ring may include an aliphatic hydrocarbon ring and an aromatic hydrocarbon ring (aryl group). A heterocycle includes an aliphatic heterocycle and an aromatic heterocycle (heteroaryl group). The hydrocarbon ring and the heterocycle may be a monocycle or polycycle.

In the present disclosure, a halogen atom may include a fluorine atom, a chlorine atom, a bromine atom, or an iodine atom.

In the present disclosure, alkyl group may have a linear or branched chain or a cycle shape. The carbon number of the alkyl group may be 1 to 30, 1 to 20, 1 to 10, or 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyl eicosyl, 2-butyl eicosyl, 2-hexyl eicosyl, 2-octyl eicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the present disclosure, alkenyl group may be linear or branched. The carbon number of the alkenyl group is not specifically limited, and may be 2 to 30, 2 to 20, or 2 to 10. Examples of the alkenyl group may include vinyl, 1-butenyl, 1-pentenyl, 1,3-butadienyl aryl, styrenyl, styrylvinyl, etc., without limitation.

In the present disclosure, aryl group means an optional functional group or substituent derived from an aromatic hydrocarbon ring. The aryl group may be monocyclic aryl group or polycyclic aryl group. The carbon number of the aryl group for forming a ring may be 6 to 60, 6 to 30, 6 to 20, or 6 to 15. Examples of the aryl group may include phenyl, naphthyl, fluorenyl, anthracenyl, phenanthryl, biphenyl, terphenyl, quaterphenyl, quinqphenyl, sexiphenyl, biphenylene, triphenylene, pyrenyl, benzofluoranthenyl, chrysenyl, etc., without limitation.

In the present disclosure, fluorenyl may be substituted, or two substituents may be combined with each other to form a spiro structure. Examples of the substituted fluorenyl are as follows. However, an embodiment of the present disclosure is not limited thereto.

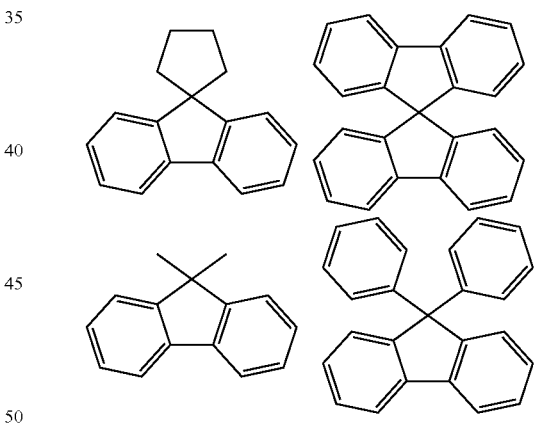

In the present disclosure, heteroaryl group may be heteroaryl including at least one of O, N, P, Si or S as a heteroatom. When the heteroaryl group includes two heteroatoms, two heteroatoms may be the same or different from each other. The carbon number of the heteroaryl group for forming a ring may be 2 to 60, 2 to 30, or 2 to 20. The heteroaryl group may be monocyclic heteroaryl group or polycyclic heteroaryl group. The polycyclic heteroaryl group may have a structure of, for example, two rings or three rings. Examples of the heteroaryl group may include thiophene, furan, pyrrole, imidazole, thiazole, oxazole, oxadiazole, triazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroaryl carbazole, N-alkyl carbazole, benzoxazole, benzoimidazole, benzothiazole, benzocarbazole, benzothiophene, dibenzothiophene, thienothiophene, benzofuran, phenanthroline, thiazole, isooxazole, oxadiazole, thiadiazole, phenothiazine, dibenzosilole, dibenzofuran, etc., without limitation.

In the present disclosure, the explanation on aryl group may be applied to an arylene group except that the arylene group is divalent.

In the present disclosure, the explanation on heteroaryl group may be applied to a heteroarylene group except that the heteroarylene group is divalent.

In the present disclosure, silyl group may include alkylsilyl group and arylsilyl group. Examples of the silyl group may include trimethylsilyl, triethylsilyl, t-butyldimethylsilyl, vinyldimethylsilyl, propyldimethylsilyl, triphenylsilyl, diphenylsilyl, phenylsilyl, etc., without limitation.

In the present disclosure, a boron group may include alkyl boron group and aryl boron group. Examples of the boron group may include trimethylboron, triethylboron, t-butyldimethyl boron, triphenylboron, diphenylboron, phenylboron, etc., without limitation.

In the present disclosure, the carbon number of an amino group is not specifically limited, but may be 1 to 30. The amino group may include an alkylamino group and an arylamino group. Examples of the amino group may include a methylamino group, a dimethylamino group, a phenylamino group, a diphenylamino group, a naphthylamino group, a 9-methyl-anthracenylamino group, a triphenylamino group, etc., without limitation.

In the present disclosure, a phosphine oxide group may be substituted with, for example, at least one of an alkyl group or an aryl group. Examples of the phosphine oxide group include a phenyl phosphine oxide group, a diphenyl phosphine oxide group, etc., without limitation.

In the present disclosure, a direct linkage may include a single bond.

First, the heterocyclic compound according to an embodiment of the present disclosure will be explained.

The heterocyclic compound according to an embodiment of the present disclosure is represented by Formula 1 below.

$$D_1\text{-}A\text{-}D_2 \qquad \text{Formula 1}$$

In Formula 1, A is represented by Formula 2 below, $D_1$ is represented by Formula 3 below, and $D_2$ is represented by Formula 4 below.

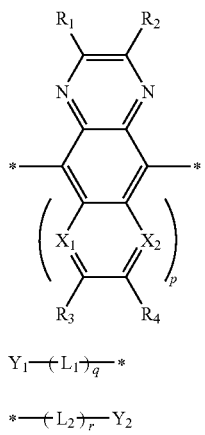

In Formula 2, "p" is 0 or 1, $X_1$ and $X_2$ are each independently CR' or N, R' and $R_1$ to $R_4$ are each independently a hydrogen atom, a deuterium atom, a substituted alkyl group having 1 to 10 carbon atoms, or a substituted or unsubstituted aryl group having 6 to 30 carbon atoms for forming a ring.

In Formula 2, if "p" is 0, a structure represented by Formula 2 has a bicyclic structure. Meanwhile, in Formula 2, if "p" is 1, a structure represented by Formula 2 has a tricyclic structure.

In Formula 3, "q" is an integer of 0 to 3, $L_1$ is a substituted or unsubstituted arylene group having 6 to 30 carbon atoms for forming a ring, or a substituted or unsubstituted heteroarylene group having 2 to 30 carbon atoms for forming a ring, and $Y_1$ is a substituted or unsubstituted aryl group having 6 to 30 carbon atoms for forming a ring, or a substituted or unsubstituted heteroaryl group having 2 to 30 carbon atoms for forming a ring.

In Formula 3, if "q" is 2 or more, a plurality of $L_1$ groups are the same or different.

In Formula 4, "r" is an integer of 0 to 3, $L_2$ is a substituted or unsubstituted arylene group having 6 to 30 carbon atoms for forming a ring, or a substituted or unsubstituted heteroarylene group having 2 to 30 carbon atoms for forming a ring, and $Y_2$ is a substituted or unsubstituted aryl group having 6 to 30 carbon atoms for forming a ring, or a substituted or unsubstituted heteroaryl group having 2 to 30 carbon atoms for forming a ring.

In Formula 4, if "r" is 2 or more, a plurality of $L_2$ groups are the same or different.

At least one of $Y_1$ or $Y_2$ is an electron-donating group. For example, at least one of $Y_1$ or $Y_2$ is a functional group including a nitrogen atom.

If "p" is 0, $Y_1$ and $Y_2$ are each independently represented by the following Formula 5:

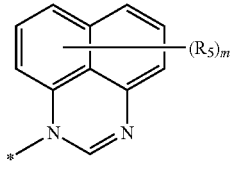

In Formula 5, $R_5$ is a hydrogen atom, a deuterium atom, a substituted or unsubstituted alkyl group having 1 to 10 carbon atoms, or a substituted or unsubstituted aryl group having 6 to 30 carbon atoms for forming a ring, and "m" is an integer of 0 to 6.

In Formula 5, "m" may be 0. However, an embodiment of the present disclosure is not limited thereto. "m" may be 1, and $R_5$ may be substituted with a substituent other than a hydrogen atom or a deuterium atom.

In Formula 5, if "m" is 2 or more, a plurality of $R_5$ groups are the same or different.

In Formula 1, A is an electron accepting moiety (electron acceptor), and at least one of $D_1$ or $D_2$ is an electron providing moiety (electron donor).

"p" may be 1, without limitation. If applied to an organic electroluminescence device and an organic electroluminescence display device, it is favorable in consideration of stability and efficiency when compared to a case "p" is 0.

$X_1$ and $X_2$ may be the same. For example, "p" may be 1, and $X_1$ and $X_2$ may be N. For example, "p" may be 1, and $X_1$ and $X_2$ may be C.

At least one of $Y_1$ or $Y_2$ may be represented by one of the above Formula 5, the following Formula 6 or the following Formula 7:

Formula 6

Formula 7

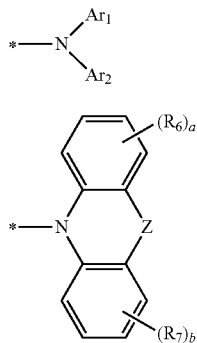

In Formula 6, $Ar_1$ and $Ar_2$ are each independently a substituted or unsubstituted aryl group having 6 to 30 carbon atoms for forming a ring.

In Formula 7, Z is a direct linkage, O, S, or $NR_8$, $R_6$ to $R_8$ are each independently a hydrogen atom, a deuterium atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, and "a" and "b" are each independently an integer of 0 to 4.

If "a" is 2 or more, a plurality of $R_6$ groups are the same or different. If "b" is 2 or more, a plurality of $R_7$ groups are the same or different.

In Formula 6, $Ar_1$ and $Ar_2$ are each independently a substituted or unsubstituted phenyl group, a substituted or unsubstituted biphenyl group, or a substituted or unsubstituted naphthyl group. However, an embodiment of the present disclosure is not limited thereto.

In Formula 7, if Z is a direct linkage, a structure represented by Formula 7 is a carbazole moiety.

In Formula 7, each of "a" and "b" may be 0. However, an embodiment of the present disclosure is not limited thereto. a+b may be 1 or more, and at least one of $R_6$ or $R_7$ may be a substituted or unsubstituted heteroaryl group. For example, a+b may be 1 or more, and at least one of $R_6$ or $R_7$ may be a substituted or unsubstituted carbazole group.

In Formula 7, Z may be O, S, or $NR_8$. If Z is $NR_8$, $R_8$ may be a substituted or unsubstituted aryl group having 6 to 30 carbon atoms for forming a ring. For example, $R_8$ may be a substituted or unsubstituted phenyl group. Z may be O. Z may be S.

At least one of $Y_1$ or $Y_2$ may be represented by one of the following structures:

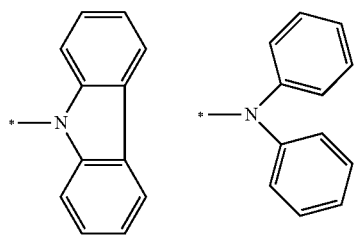

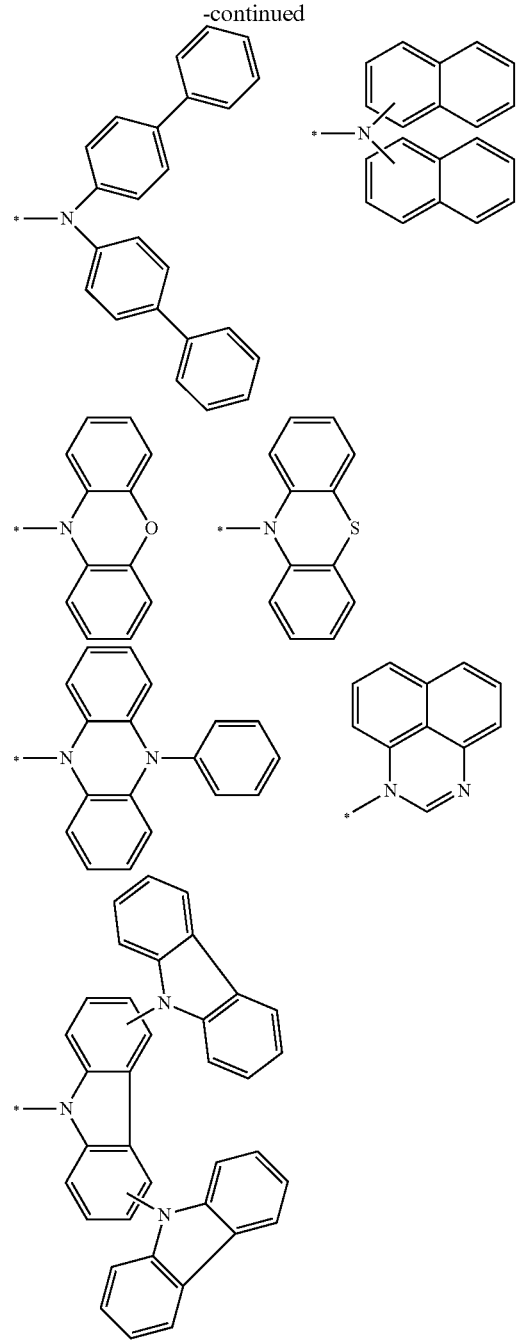

Each of the structures may be substituted or unsubstituted.

In Formula 2, at least one chosen from $R_1$ to $R_4$ may be a substituted or unsubstituted alkyl group having 1 to 10 carbon atoms, or a substituted or unsubstituted aryl group having 6 to 30 carbon atoms for forming a ring. In this case, it is favorable in terms of thermal stability. For example, if $R_1$ is a hydrogen atom, thermal decomposition may occur during a deposition process, and protons may be generated and may become the cause of deterioration. Accordingly, the securing of the thermal stability is favorable if $R_1$ is substituted with a substituent other than a hydrogen atom. For example, at least one chosen from $R_1$ to $R_4$ may be a substituted or unsubstituted methyl group or a substituted or unsubstituted phenyl group. For example, all $R_1$ to $R_4$ may be substituted or unsubstituted methyl groups. For example, all $R_1$ to $R_4$ may be substituted or unsubstituted phenyl groups, and in this case, effects of favorable solubility may be achieved.

However, an embodiment of the present disclosure is not limited thereto. $R_1$ to $R_4$ may be each independently a hydrogen atom or a deuterium atom, if needed.

R' may be, for example, a hydrogen atom. However, an embodiment of the present disclosure is not limited thereto.

The heterocyclic compound according to an embodiment of the present disclosure may have a structure in which $D_1$ and $D_2$ are symmetric about a core structure represented by A. In this case, both $Y_1$ and $Y_2$ are electron donors, and the heterocyclic compound according to an embodiment of the present disclosure becomes to have an "electron donor-electron acceptor-electron donor" structure. If the compound has a structure in which $D_1$ and $D_2$ are symmetric about A, electrons are widely spread in a molecule, molecules are stabilized, and overlapping in a certain part of an orbital of the highest occupied molecular orbital (HOMO) level and an orbital of the lowest unoccupied molecular orbital (LUMO) level arises, thereby increasing photoluminescence quantum yield (PLQY) and achieving favorable efficiency.

If required, the heterocyclic compound according to an embodiment of the present disclosure may have an "electron donor-electron acceptor" structure. In this case, $Y_1$ and $Y_2$ are different. For example, one of $Y_1$ or $Y_2$ may be an electron donor, and the remaining one may be a substituted or unsubstituted aryl group having 6 to 30 carbon atoms for forming a ring. For example, one of $Y_1$ or $Y_2$ is represented by Formula 6 or 7, and the remaining one may be a substituted or unsubstituted phenyl group. With the "electron donor-electron acceptor" structure, a wavelength may be favorably lengthened.

$L_1$ and $L_2$ may be each independently represented by one of the following Formulae 8-1 to 8-4, without limitation:

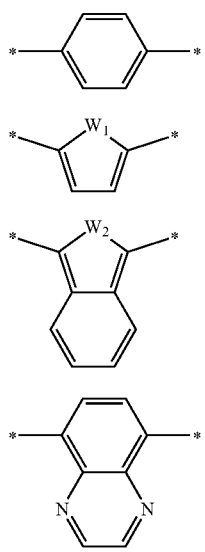

Formula 8-1

Formula 8-2

Formula 8-3

Formula 8-4

In Formula 8-2, $W_1$ is $NR_9$, S, or O, $R_9$ is a hydrogen atom, a deuterium atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring. $R_9$ may be, for example, a hydrogen atom, or a substituted or unsubstituted phenyl group.

In Formula 8-3, $W_2$ is $NR_9$, S, or O, $R_9$ is a hydrogen atom, a deuterium atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring. $R_9$ may be, for example, a hydrogen atom, or a substituted or unsubstituted phenyl group.

Each of the structures represented by Formulae 8-1 to 8-4 may be substituted or unsubstituted.

"q" and "r" may be 0. In this case, $Y_1$ and $Y_2$ are directly bonded (for example, single bond) to a core structure represented by Formula 2.

Each of "q" and "r" may be 1 or more. In this case, $Y_1$ and $Y_2$ are bonded to a core structure represented by Formula 2 via linkers represented by $L_1$ and $L_2$, respectively. In this case, a conjugation system is increased, and lengthening of a wavelength is favorable. In addition, if a linker is included, photoluminescence quantum yield (PLQY) is increased, thereby achieving favorable efficiency.

If "q" is 2 or more, a plurality of $L_1$ groups may be each independently represented by one of Formulae 8-1 to 8-4. For example, if "q" is 2, one of $L_1$ may be represented by Formula 8-1, and the remaining $L_1$ may be represented by Formula 8-2.

If "r" is 2 or more, a plurality of $L_2$ groups may be each independently represented by one of Formulae 8-1 to 8-4. For example, if "r" is 2, one of $L_2$ may be represented by Formula 8-1, and the remaining $L_2$ may be represented by Formula 8-3. For example, if "r" is 3, two of $L_2$ may be represented by Formula 8-2, and the remaining $L_2$ may be represented by Formula 8-4.

The heterocyclic compound according to an embodiment of the present disclosure may be used as a material for an organic electroluminescence device, for example, a luminescent material of near-infrared rays. For example, the heterocyclic compound according to an embodiment of the present disclosure may be a luminescent material emitting near-infrared rays in a wavelength region of about 750 nm to about 1,000 nm.

The heterocyclic compound represented by Formula 1 according to an embodiment of the present disclosure may be any one selected from the compounds represented in the following Compound Group 1. However, an embodiment of the present disclosure is not limited thereto.

Compound Group 1
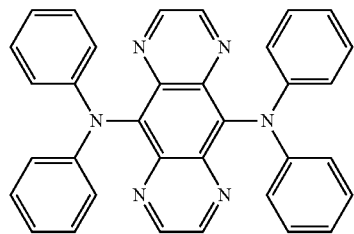
1
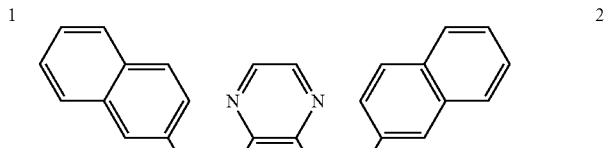
2
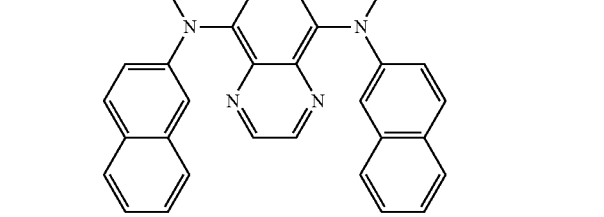
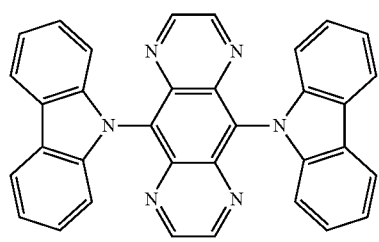
3
4
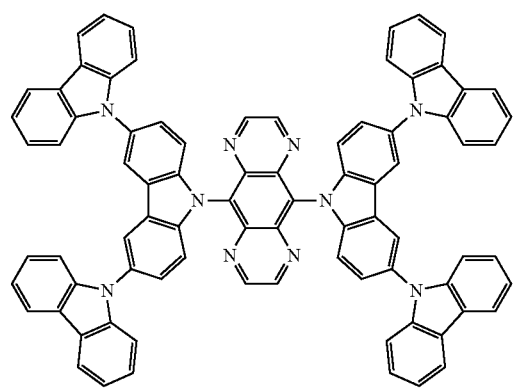
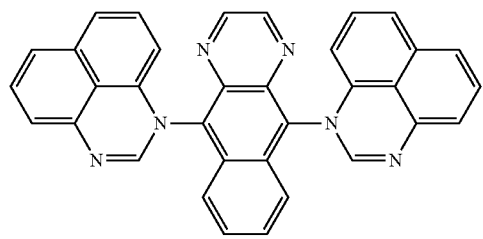
5
6
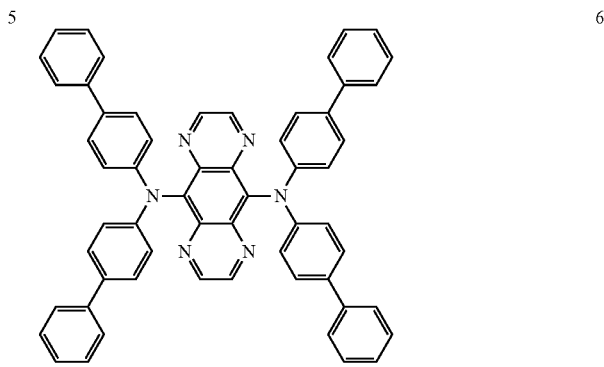
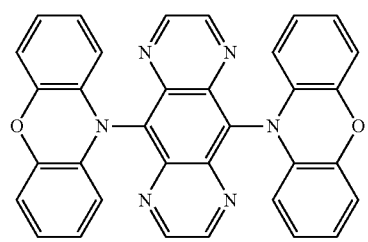
7
8
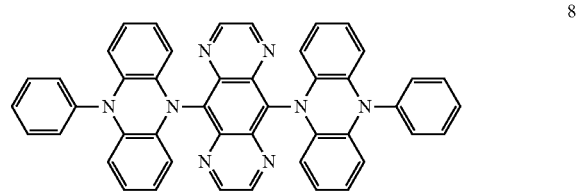
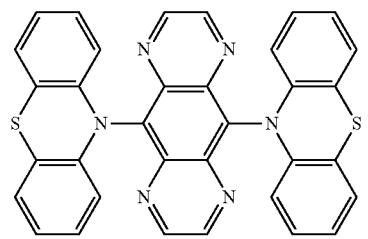
9
10
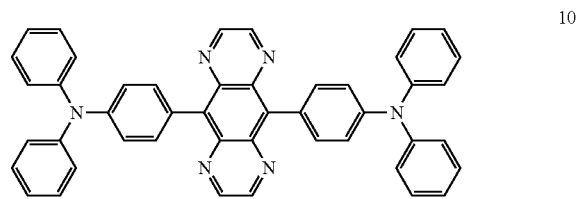

-continued
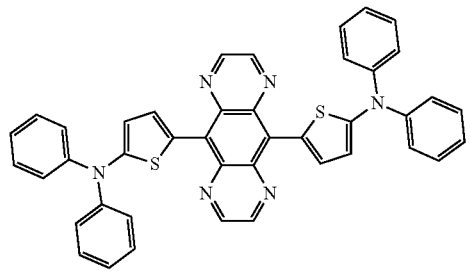
11
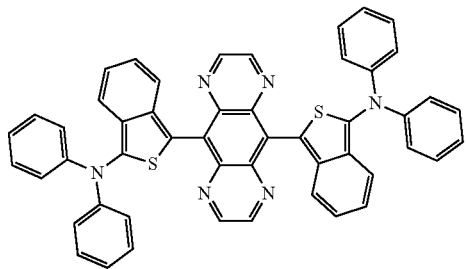
12
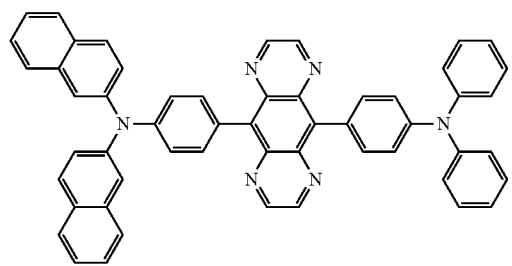
13
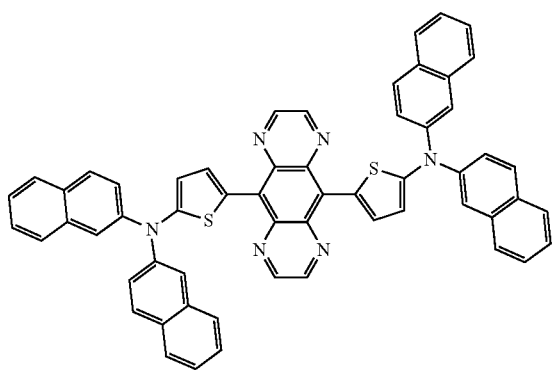
14
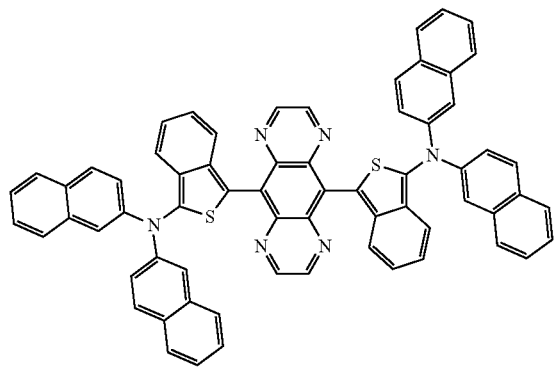
15
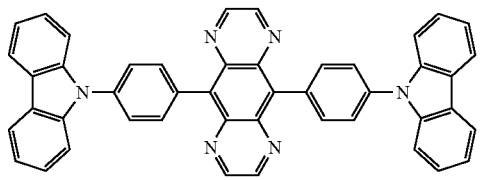
16
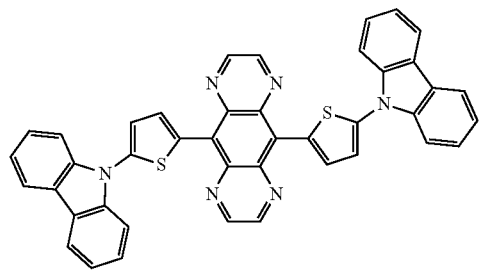
17
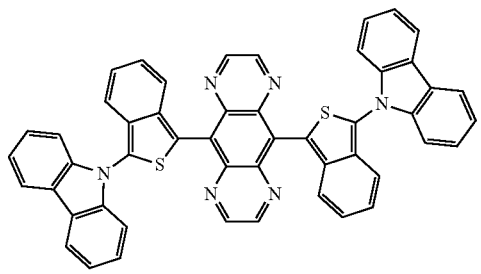
18

19
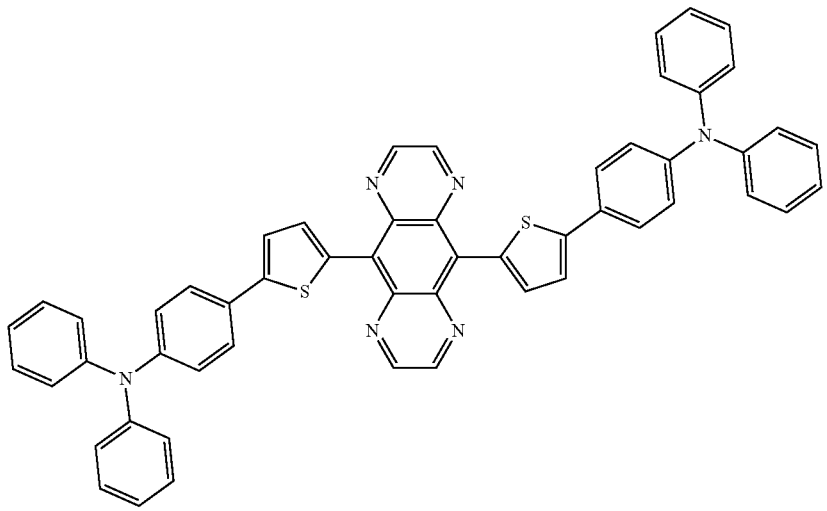
20
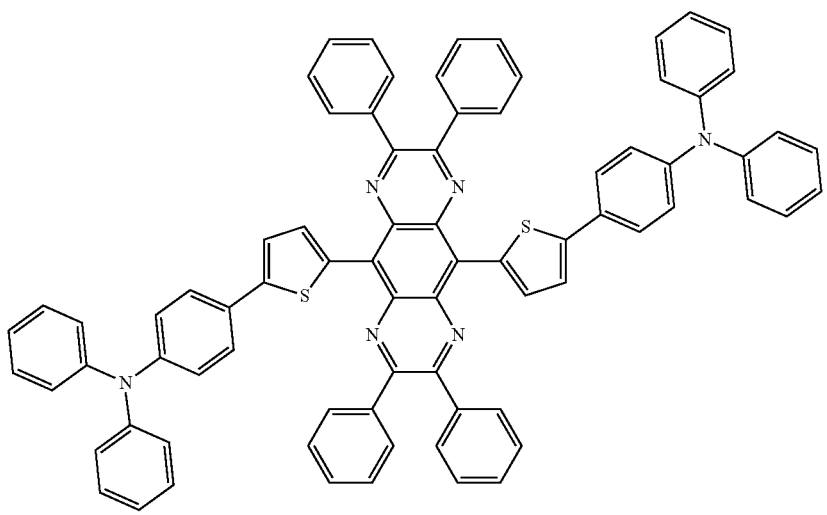
21
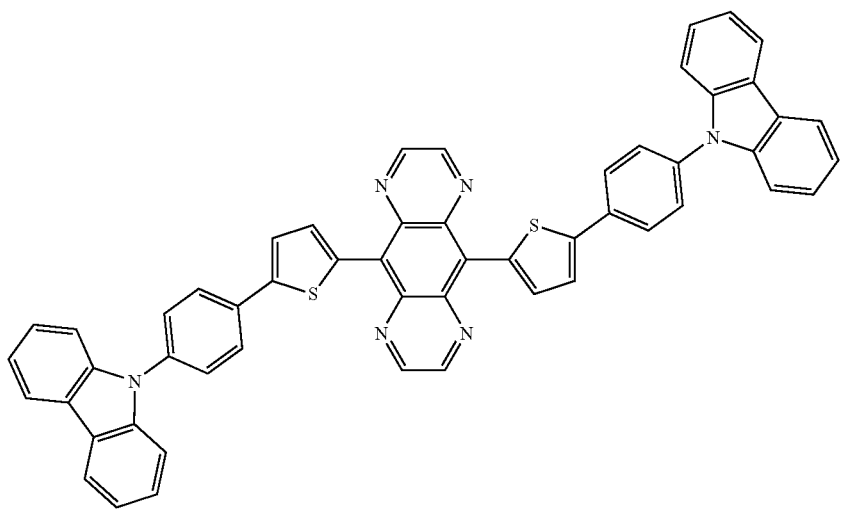

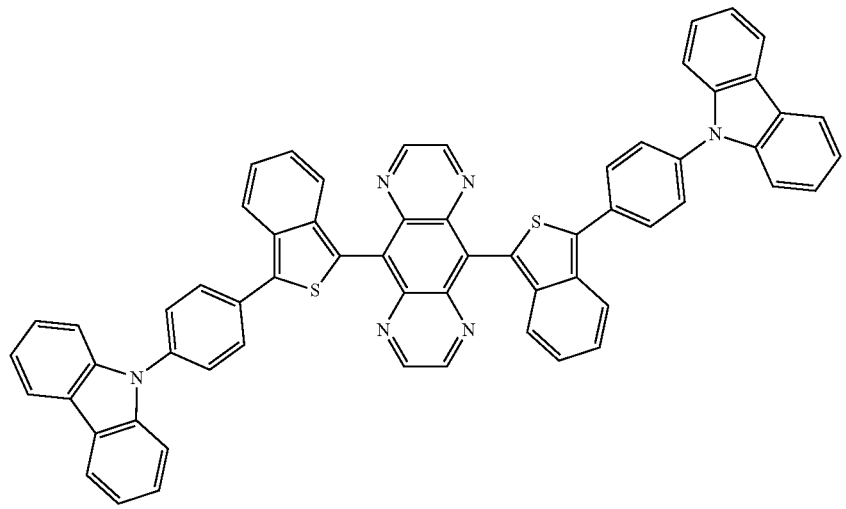
22
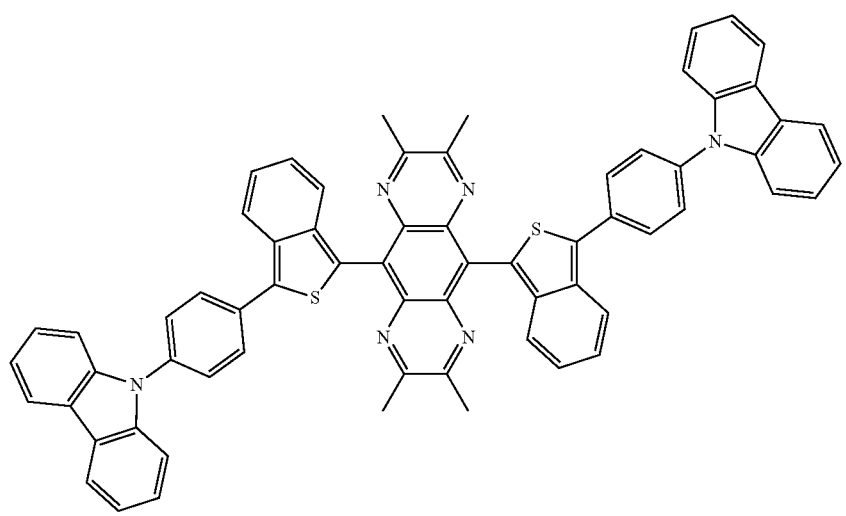
23
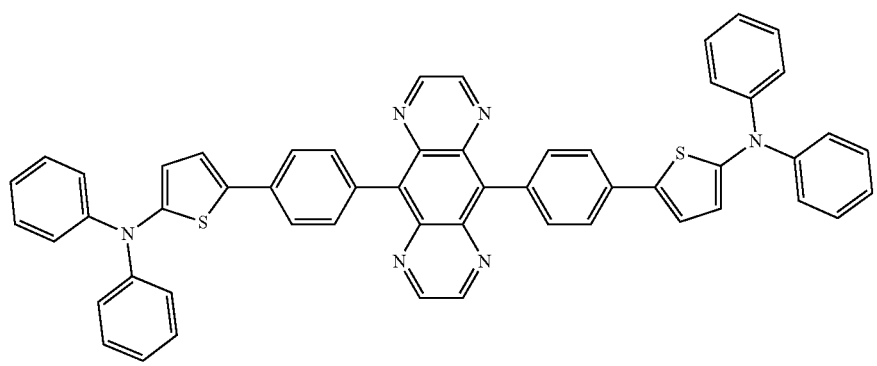
24

25
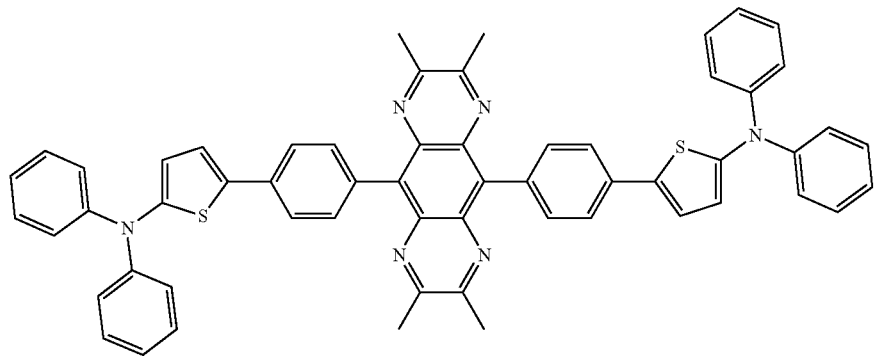
26
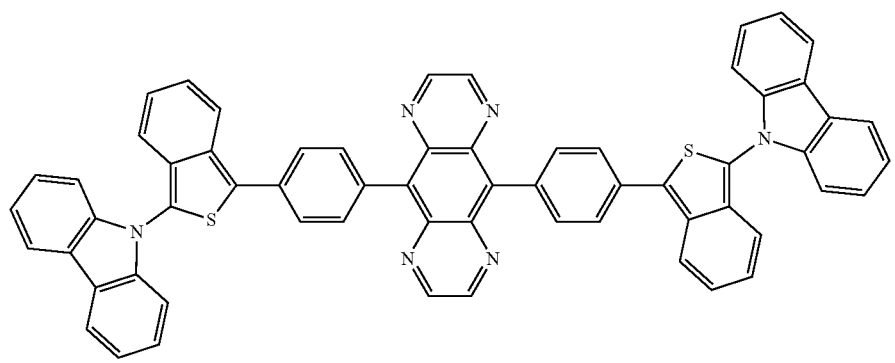
27
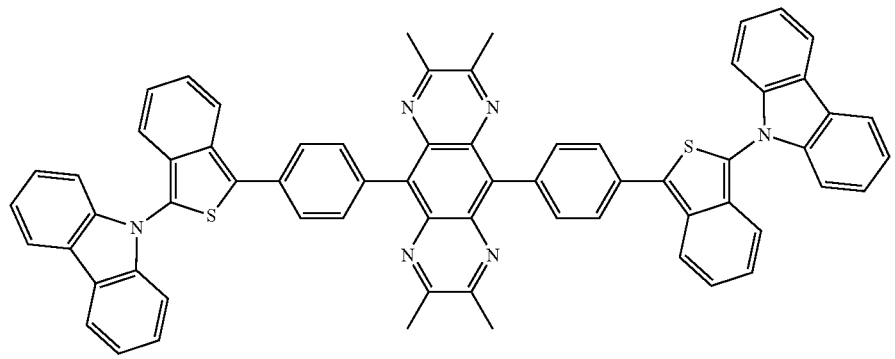
28
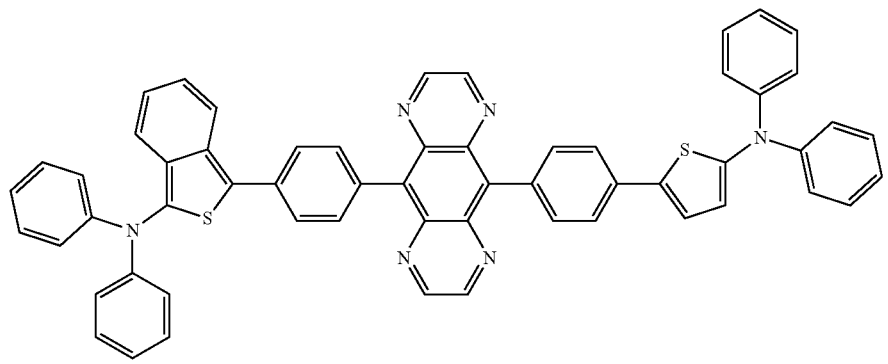

-continued
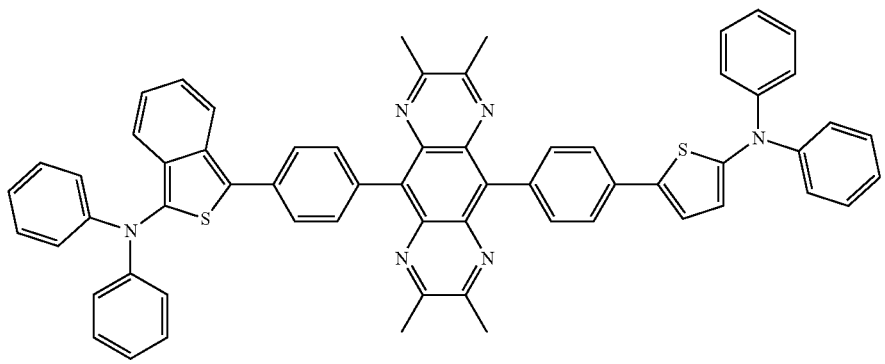
29
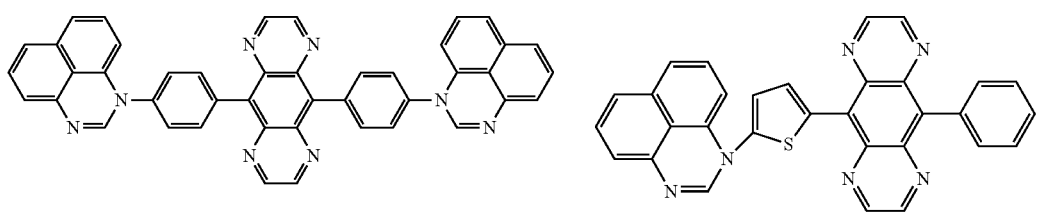
30  31
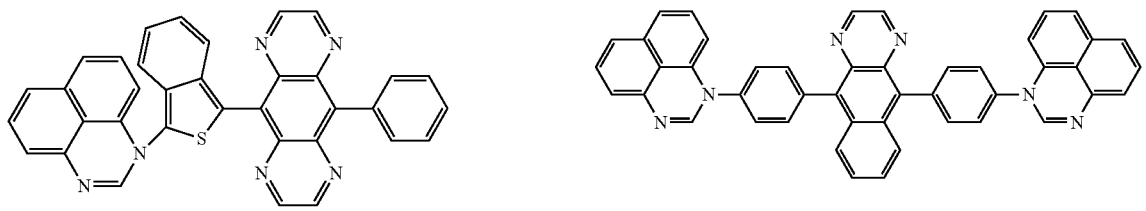
32  33
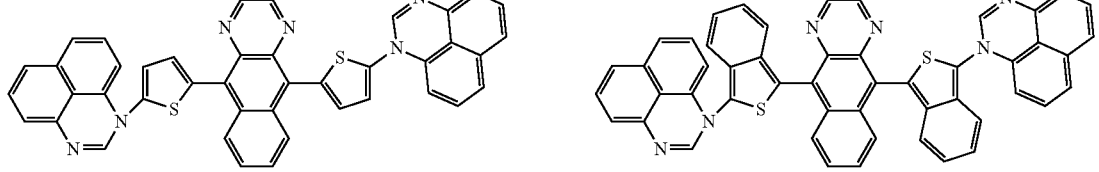
34  35
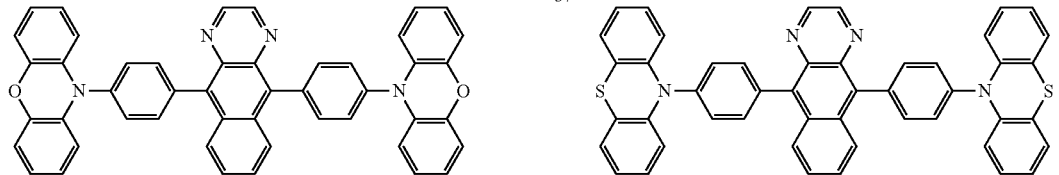
36
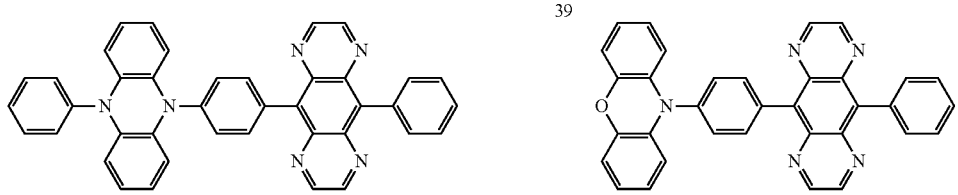
37  38
39  40

-continued
41
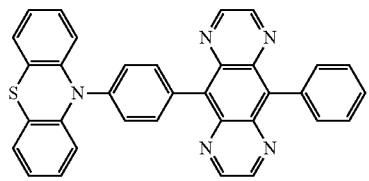
42
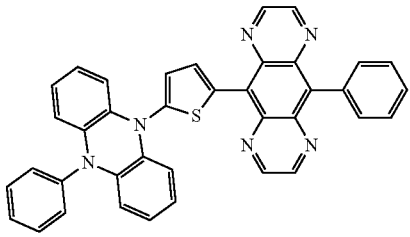
43
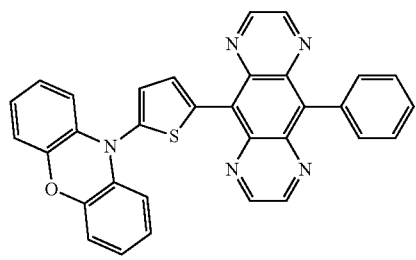
44
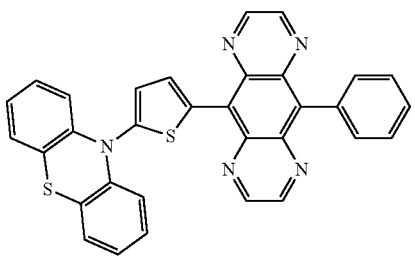
45
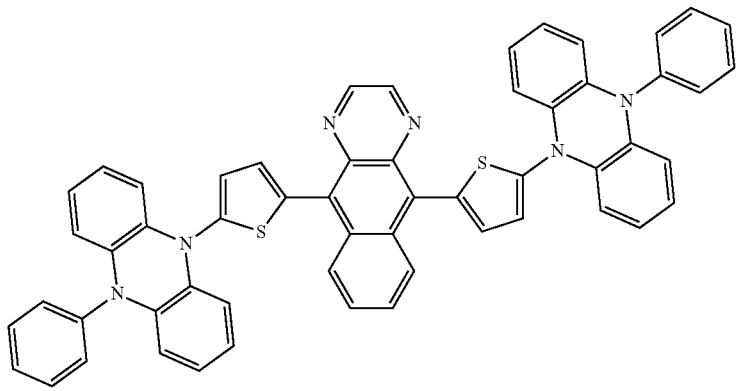
46
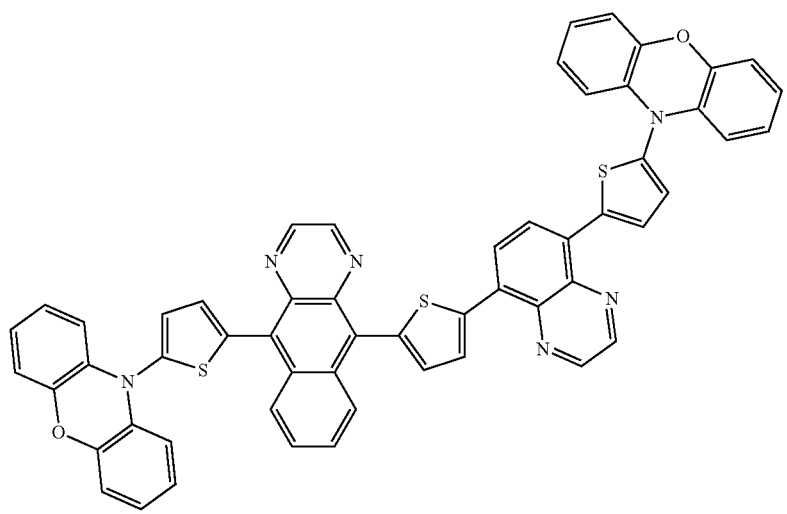

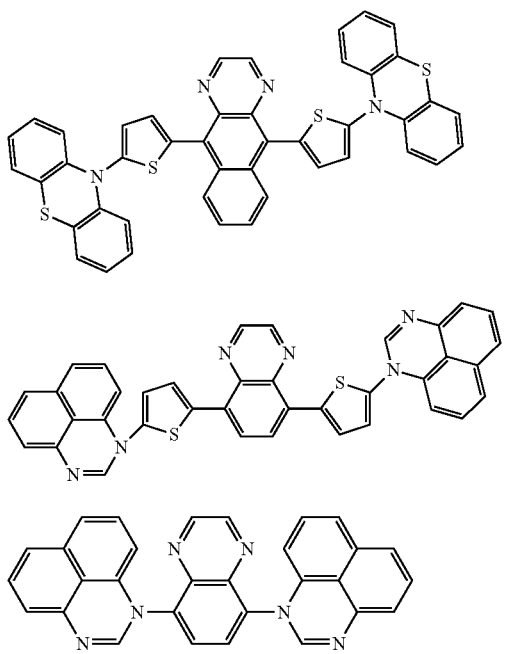

The heterocyclic compound according to an embodiment of the present disclosure may be used as a luminescent material of an organic electroluminescence device and an organic electroluminescence display device, and for example, as a luminescent material of near-infrared rays. The organic electroluminescence device and the organic electroluminescence display device including the heterocyclic compound according to an embodiment of the present disclosure may favorably accomplish high efficiency.

The heterocyclic compound represented by Formula 1 may be prepared based on the synthetic examples described later. However, the synthetic process of the heterocyclic compound represented by Formula 1 is not limited to the synthetic examples described later, and any suitable reaction conditions used in the art may be applied.

Hereinafter, an organic electroluminescence device according to an embodiment of the present disclosure will be explained. The explanation will be mainly with the different features from the explanation of the heterocyclic compound according to an embodiment of the present disclosure, and unexplained part will follow the above-description on the heterocyclic compound according to an embodiment of the present disclosure.

The organic electroluminescence device according to an embodiment of the present disclosure includes the above-described heterocyclic compound according to an embodiment of the present disclosure.

Figure 2:
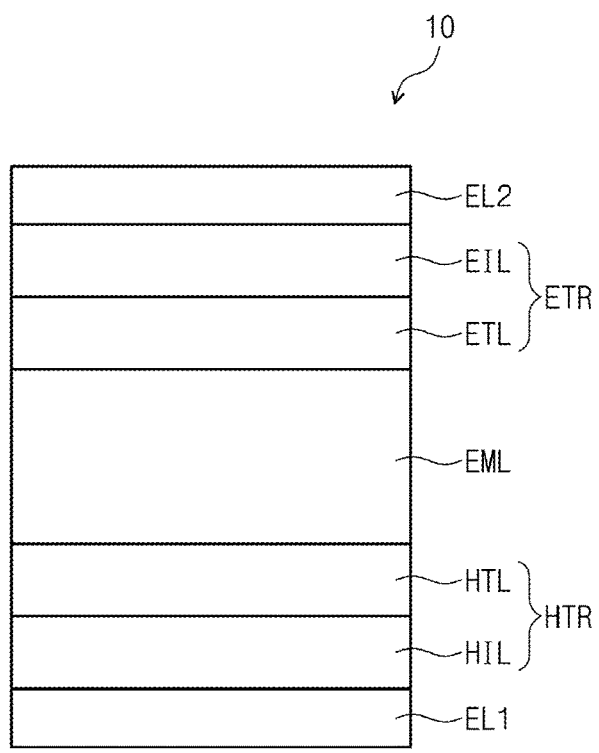
FIG. 2 is a cross-sectional view schematically illustrating an organic electroluminescence device according to an embodiment of the present disclosure.

FIG. 1 is a cross-sectional view schematically illustrating an organic electroluminescence device according to an embodiment of the present disclosure. FIG. 2 is a cross-sectional view schematically illustrating an organic electroluminescence device according to an embodiment of the present disclosure.

Referring to FIGS. 1-2, an organic electroluminescence device 10 according to an embodiment of the present disclosure may include a first electrode EL1, a hole transport region HTR, an emission layer EML, an electron transport region ETR, and a second electrode EL2.

The first electrode EL1 and the second electrode EL2 are oppositely disposed, and between the first electrode EL1 and the second electrode EL2, a plurality of organic layers may be disposed. The plurality of the organic layers may include a hole transport region HTR, an emission layer EML and an electron transport region ETR.

The organic electroluminescence device 10 according to an embodiment of the present disclosure may include the heterocyclic compound according to an embodiment of the present disclosure in at least one organic layer among the plurality of the organic layers disposed between the first electrode EL1 and the second electrode EL2.

Hereinafter, a case of including the heterocyclic compound according to an embodiment of the present disclosure in an emission layer EML will be explained as an embodiment. However, an embodiment of the present disclosure is not limited thereto. For example, a hole transport region HTR may include the heterocyclic compound according to an embodiment of the present disclosure.

The first electrode EL1 has conductivity. The first electrode EL1 may be a pixel electrode or an anode. The first electrode EL1 may be a transmissive electrode, a transflective electrode, or a reflective electrode. If the first electrode EL1 is the transmissive electrode, the first electrode EU may be formed using a transparent metal oxide such as indium tin oxide (ITO), indium zinc oxide (IZO), zinc oxide (ZnO), and indium tin zinc oxide (ITZO). If the first electrode EL1 is the transflective electrode or reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Also, the first electrode EL1 may include a plurality of layers including the reflective layer or transflective layer formed using the above materials, and a transparent conductive layer formed using ITO, IZO, ZnO, or ITZO. For example, the first electrode EL1 may have a three-layer structure of ITO/Ag/ITO. However, an embodiment of the present disclosure is not limited thereto.

The thickness of the first electrode EL1 may be from about 800 Å to about 10,000 Å, for example from about 1,000 Å to about 3,000 Å.

The hole transport region HTR is provided on the first electrode EL1. The hole transport region HTR may include at least one of a hole injection layer HIL, a hole transport layer HTL, a hole buffer layer, or an electron blocking layer. The thickness of the hole transport region HTR may be, for example, from about 1,000 Å to about 1,500 Å.

The hole transport region HTR may have a single layer formed using a single material, a single layer formed using a plurality of different materials, or a multilayer structure including a plurality of layers formed using a plurality of different materials.

For example, the hole transport region HTR may have the structure of a single layer such as a hole injection layer HIL and a hole transport layer HTL, or may have a structure of a single layer formed using a hole injection material and a hole transport material. In addition, the hole transport region HTR may have a structure of a single layer formed using a plurality of different materials, or a structure laminated one by one from the first electrode EL1 of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer, without limitation.

The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

The hole injection layer HIL may include, for example, a phthalocyanine compound such as copper phthalocyanine; N,N'-diphenyl-N,N'-bis-[4-(phenyl-m-tolyl-amino)-phenyl]-biphenyl-4,4'-diamine (DNTPD), 4,4',4''-tris(3-methylphenylphenylamino)triphenylamine (m-MTDATA), 4,4',4''-tris(N,N-diphenylamino)triphenylamine (TDATA), 4,4',4''-tris{N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-dinaphthalene-1-yl)-N,N'-diphenyl-benzidine (NPB), carbazole derivatives such as N-phenylcarbazole and polyvinyl carbazole, fluorine-based derivatives, triphenylamine-containing polyether ketone (TPAPEK), 4-isopropyl-4'-methyldiphenyliodonium tetrakis(pentafluorophenyl)borate, dipyrazino[2,3-f: 2',3'-h] quinoxaline-2,3,6,7,10,11-hexacarbonitrile (HAT-CN), etc.

The hole transport layer HTL includes, for example, carbazole derivatives such as N-phenyl carbazole and polyvinyl carbazole, fluorine-based derivatives, N,N'-bis(3-methylphenyl)-N,N'-diphenyl-[1,1-biphenyl]-4,4'-diamine (TPD), triphenylamine-based derivatives such as 4,4',4''-tris (N-carbazolyl)triphenylamine (TCTA), N,N'-di(1-naphthalene-1-yl)-N,N'-diphenyl-benzidine (NPB), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), 1,3-bis(N-carbazolyl)benzene (mCP), etc.

The thickness of the hole transport region HTR may be from about 100 Å to about 10,000 Å, for example, from about 100 Å to about 1,000 Å. If the hole transport region HTR includes both the hole injection layer HIL and the hole transport layer HTL, the thickness of the hole injection layer HIL may be from about 100 Å to about 10,000 Å, for example, from about 100 Å to about 1,000 Å, and the thickness of the hole transport layer HTL may be from about 30 Å to about 1,000 Å. If the thicknesses of the hole transport region HTR, the hole injection layer HIL, and the hole transport layer HTL satisfy the above-described ranges, satisfactory hole transport properties may be obtained without substantial increase of a driving voltage.

The hole transport region HTR may further include a charge generating material other than the above-described materials to improve conductivity. The charge generating material may be dispersed in the hole transport region HTR uniformly or non-uniformly. The charge generating material may be, for example, a p-dopant. The p-dopant may be one of quinone derivatives, metal oxides, or cyano group-containing compounds, without limitation. For example, non-limiting examples of the p-dopant may include quinone derivatives such as tetracyanoquinodimethane (TCNQ), and 2,3,5,6-tetrafluoro-tetracyanoquinodimethane (F4-TCNQ), metal oxides such as tungsten oxide, molybdenum oxide, HAT-CN, etc., without limitation.

As described above, the hole transport region HTR may further include at least one of a hole buffer layer or an electron blocking layer in addition to the hole injection layer HIL and the hole transport layer HTL. The hole buffer layer may compensate a resonance distance according to the wavelength of light emitted from the emission layer EML and increase light emission efficiency. Materials included in the hole transport region HTR may be used as materials included in the hole buffer layer. The electron blocking layer is a layer preventing or reducing electron injection from the electron transport region ETR to the hole transport region HTR.

The emission layer EML is provided on the hole transport region HTR. The thickness of the emission layer EML may be, for example, from about 100 Å to about 1,000 Å, or about 100 Å to about 500 Å. The emission layer EML may have a single layer formed using a single material, a single layer formed using a plurality of different materials, or a multilayer structure having a plurality of layers formed using a plurality of different materials.

The emission layer EML may include the above-described heterocyclic compound according to an embodiment of the present disclosure. For example, the emission layer EML may include a heterocyclic compound represented by the following Formula 1:

$$D_1\text{-}A\text{-}D_2 \qquad \text{Formula 1}$$

In Formula 1, A is represented by Formula 2 below, $D_1$ is represented by Formula 3 below, and $D_2$ is represented by Formula 4 below.

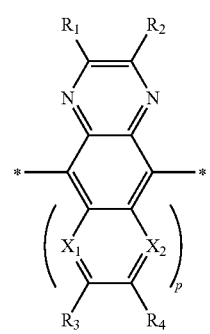

Formula 2

Formula 3

$Y_1 \text{—} (L_1)_{\overline{q}} \text{—} *$

Formula 4

$* \text{—} (L_2)_{\overline{r}} \text{—} Y_2$

The description of Formula 1 to Formula 4 is the same as that described above, and therefore, will not be repeated here.

The emission layer EML may include one or two or more kinds of the heterocyclic compounds represented by Formula 1. The emission layer EML may further include any suitable material available in the art in addition to the heterocyclic compound represented by Formula 1.

The emission layer EML may include a host and a dopant. The dopant may include the heterocyclic compound according to an embodiment of the present disclosure. The emission layer EML may include the heterocyclic compound according to an embodiment of the present disclosure and may be an emission layer emitting near-infrared rays. For example, the emission layer EML may be a layer emitting near-infrared rays in a wavelength region of about 750 nm to about 1,000 nm.

The host may be any suitable material available in the art, without specific limitation. Among a red host, a green host and a blue host, the red host may be more preferably used. The host may include at least one chosen from the following Compounds H-1 to H-15. However, an embodiment of the present disclosure is not limited thereto.

H-1

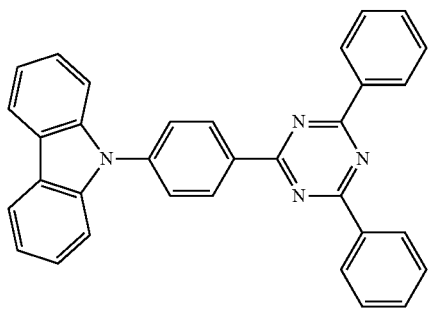

H-2

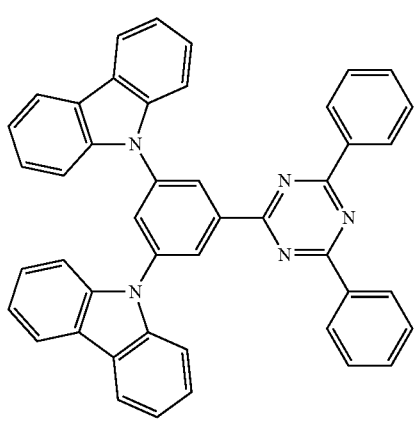

H-3

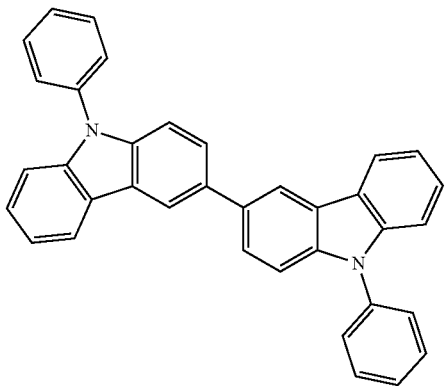

H-4

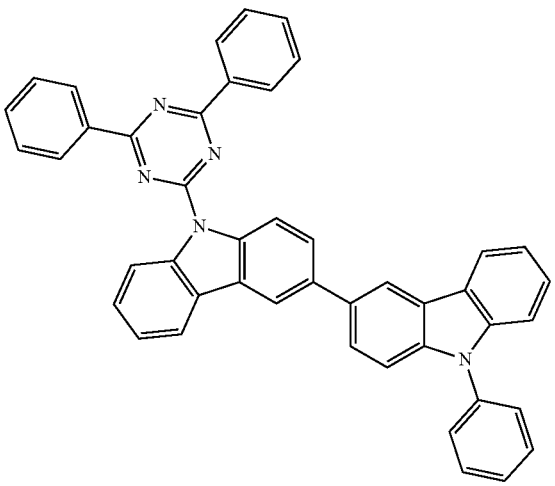

H-5

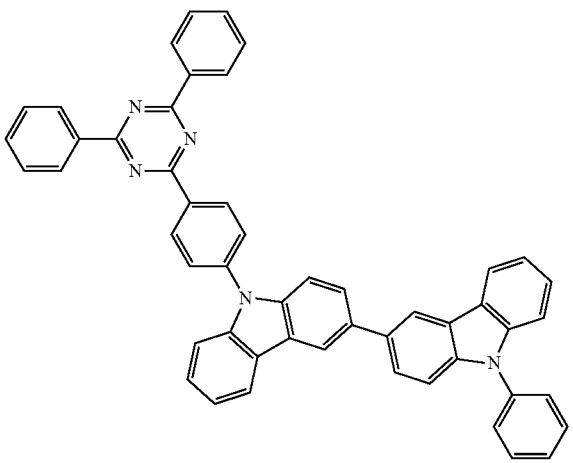

-continued
H-6
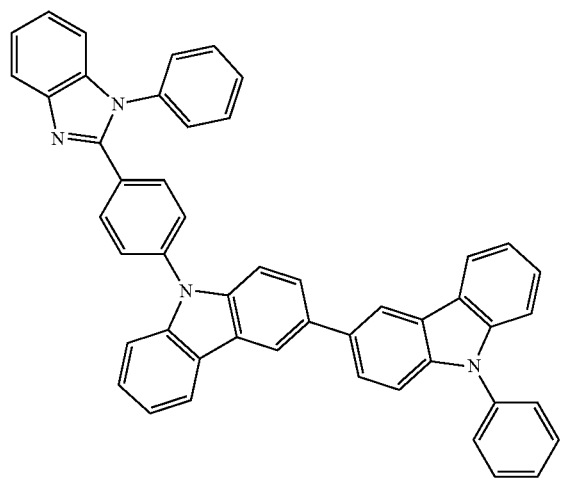
H-7
H-8
H-9
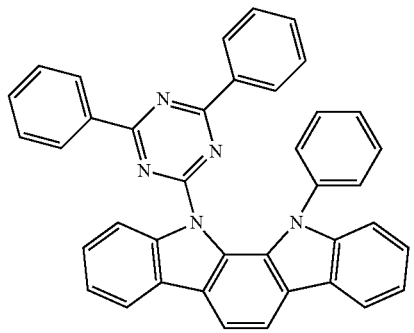
H-10
H-11
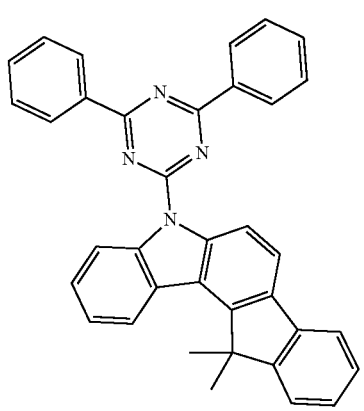
H-12
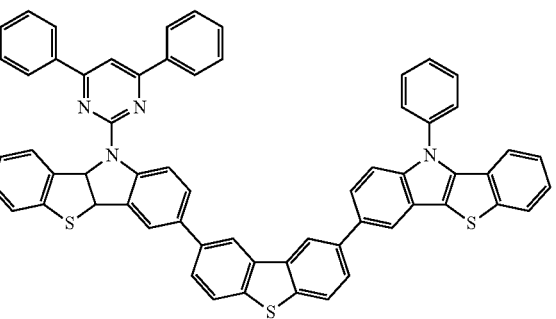

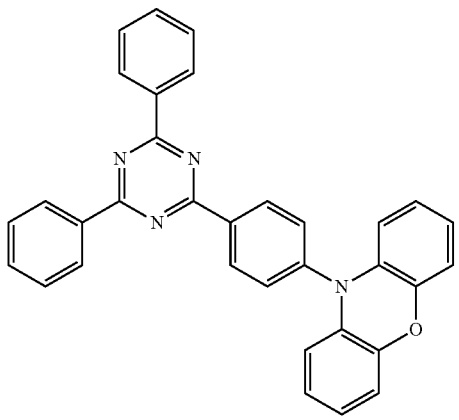

H-13

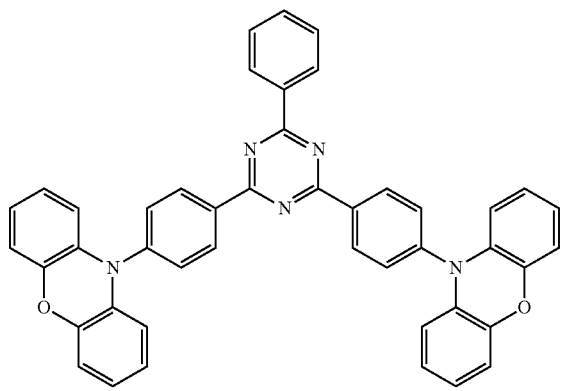

H-14

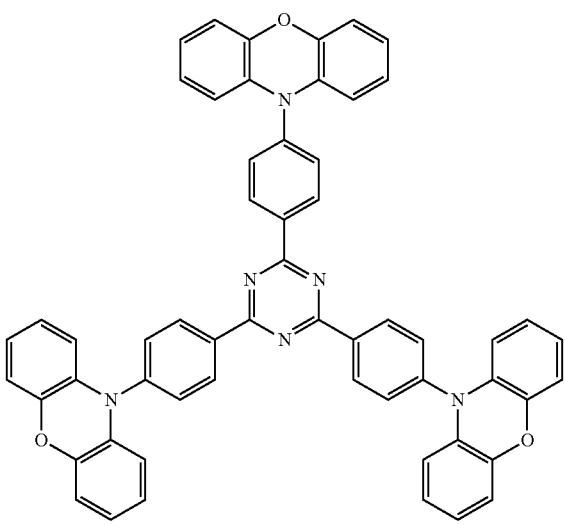

H-15

The electron transport region ETR is provided on the emission layer EML. The electron transport region ETR may include at least one of an hole blocking layer, an electron transport layer ETL, or an electron injection layer EIL, without limitation.

The electron transport region ETR may have a single layer formed using a single material, a single layer formed using a plurality of different materials, or a multilayer structure including a plurality of layers formed using a plurality of different materials.

For example, the electron transport region ETR may have the structure of a single layer such as an electron injection layer EIL and an electron transport layer ETL, or a single layer structure formed using an electron injection material and an electron transport material. In addition, the electron transport region ETR may have a single layer structure formed using a plurality of different materials, or a structure laminated one by one from the emission layer EML of electron transport layer ETL/electron injection layer EIL, or hole blocking layer/electron transport layer ETL/electron injection layer EIL, without limitation. The thickness of the electron transport region ETR may be, for example, from about 1,000 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and a laser induced thermal imaging (LITI) method.

If the electron transport region ETR includes the electron transport layer ETL, the electron transport region ETR may include an anthracene-based compound. However, an embodiment of the present disclosure is not limited thereto. The electron transport region may include, for example, tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-yl)phenyl)-9,10-dinaphthylanthracene, 1,3,5-tri(1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato)aluminum (BAlq), berylliumbis(benzoquinolin-10-olate (Bebq2), 9,10-di(naphthalene-2-yl)anthracene (ADN), or a mixture thereof, without limitation. The thickness of the electron transport layer ETL may be from about 100 Å to about 1,000 Å, for example, from about 150 Å to about 500 Å. If the thickness of the electron transport layer ETL satisfies the above-described range, satisfactory electron transport properties may be obtained without substantial increase of a driving voltage.

If the electron transport region ETR includes the electron injection layer EIL, the electron transport region ETR may include LiF, lithium quinolate (LiQ), $Li_2O$, BaO, NaCl, CsF, a metal in lanthanides such as Yb, or a metal halide such as RbCl and RbI, without limitation. The electron injection layer EIL also may be formed using a mixture material of an electron transport material and an insulating organo metal salt. The organo metal salt may be a material having an energy band gap of about 4 eV or more. For example, the organo metal salt may include, for example, a metal acetate, a metal benzoate, a metal acetoacetate, a metal acetylacetonate, or a metal stearate. The thickness of the electron injection layer EIL may be from about 1 Å to about 100 Å, and from about 3 Å to about 90 Å. If the thickness of the electron injection layer EIL satisfies the above described range, satisfactory electron injection properties may be obtained without inducing substantial increase of a driving voltage.

The electron transport region ETR may include a hole blocking layer, as described above. The hole blocking layer may include, for example, at least one of 2,9-dimethyl-4,7-diphenyl-1,10-phenanthroline (BCP), or 4,7-diphenyl-1,10-phenanthroline (Bphen), without limitation.

The second electrode EL2 is provided on the electron transport region ETR. The second electrode EL2 may be a common electrode or a cathode. The second electrode EL2 may be a transmissive electrode, a transflective electrode or a reflective electrode. If the second electrode EL2 is the transmissive electrode, the second electrode EL2 may include a transparent metal oxide, for example, ITO, IZO, ZnO, ITZO, etc.

If the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound including thereof, or a mixture thereof (for example, a mixture of Ag and Mg). The second electrode EL2 may have a multilayered structure including a reflective layer or a transflective layer formed using the above-described materials and a transparent conductive layer formed using ITO, IZO, ZnO, ITZO, etc.

The second electrode EL2 may be connected with an auxiliary electrode. If the second electrode EL2 is coupled or connected with the auxiliary electrode, the resistance of the second electrode EL2 may be decreased.

In the organic electroluminescence device 10, voltages are applied to each of the first electrode EL1 and the second electrode EL2, and holes injected from the first electrode EL1 move via the hole transport region HTR to the emission layer EML, and electrons injected from the second electrode EL2 move via the electron transport region ETR to the emission layer EML. The electrons and the holes are recombined in the emission layer EML to generate excitons, and the excitons may emit light via transition from an excited state to a ground state.

If the organic electroluminescence device 10 is a top emission type (or kind), the first electrode EL1 may be a reflective electrode, and the second electrode EL2 may be a transmissive electrode or a transflective electrode. If the organic electroluminescence device 10 is a bottom emission type (or kind), the first electrode EL1 may be the transmissive electrode or the transflective electrode, and the second electrode EL2 may be the reflective electrode.

The organic electroluminescence device according to an embodiment of the present disclosure is characterized in including the heterocyclic compound represented by Formula 1 in an emission layer and emitting near-infrared rays, and thus, is favorable in increasing efficiency and life, and decreasing a driving voltage.

Hereinafter, referring to FIGS. 3-9, an organic electroluminescence display device according to an embodiment of the present disclosure will be explained in further detail. The explanation will be mainly given with regard to the features different from the heterocyclic compound and the organic electroluminescence device including the same according to an embodiment of the present disclosure, and unexplained part will follow the above-description.

Figure 3:
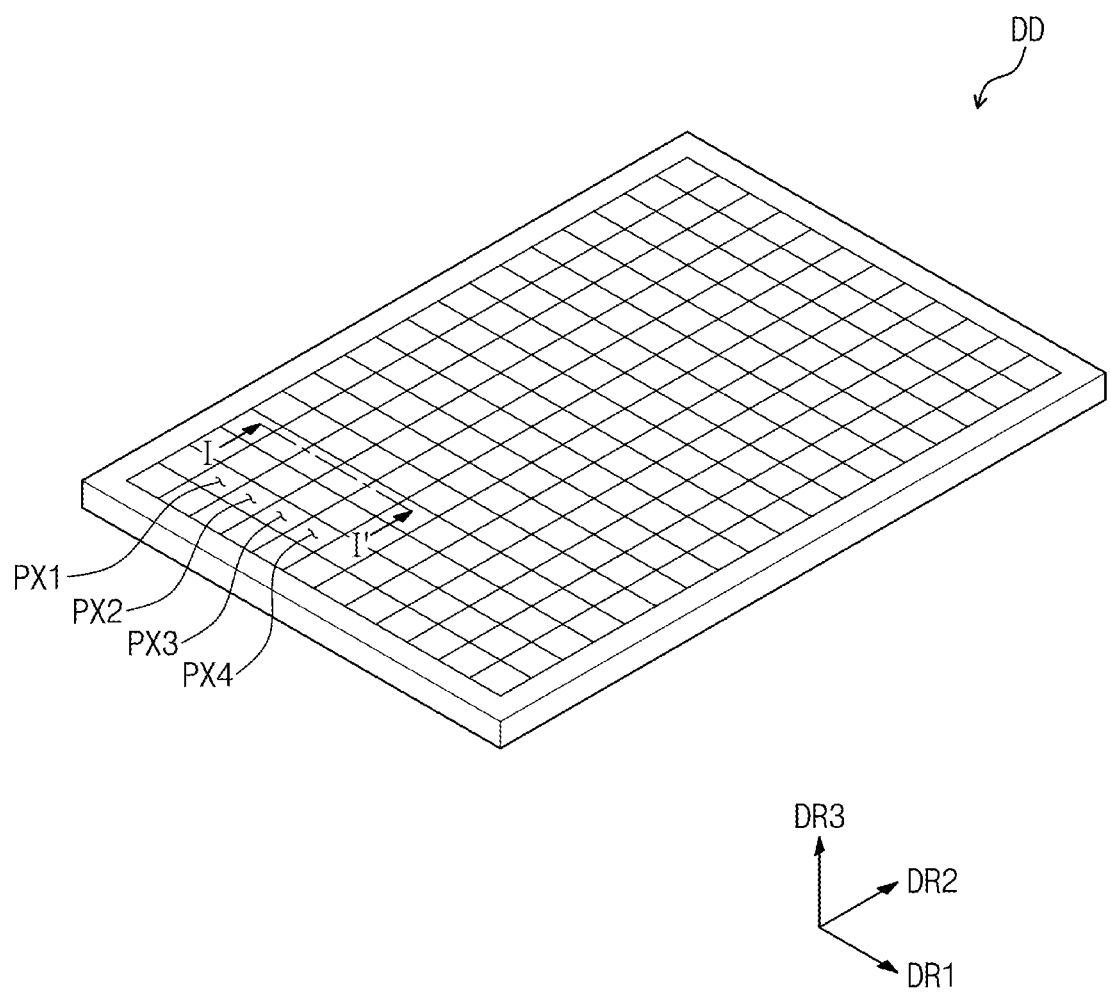
FIG. 3 is a perspective view of an organic electroluminescence display device according to an embodiment of the present disclosure.

FIG. 3 is a perspective view of an organic electroluminescence display device according to an embodiment of the present disclosure.

Referring to FIG. 3, an organic electroluminescence display device DD according to an embodiment of the present disclosure includes a plurality of pixels. FIG. 3 illustrates four kinds of pixels, and for example, illustrates a case including a first pixel PX1, a second pixel PX2, a third pixel PX3 and a fourth pixel PX4. Four kinds of the pixels PX1, PX2, PX3 and PX4 may produce lights in different wavelength regions, respectively.

For example, the four kinds of pixels PX1, PX2, PX3 and PX4 may be arranged in a matrix shape on a plane defined by an axis in a first direction DR1 and an axis in a second direction DR2, with a third direction DR3 being perpendicular or substantially perpendicular to the plane. In addition, each of the four kinds of pixels PX1, PX2, PX3 and PX4 may be arranged while making a row in the second direction DR2. However, an embodiment of the present disclosure is not limited thereto. The arrangement of a plurality of the pixels may be diversely modified according to embodiment methods of a display panel. In addition, each of the pixels PX1, PX2, PX3 and PX4 which generate lights in different wavelength regions may be defined as a sub-pixel, and the combination of such sub-pixels may be defined as a pixel (PX of FIG. 4).

Each of the four kinds of pixels PX1, PX2, PX3 and PX4 includes an organic electroluminescence device including an emission layer emitting light in a different wavelength region from each other. This will be described later.

Figure 4:
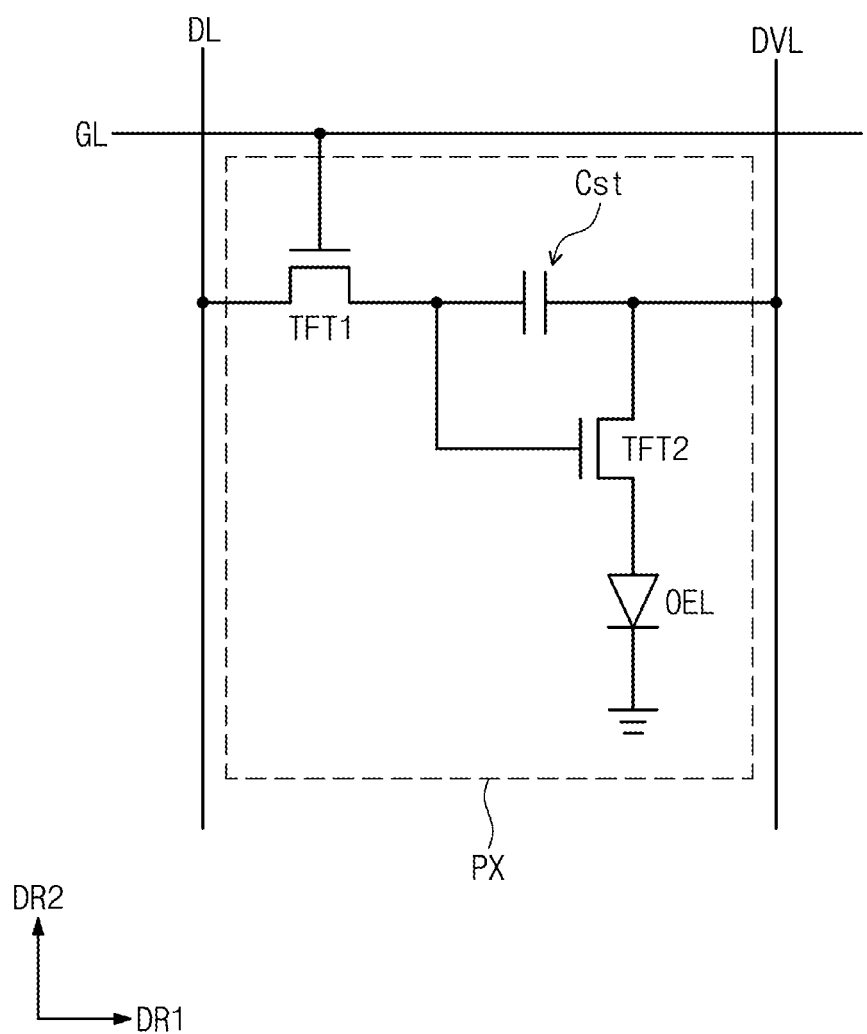
FIG. 4 is a circuit diagram of a pixel included in an organic electroluminescence display device according to an embodiment of the present disclosure.
Figure 5:
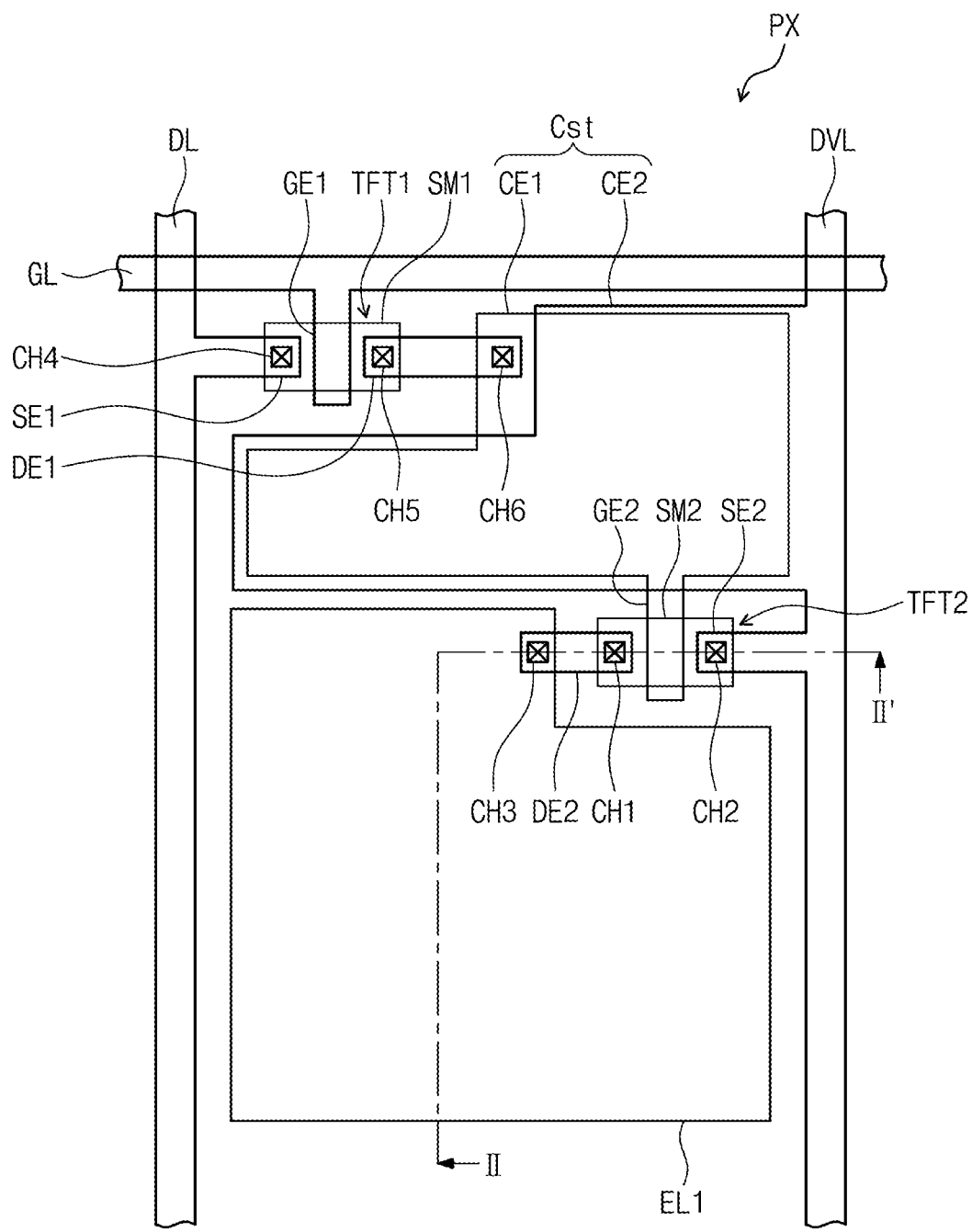
FIG. 5 is a plan view showing a pixel included in an organic electroluminescence display device according to an embodiment of the present disclosure.
Figure 6:
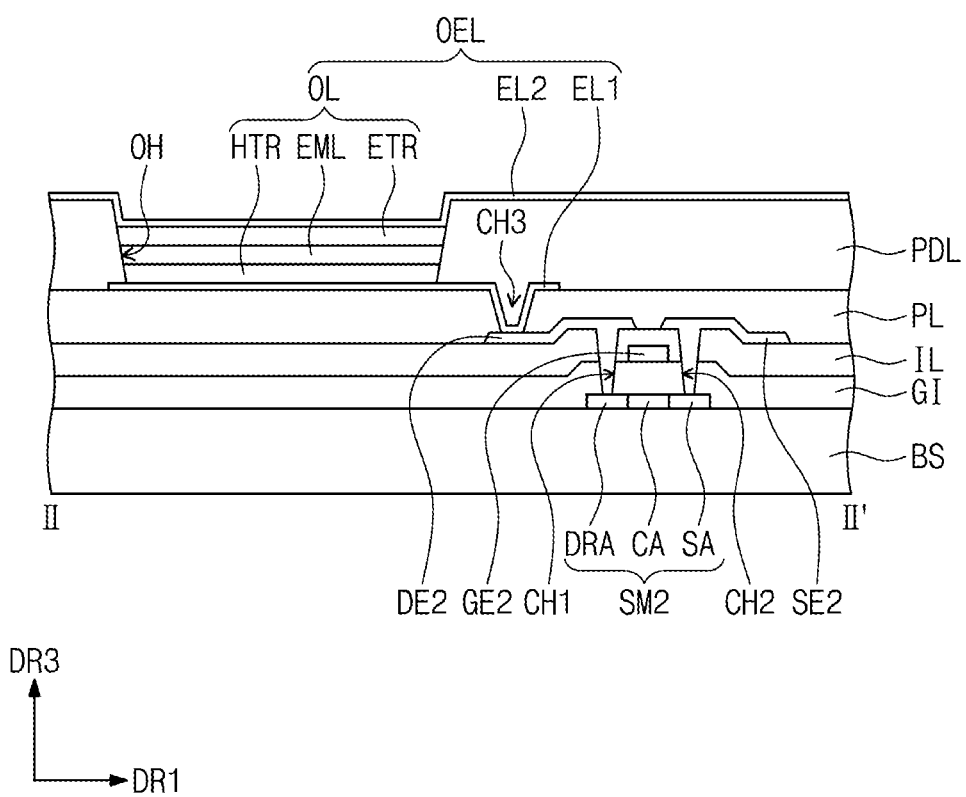
FIG. 6 is a cross-sectional view taken along a region II-II' of FIG. 5.

FIG. 4 is a circuit diagram of a pixel among pixels included in an organic electroluminescence display device according to an embodiment of the present disclosure. FIG. 5 is a plan view showing a pixel among pixels included in an organic electroluminescence display device according to an embodiment of the present disclosure. FIG. 6 is a cross-sectional view taken along a region II-II' of FIG. 5.

Referring to FIGS. 4-6, a pixel PX may be coupled or connected with a wire part including a gate line GL, a data line DL and a driving voltage line DVL. The pixel PX includes thin film transistors TFT1 and TFT2 coupled or connected to the wire part, and an organic electroluminescence device OEL coupled or connected to the thin film transistors TFT1 and TFT2, and a capacitor Cst.

The gate line GL is extended in a first direction DR1. The data line DL is extended in a second direction DR2 which crosses the gate line GL. The driving voltage line DVL is extended in substantially the same direction as the data line GL, for example, in the second direction DR2. The gate line GL delivers scanning signals to the thin film transistors TFT1 and TFT2, the data line DL delivers data signals to the thin film transistors TFT1 and TFT2, and the driving voltage line DVL provides the thin film transistors TFT1 and TFT2 with a driving voltage.

The thin film transistors TFT1 and TFT2 may include a driving thin film transistor TFT2 for controlling the organic electroluminescence device OEL and a switching thin film transistor TFT1 for switching the driving thin film transistor TFT2. In an embodiment of the present disclosure, a case where a pixel PX includes two thin film transistors TFT1 and TFT2 is explained. However, an embodiment of the present disclosure is not limited thereto. The pixel PX may include one thin film transistor and a capacitor, or the pixel PX may be provided with at least three thin film transistors and at least two capacitors.

The switching thin film transistor TFT1 includes a first gate electrode GE1, a first source electrode SE1 and a first drain electrode DE1. The first gate electrode GE1 is coupled or connected with the gate line GL, and the first source electrode SE1 is coupled or connected with the data line DL. The first drain electrode DE1 is coupled or connected with a first common electrode CE1 by a fifth contact hole CH5. The switching thin film transistor TFT1 delivers data signals applied to the data line DL to the driving thin film transistor TFT2 according to scanning signals applied to the gate line GL.

The driving thin film transistor TFT2 includes a second gate electrode GE2, a second source electrode SE2 and a second drain electrode DE2. The second gate electrode GE2 is coupled or connected with the first common electrode CE1. The second source electrode SE2 is coupled or connected with the driving voltage line DVL. The second drain electrode DE2 is coupled or connected with the first electrode EU by a third contact hole CH3.

The capacitor Cst is coupled or connected between the second gate electrode GE2 and the second source electrode SE2 of the driving thin film transistor TFT2 and charges and maintains data signals inputted to the second gate electrode GE2 of the driving thin film transistor TFT2. The capacitor Cst may include a first common electrode CE1 which is coupled or connected with the first drain electrode DE1 by a sixth contact hole CH6 and a second common electrode CE2 which is coupled or connected with the driving voltage line DVL.

The organic electroluminescence display device (DD of FIG. 3) according to an embodiment of the present disclosure may include a base substrate BS on which thin film transistors TFT1 and TFT2 and an organic electroluminescence device OEL are laminated. The base substrate BS may be formed using any suitable substrate available in the art without specific limitation, and may be formed using an insulating material, for example, glass, plastics, quartz, etc. Organic polymers forming the base substrate BS may include polyethylene terephthalate (PET), polyethylene naphthalate (PEN), polyimide, polyether sulfone, etc. The base substrate BS may be selected in consideration of mechanical strength, thermal stability, transparency, surface smoothness, ease of handling, water resistance, etc.

On the base substrate BS, a substrate buffer layer may be disposed. The substrate buffer layer may prevent or reduce the diffusion of impurities into the switching thin film transistor TFT1 and the driving thin film transistor TFT2. The substrate buffer layer may be formed using silicon nitride (SiNx), silicon oxide (SiOx), silicon oxynitride (SiOxNy), etc., and may be omitted according to the material of the base substrate BS and process conditions.

On the base substrate BS, a first semiconductor layer SM1 and a second semiconductor layer SM2 are disposed. The first semiconductor layer SM1 and the second semiconductor layer SM2 are formed using a semiconductor material, and are operated as active layers of the switching thin film transistor TFT1 and the driving thin film transistor TFT2, respectively. Each of the first semiconductor layer SM1 and the second semiconductor layer SM2 includes a source area SA, a drain area DRA and a channel area CA disposed between the source area SA and the drain area DRA. Each of the first semiconductor layer SM1 and the second semiconductor layer SM2 may be selected from an inorganic semiconductor or an organic semiconductor and formed. The source area SA and the drain area DRA may be doped with n-type impurities or p-type impurities.

On the first semiconductor layer SM1 and the second semiconductor layer SM2, a gate insulating layer GI is disposed. The gate insulating layer GI covers the first semiconductor layer SM1 and the second semiconductor layer SM2. The gate insulating layer GI may be formed using an organic insulating material or an inorganic insulating material.

On the gate insulating layer GI, a first gate electrode GE1 and a second gate electrode GE2 are disposed. Each of the first gate electrode GE1 and the second gate electrode GE2 is formed to cover the area corresponding to the channel area CA of each of the first semiconductor layer SM1 and the second semiconductor layer SM2.

On the first gate electrode GE1 and the second gate electrode GE2, an insulating interlayer IL is disposed. The insulating interlayer IL covers the first gate electrode GE1 and the second gate electrode GE2. The insulating interlayer IL may be formed using an organic insulating material or an inorganic insulating material.

On the insulating interlayer IL, a first source electrode SE1, a first drain electrode DE1, a second source electrode SE2 and a second drain electrode DE2 are disposed. The second drain electrode DE2 makes contact with a drain area DRA of a second semiconductor layer SM2 by a first contact hole CH1 formed in the gate insulating layer GI and the insulating interlayer IL, and the second source electrode SE2 makes contact with a source area SA of the second semiconductor layer SM2 by a second contact hole CH2 formed in the gate insulating layer GI and the insulating interlayer IL. The first source electrode SE1 makes contact with a source area of a first semiconductor layer SM1 by a fourth contact hole CH4 formed in the gate insulating layer GI and the insulating interlayer IL, and the first drain electrode DE1 makes contact with a drain area of the first semiconductor layer SM1 by a fifth contact hole CH5 formed in the gate insulating layer GI and the insulating interlayer IL.

On the first source electrode SE1, the first drain electrode DE1, the second source electrode SE2, and the second drain electrode DE2, a passivation layer PL is disposed. The passivation layer PL may play the role as a protection layer protecting the switching thin film transistor TFT1 and the driving thin film transistor TFT2, or play the role as a planarization layer planarizing the top surface thereof.

On the passivation layer PL, an organic electroluminescence device OEL is disposed. The organic electroluminescence device OEL includes a first electrode EL1, a second electrode EL2 disposed on the first electrode EL1, and an organic layer OL including an emission layer EML disposed between the first electrode EL1 and the second electrode EL2.

For example, on the passivation layer PL, the first electrode EL1 is provided, and on the passivation layer PL and the first electrode EL1, a pixel defining layer PDL is provided. In the pixel defining layer PDL, an opening part OH exposing at least a portion of the top surface of the first electrode EL1 is defined. The pixel defining layer PDL may partition the organic electroluminescence device OEL so as to correspond to each of the pixels PX.

The pixel defining layer PDL may be formed using a polymer resin. For example, the pixel defining layer PDL may be formed by including a polyacrylate-based resin or a polyimide-based resin. In addition, the pixel defining layer PDL may be formed by further including an inorganic material in addition to the polymer resin. Meanwhile, the pixel defining layer PDL may be formed by including a light absorbing material, or may be formed by including a black pigment or a black dye. The pixel defining layer PDL formed by including the black pigment or the black dye may accomplish a black pixel defining layer. During forming the pixel defining layer PDL, carbon black may be used as the black pigment or the black dye, but an embodiment of the present disclosure is not limited thereto.

In addition, the pixel defining layer PDL may be formed using an inorganic material. For example, the pixel defining layer PDL may be formed by including silicon nitride (SiNx), silicon oxide (SiOx), silicon oxynitride (SiOxNy), etc.

On the pixel defining layer PDL and the first electrode EL1, an organic layer OL and a second electrode EL2 are laminated one by one. The organic layer OL includes a hole transport region HTR, an emission layer EML, and an electron transport region ETR. Explanation on the first electrode EL1, the hole transport region HTR, the electron transport region ETR and the second electrode EL2 is the same as described above, and therefore, repeated description thereof will not be provided here.

Figure 7:
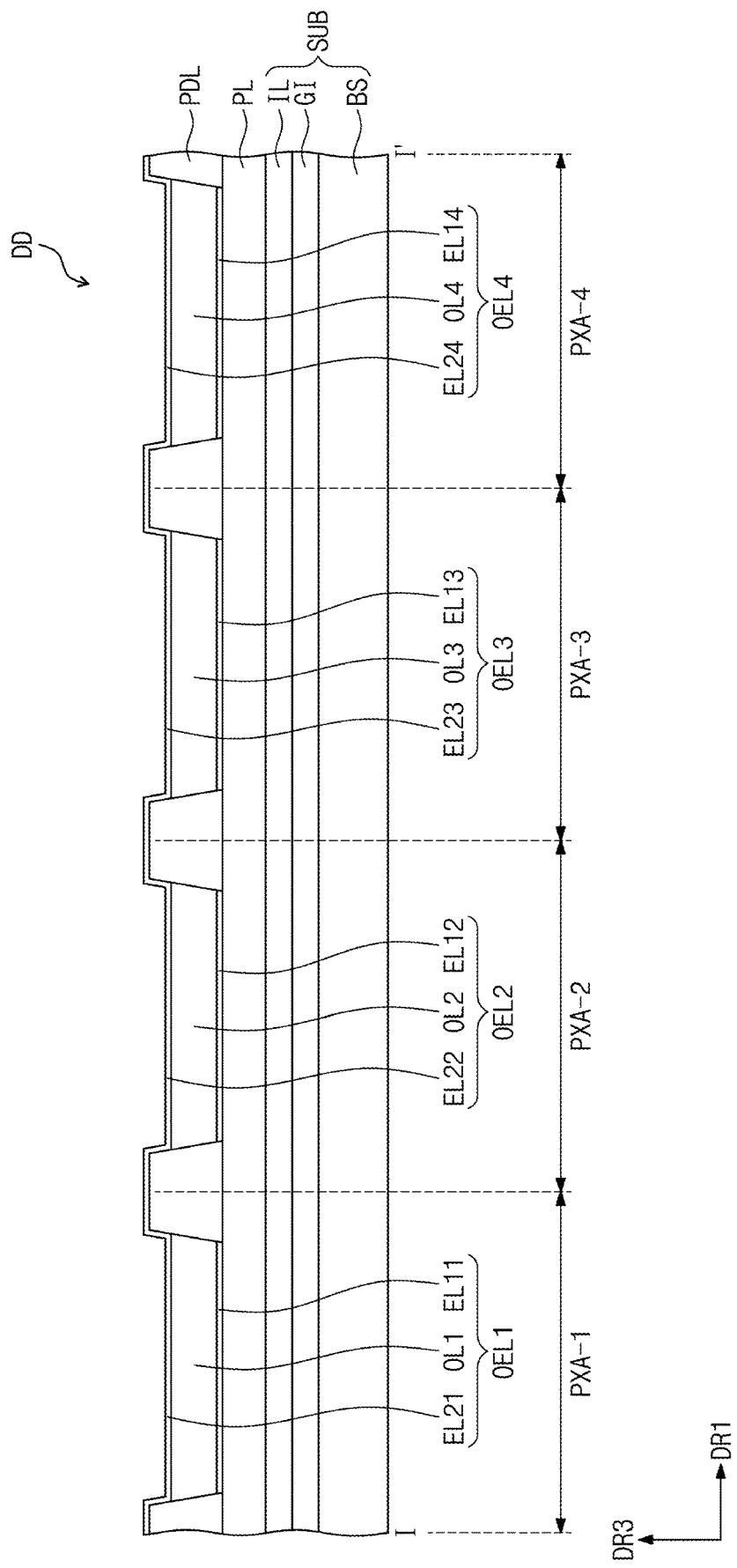
FIG. 7 is a cross-sectional view taken along a region I-I' of FIG. 3.

FIG. 7 is a cross-sectional view taken along a region I-I' of FIG. 3.

Referring to FIG. 7, the organic electroluminescence display device DD of the present disclosure may include a plurality of pixel areas PXA-1, PXA-2, PXA-3 and PXA-4. For example, a first pixel area PXA-1, a second pixel area PXA-2, a third pixel area PXA-3 and a fourth pixel area PXA-4 which emit lights in different wavelength regions, may be included. In an embodiment shown in FIG. 7, the first pixel area PXA-1 may be a blue pixel area, the second pixel area PXA-2 may be a green pixel area, the third pixel area PXA-3 may be a red pixel area, and the fourth pixel area PXA-4 may be a near-infrared pixel area. For example, in an embodiment, the organic electroluminescence display device DD may include a blue pixel area, a green pixel area, a red pixel area, and a near-infrared pixel area. For example, the blue pixel area is a blue light-emitting area which emits blue light, the green pixel area and the red pixel area represent a green light-emitting area and a red light-emitting area, respectively, and the near-infrared pixel area is an area emitting near-infrared rays in a wavelength region of about 750 nm to about 1,000 nm. Meanwhile, the pixel areas PXA-1, PXA-2, PXA-3 and PXA-4 may be light-emitting areas corresponding to the plurality of pixels PX1, PX2, PX3 and PX4, respectively, in the explanation referring to FIG. 3.

The first pixel area PXA-1 may be an area in which a first organic electroluminescence device OEL1 having a first organic layer OL1 which emits first visible rays is disposed. The second pixel area PXA-2 and the third pixel area PXA-3 may be areas in which a second organic electroluminescence device OEL2 which emits second visible rays and a third organic electroluminescence device OEL3 which emits third visible rays are disposed, respectively. The fourth pixel area PX-4 may be an area in which a fourth organic electroluminescence device OEL4 which emits near-infrared rays is disposed. The first visible rays, the second visible rays and the third visible rays may have different wavelength regions. However, an embodiment of the present disclosure is not limited thereto. They may have the same or substantially the same wavelength region, or two of the first visible rays, the second visible rays and the third visible rays may have the same or substantially the same wavelength region and the remaining one may have a different wavelength region.

The first pixel area PXA-1, the second pixel area PXA-2 and the third pixel area PXA-3 may be areas in which pixels achieving images are disposed, and the fourth pixel area PXA-4 may be an area in which a pixel other than the pixels achieving images is disposed.

For example, the first organic electroluminescence device OEL1 may include a first electrode EL11, a first organic layer OL1 and a second electrode EL21. Meanwhile, the first organic layer OL1 may include a hole transport region, an emission layer and an electron transport region. For example, the first organic layer OL1 may include an emission layer emitting blue light, and a luminescent material may be selected from any suitable blue light-emitting materials available in the art, without limitation. The second organic electroluminescence device OEL2 may include a first electrode EL12, a second organic layer OL2 and a second electrode EL22, and the third organic electroluminescence device OEL3 may include a first electrode EL13, a third organic layer OL3 and a second electrode EL23. The second organic layer OL2 and the third organic layer OL3 may include emission layers emitting green light and red light, respectively, and luminescent materials may be selected from any suitable green light-emitting materials and red light-emitting materials available in the art, without limitation.

Meanwhile, the fourth organic electroluminescence device OEL4 may correspond to the organic electroluminescence device (for example 10 of FIG. 1) according to an embodiment of the present disclosure. For example, the fourth organic electroluminescence device OEL4 may include an emission layer including a heterocyclic compound according to an embodiment of the present disclosure. The fourth organic electroluminescence device OEL4 includes a first electrode EL14, a fourth organic layer OL4 and a second electrode EL24, and the fourth organic layer OL4 may include an emission layer including the heterocyclic compound according to an embodiment of the present disclosure. The display device DD may include a substrate SUB including an insulating interlayer IL, a gate insulating layer GI, and a base substrate BS.

Referring to FIG. 3 again, each of the first pixel PX1, the second pixel PX2, the third pixel PX3 and the fourth pixel PX4 may be provided in plural.

In FIG. 3, the first pixel PX1, the second pixel PX2, the third pixel PX3 and the fourth pixel PX4 are arranged in the first direction DR1 as an illustration. However, an embodiment of the present disclosure is not limited thereto. In addition, in FIG. 3, the first pixel PX1, the second pixel PX2, the third pixel PX3 and the fourth pixel PX4 are shown to have the same size as an illustration. However, an embodiment of the present disclosure is not limited thereto.

Figure 8:
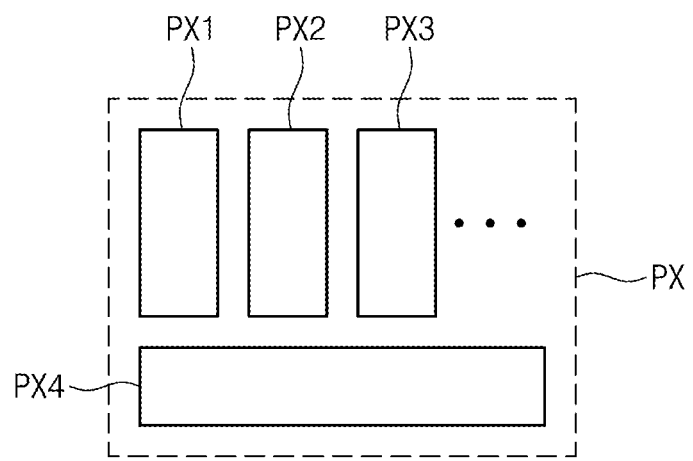
FIG. 8 is a plan view illustrating the relation of a pixel layout of an organic electroluminescence display device according to an embodiment of the present disclosure.
Figure 9:
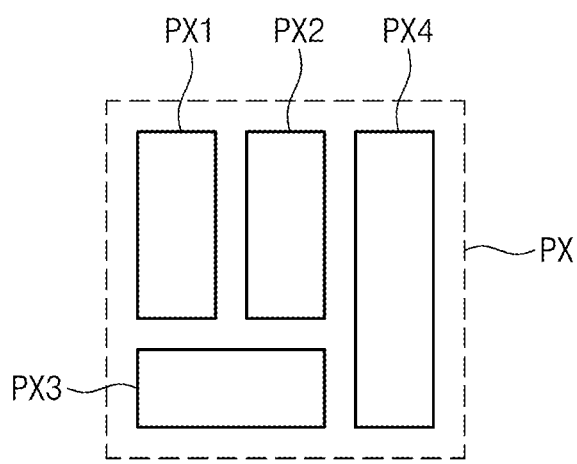
FIG. 9 is a plan view illustrating the relation of a pixel layout of an organic electroluminescence display device according to an embodiment of the present disclosure.

FIG. 8 is a plan view illustrating the relation of a pixel layout of an organic electroluminescence display device according to an embodiment of the present disclosure. FIG. 9 is a plan view illustrating the relation of a pixel layout of an organic electroluminescence display device according to an embodiment of the present disclosure.

Referring to FIGS. 8-9, at least one of a first pixel PX1, a second pixel PX2, a third pixel PX3 or a fourth pixel PX4 may have a different size. In addition, at least one of the first pixel PX1, the second pixel PX2, the third pixel PX3 or the fourth pixel PX4 may be extended in a different direction or may be arranged in a different direction.

The organic electroluminescence display device according to an embodiment of the present disclosure includes a pixel emitting near-infrared rays in a display area, and the pixel may be utilized as a pixel achieving sensing function using near-infrared rays. Accordingly, a configuration of sensing function such as fingerprint recognition and iris recognition may be disposed in a display area, thereby decreasing the area of a non-display area.

Hereinafter, the present disclosure will be explained in more detail referring to example embodiments. The following embodiments are only for illustration to assist the understanding of the present disclosure, but the scope of the present disclosure is not limited thereto.

Synthetic Examples

The heterocyclic compound according to an embodiment of the present disclosure may be synthesized, for example, as follows. However, the synthetic method of the heterocyclic compound according to an embodiment of the present disclosure is not limited thereto.

1. Synthesis of Compound 19

(1) Synthesis of Compound A

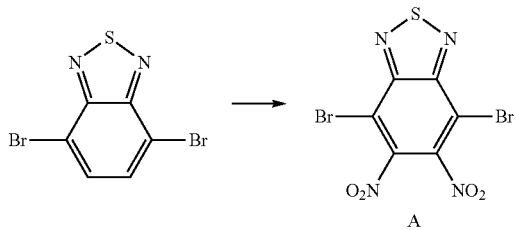

4,7-dibromobenzo[c]-1,2,5-thiadiazole and nitric acid were mixed with a trifluoromethanesulfonic acid solvent and stirred under a nitrogen atmosphere. After finishing the reaction, distilled water was slowly added and extraction with dichloromethane was performed. Water was removed from an extracted organic layer using MgSO$_4$, and the organic layer was concentrated in vacuum. The crude product was separated by column chromatography using dichloromethane/petroleum ether to obtain 4,7-dibromo-5,6-dinitrobenzo[c][1,2,5]thiadiazole as Compound A.

(2) Synthesis of Compound 19-1

Under a nitrogen atmosphere, 4,7-dibromo-5,6-dinitrobenzol[c][1,2,5]thiadiazole (1 eq) and Pd(PPh$_3$)$_4$ (0.05 eq) were dissolved in THF, and tributyl(thiophen-2-yl)stannane (2.2 eq) dissolved in THF was added thereto. Then, the reaction mixture was refluxed and stirred for about 15 hours. After finishing the reaction, the reaction product was cooled to room temperature, distilled water was slowly injected thereto, and extraction was performed using dichloromethane. Water was removed from an extracted organic layer using MgSO$_4$, and the organic layer was concentrated in vacuum. The crude product was separated by column chromatography using dichloromethane/petroleum ether to obtain Compound 19-1 (yield: 87%).

(3) Synthesis of Compound 19-3

Under a nitrogen atmosphere, Compound 19-1 (1 eq) and activated Zn (3 eq) were dissolved in acetic acid, followed by stirring at about 70° C. for about 1 hour. In this case, since Compound 19-2 thus produced was very unstable, the reaction mixture was filtered to remove remaining Zn after the reaction, and oxalaldehyde (2 eq) was added to a filtrate solution, followed by stirring at about 100° C. conditions for about 20 hours. After finishing the reaction, the reaction product was cooled to room temperature, distilled water was

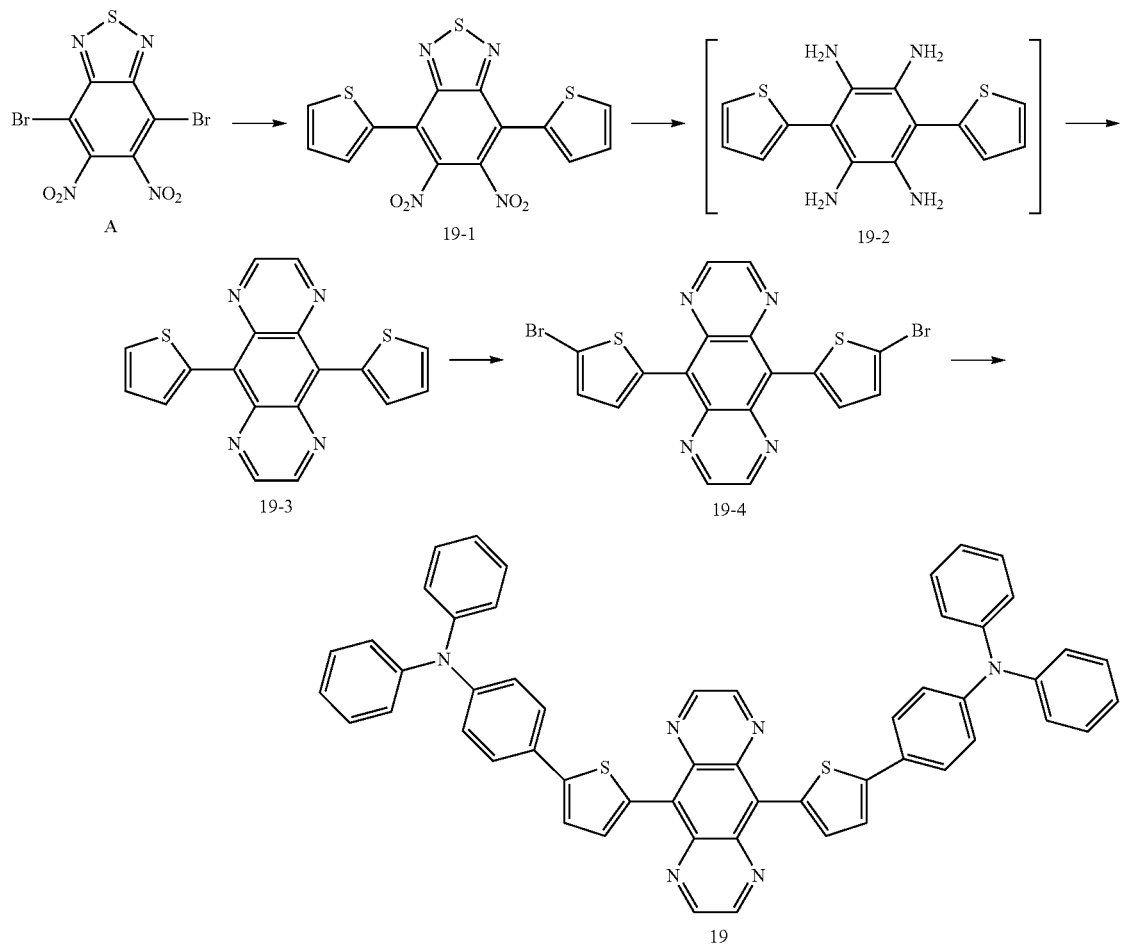

slowly injected thereto, and extraction was performed using dichloromethane. Water was removed from an extracted organic layer using MgSO$_4$, and the organic layer was concentrated in vacuum. The crude product was separated by column chromatography using dichloromethane/petroleum ether to obtain Compound 19-3 (yield: 20%).

(4) Synthesis of Compound 19-4

Under a nitrogen atmosphere, Compound 19-3 (1 eq) was dissolved in a THF solvent. N-bromosuccinimide (2.2 eq) dissolved in small quantity of THF was slowly injected to a reaction mixture at about 0° C. without light, followed by stirring at room temperature for about 8 hours. After finishing the reaction, distilled water was slowly injected thereto, and extraction was performed using dichloromethane. Water was removed from an extracted organic layer using MgSO$_4$, and the organic layer was concentrated in vacuum. The crude product was separated by column chromatography using dichloromethane/petroleum ether to obtain Compound 19-4 (yield: 83%).

(5) Synthesis of Compound 19

Under a nitrogen atmosphere, Compound 19-4 (1 eq), Pd(Ph$_3$)$_4$ (0.05 eq), and K$_2$CO$_3$ (1.2 eq) were dissolved in toluene, and (4-(diphenylamino)phenyl)boronic acid (2.3 eq) dissolved in small quantity of toluene was injected thereto. The reaction mixture was refluxed for about 15 hours. After finishing the reaction, the reaction product was cooled to room temperature, distilled water was slowly injected thereto, and extraction was performed using dichloromethane. Water was removed from an extracted organic layer using MgSO$_4$, and the organic layer was concentrated in vacuum. The crude product was separated by column chromatography using dichloromethane/petroleum ether to obtain Compound 19 (yield: 75%).

2. Synthesis of Compound 11

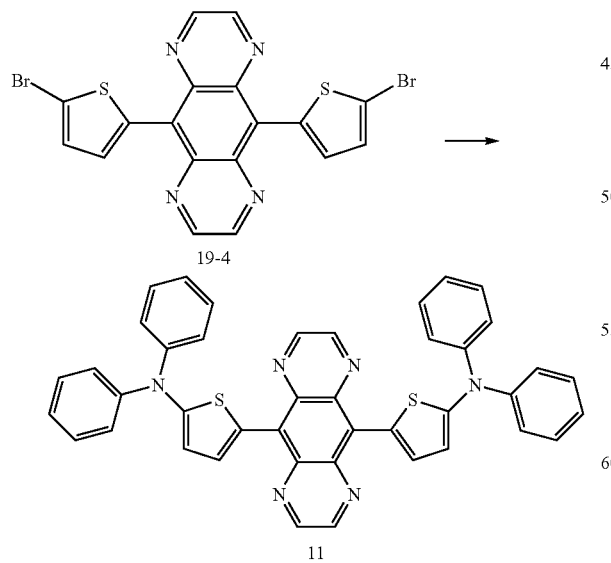

Under a nitrogen atmosphere, Compound 19-4 (1 eq), diphenylamine (2 eq), Pd(OAc)$_2$ (0.05 eq), P(t-Bu)$_3$ (50 wt %, 0.05 eq), and sodium tert-butoxide (NaOt-Bu, 2 eq) were stirred with a toluene solvent, followed by stirring and refluxing in 120° C. conditions. After finishing the reaction, the reaction product was cooled to room temperature, and extraction was performed using water and dichloromethane. Water was removed from an extracted organic layer using MgSO$_4$, and the organic layer was concentrated in vacuum. The crude product was separated by column chromatography using dichloromethane/petroleum ether to obtain Compound 11 (yield: 59%).

3. Synthesis of Compound 30

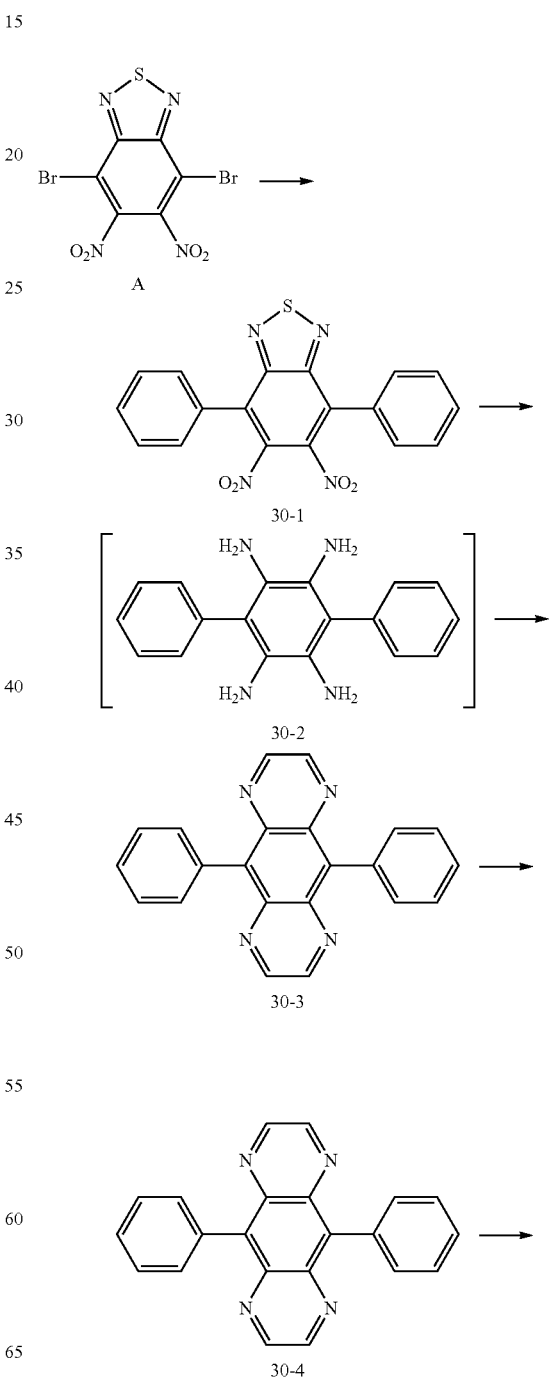

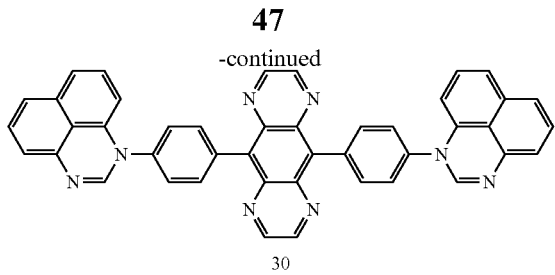

(1) Synthesis of Compound 30-1

Under a nitrogen atmosphere, Compound A (1 eq), Pd(Ph$_3$)$_4$ (0.05 eq), and K$_2$CO$_3$ (1.2 eq) were dissolved in toluene, and phenylboronic acid (2.3 eq) dissolved in small quantity of toluene was injected thereto, followed by stirring and refluxing for about 15 hours. After finishing the reaction, the reaction product was cooled to room temperature, distilled water was slowly injected thereto, and extraction was performed using dichloromethane. Water was removed from an extracted organic layer using MgSO$_4$, and the organic layer was concentrated in vacuum. The crude product was separated by column chromatography using dichloromethane/petroleum ether to obtain Compound 30-1 (yield: 81%).

(2) Synthesis of Compound 30-3

Under a nitrogen atmosphere, Compound 30-1 (1 eq) and activated Zn (3 eq) were dissolved in acetic acid, followed by stirring at about 70° C. for about 1 hour. In this case, since Compound 30-2 thus produced was very unstable, and the reaction mixture was filtered to remove only remaining Zn after the reaction, and oxalaldehyde (2 eq) was added to a filtrate solution, followed by stirring at about 100° C. conditions for about 20 hours. After finishing the reaction, the reaction product was cooled to room temperature, distilled water was slowly injected thereto, and extraction was performed using dichloromethane. Water was removed from an extracted organic layer using MgSO$_4$, and the organic layer was concentrated in vacuum. The crude product was separated by column chromatography using dichloromethane/petroleum ether to obtain Compound 30-3 (yield: 20%).

(3) Synthesis of Compound 30-4

Under a nitrogen atmosphere, Compound 30-3 (1 eq) was dissolved in a THF solvent. N-bromosuccinimide (2.2 eq) dissolved in small quantity of THF was slowly injected to a reaction mixture at about 0° C. without light, followed by stirring at room temperature for about 8 hours. After finishing the reaction, distilled water was slowly injected thereto, and extraction was performed using dichloromethane. Water was removed from an extracted organic layer using MgSO$_4$, and the organic layer was concentrated in vacuum. The crude product was separated by column chromatography using dichloromethane/petroleum ether to obtain Compound 30-4 (yield: 87%).

(4) Synthesis of Compound 30

Under a nitrogen atmosphere, Compound 30-4 (1 eq), 1H-perimidine (2 eq), Pd(OAc)$_2$ (0.05 eq), P(t-Bu)$_3$ (50 wt %, 0.05 eq), and sodium tert-butoxide (NaOt-Bu, 2 eq) were stirred with a toluene solvent, followed by stirring and refluxing in 120° C. conditions for about 12 hours. After finishing the reaction, the reaction product was cooled to room temperature, and extraction was performed using water and dichloromethane. Water was removed from an extracted organic layer using MgSO$_4$, and the organic layer was concentrated in vacuum. The crude product was separated by column chromatography using dichloromethane/petroleum ether to obtain Compound 30 (yield: 54%).

4. Synthesis of Compound 12

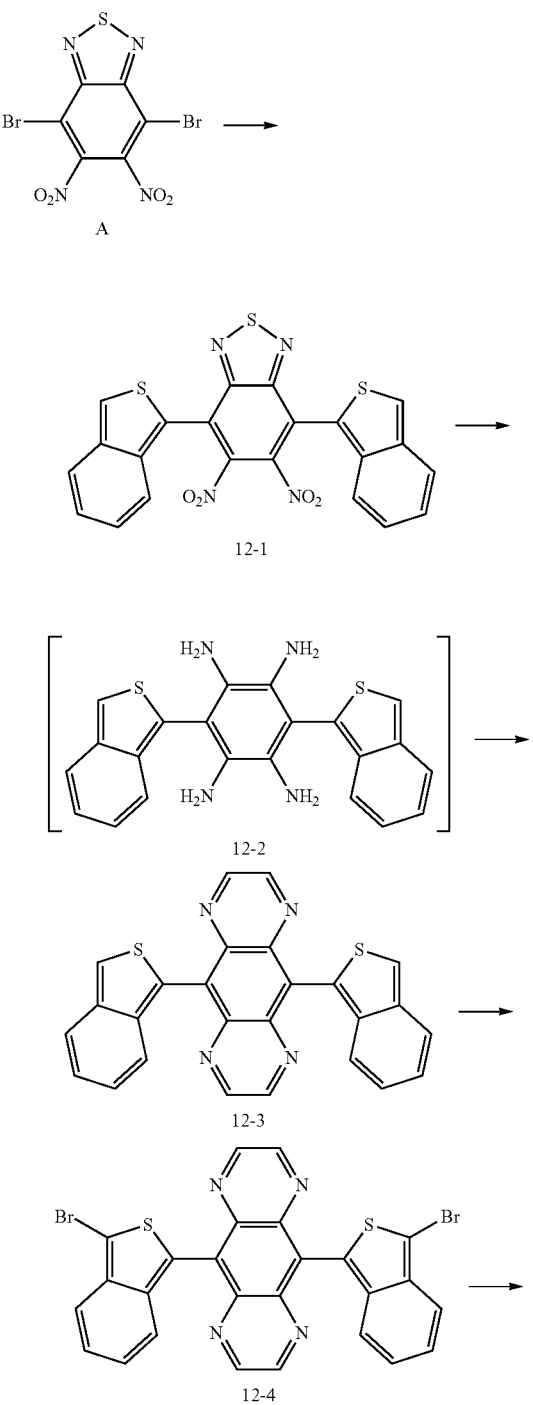

-continued

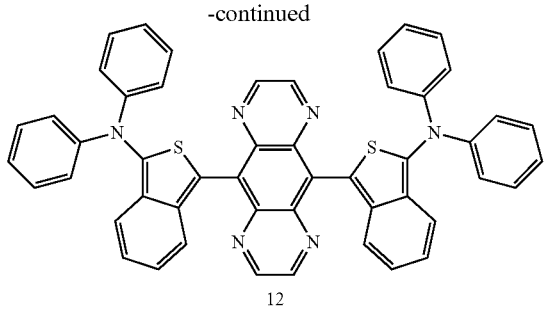

12

(1) Synthesis of Compound 12-1

Under a nitrogen atmosphere, Compound A (1 eq), and Pd(Ph$_3$)$_4$ (0.05 eq) were dissolved in THF, and benzo[c]thiophen-1-yltributylstannane (2.2 eq) dissolved in THF was injected thereto. Then, the reaction mixture was stirred and refluxed for about 15 hours. After finishing the reaction, the reaction product was cooled to room temperature, distilled water was slowly injected thereto, and extraction was performed using dichloromethane. Water was removed from an extracted organic layer using MgSO$_4$, and the organic layer was concentrated in vacuum. The crude product was separated by column chromatography using dichloromethane/petroleum ether to obtain Compound 12-1 (yield: 41%).

(2) Synthesis of Compound 12-3

Under a nitrogen atmosphere, Compound 12-1 (1 eq) and activated Zn (3 eq) were dissolved in acetic acid, followed by stirring at about 70° C. for about 1 hour. In this case, since Compound 12-2 thus produced was very unstable, and the reaction mixture was filtered to remove only remaining Zn after the reaction, and oxalaldehyde (2 eq) was added to a filtrate solution, followed by stirring in about 100° C. conditions for about 20 hours. After finishing the reaction, the reaction product was cooled to room temperature, distilled water was slowly injected thereto, and extraction was performed using dichloromethane. Water was removed from an extracted organic layer using MgSO$_4$, and the organic layer was concentrated in vacuum. The crude product was separated by column chromatography using dichloromethane/petroleum ether to obtain Compound 12-3 (yield: 11%).

(3) Synthesis of Compound 12-4

Under a nitrogen atmosphere, Compound 12-3 (1 eq) was dissolved in a THF solvent. N-bromosuccinimide (2.2 eq) dissolved in small quantity of THF was slowly injected to a reaction mixture at about 0° C. without light, followed by stirring at room temperature for about 8 hours. After finishing the reaction, distilled water was slowly injected thereto, and extraction was performed using dichloromethane. Water was removed from an extracted organic layer using MgSO$_4$, and the organic layer was concentrated in vacuum. The crude product was separated by column chromatography using dichloromethane/petroleum ether to obtain Compound 12-4 (yield: 72%).

(4) Synthesis of Compound 12

Under a nitrogen atmosphere, Compound 12-4 (1 eq), diphenylamine (2 eq), Pd(OAc)$_2$ (0.05 eq), P(t-Bu)$_3$ (50 wt %, 0.05 eq), and sodium tert-butoxide (NaOt-Bu, 2 eq) were stirred with a toluene solvent, followed by stirring with refluxing in 120° C. conditions for about 12 hours. After finishing the reaction, the reaction product was cooled to room temperature, and extraction was performed using water and dichloromethane. Water was removed from an extracted organic layer using MgSO$_4$, and the organic layer was concentrated in vacuum. The crude product was separated by column chromatography using dichloromethane/petroleum ether to obtain Compound 12 (yield: 19%).

5. Synthesis of Compound 20

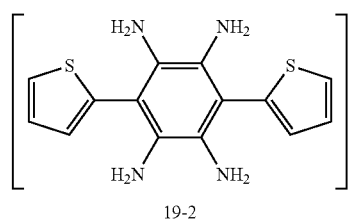

19-2

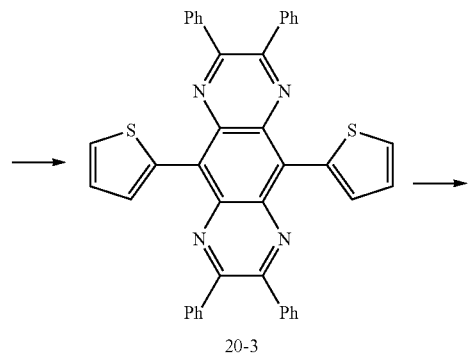

20-3

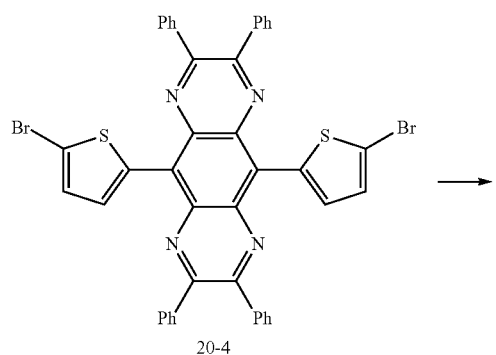

20-4

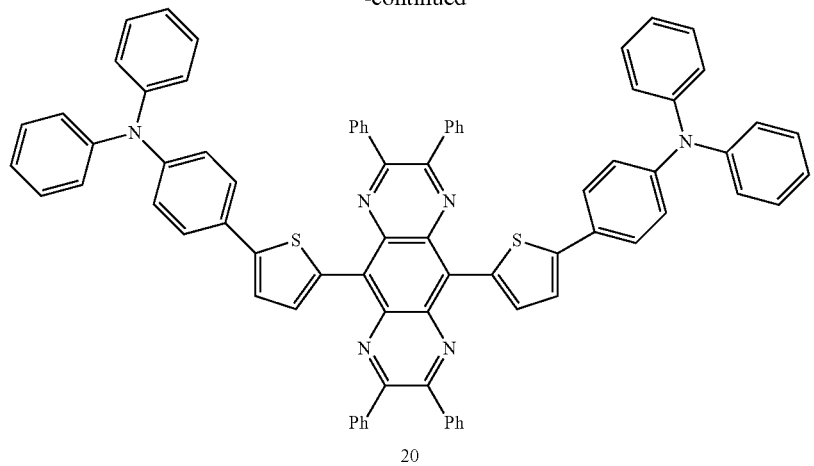

20

(1) Synthesis of Compound 20-3

Compound 19-2 was prepared in substantially the same manner as in the synthesis of Compound 19, except benzil (2 eq) was added to a filtrate mixture solution, followed by stirring in about 100° C. conditions for about 20 hours. After finishing the reaction, the reaction product was cooled to room temperature, distilled water was slowly injected thereto, and extraction was performed using dichloromethane. Water was removed from an extracted organic layer using $MgSO_4$, and the organic layer was concentrated in vacuum. The crude product was separated by column chromatography using dichloromethane/petroleum ether to obtain Compound 20-3 (yield: 16%).

(2) Synthesis of Compound 20-4

Under a nitrogen atmosphere, Compound 20-3 (1 eq) was dissolved in a THF solvent. N-bromosuccinimide (2.2 eq) dissolved in small quantity of THF was slowly injected to a reaction mixture at about 0° C. without light, followed by stirring at room temperature for about 8 hours. After finishing the reaction, distilled water was slowly injected thereto, and extraction was performed using dichloromethane. Water was removed from an extracted organic layer using $MgSO_4$, and the organic layer was concentrated in vacuum. The crude product was separated by column chromatography using dichloromethane/petroleum ether to obtain Compound 20-4 (yield: 76%).

(3) Synthesis of Compound 20

Under a nitrogen atmosphere, Compound 20-4 (1 eq), $Pd(Ph_3)_4$ (0.05 eq), and $K_2CO_3$ (1.2 eq) were dissolved in toluene, and (4-diphenylamino)phenyl)boronic acid (2.3 eq) dissolved in small quantity of toluene was injected thereto, followed by stirring and refluxing for about 15 hours. After finishing the reaction, the reaction product was cooled to room temperature, distilled water was slowly injected thereto, and extraction was performed using dichloromethane. Water was removed from an extracted organic layer using $MgSO_4$, and the organic layer was concentrated in vacuum. The crude product was separated by column chromatography using dichloromethane/petroleum ether to obtain Compound 20 (yield: 68%).

The physical properties of Compounds 11, 12, 19, 20 and 30 are listed in Table 1 below.

TABLE 1

| Compound | HOMO (eV) | LUMO (eV) | ΔE (eV) | $S_1$ (nm) | $S_1$ (eV) | $f/S_1$ |
|---|---|---|---|---|---|---|
| Compound 11 | −4.68 | −3.00 | 1.67 | 864.7 | 1.43 | 0.54 |
| Compound 12 | −4.82 | −3.03 | 1.79 | 869.5 | 1.43 | 0.34 |
| Compound 19 | −4.80 | −3.13 | 1.67 | 865.6 | 1.43 | 0.74 |
| Compound 20 | −4.50 | −2.74 | 1.75 | 845.7 | 1.47 | 0.57 |
| Compound 30 | −4.98 | −3.42 | 1.56 | 985.5 | 1.26 | 0.02 |

In Table 1, f is oscillator strength, and it may be anticipated that the greater the f/S1 value is, the higher the emission efficiency is.

(Device Manufacturing Examples)

Organic electroluminescence devices of Examples 1 and 2 were manufactured using Compounds 19 and 20 as dopant materials in an emission layer.

Example Compounds

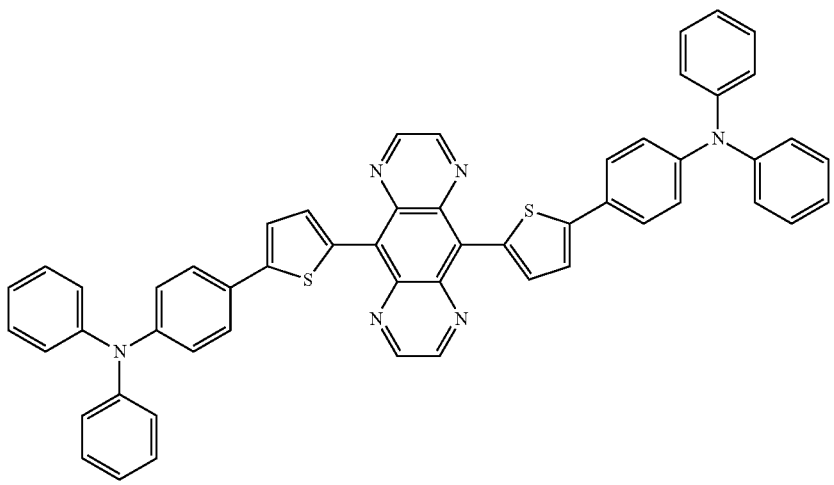

19

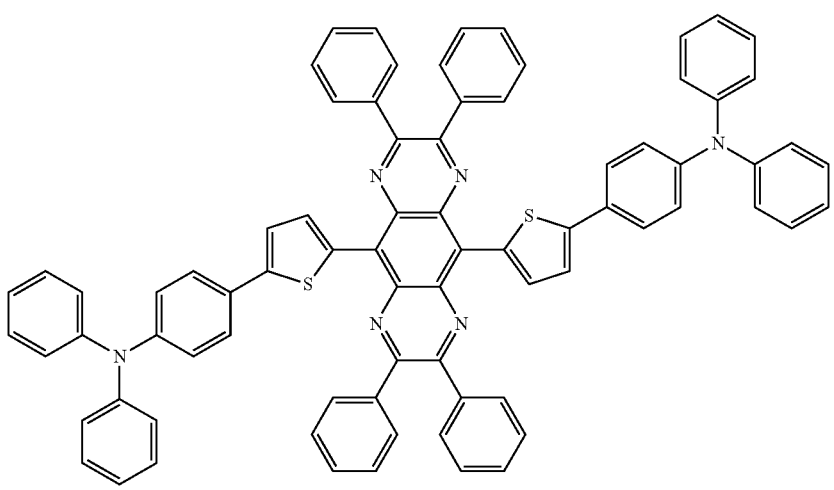

20

An organic electroluminescence device of Comparative Example 1 was manufactured using phthalocyanines of platinum (PtPc) as a dopant material of an emission layer.

The organic electroluminescence devices of Examples 1 and 2 and Comparative Example 1 were manufactured as follows.

On a glass substrate, an ITO layer with a thickness of about 1,200 Å was formed. Then, ultrasonic cleaning and pre-treatment (UV/O$_3$, heat treatment) were performed. On the pre-treated ITO transparent electrode, i) a hole injection layer (p-doping 1%, 100 Å), ii) a hole transport layer (1,100 Å), iii) an emission layer (host+dopant 1%, 300 Å), iv) an electron transport layer (ET1+ET2, 300 Å), v) an electron injection layer (LiF, 5 Å), and vi) a second electrode (Al, 1,500 Å) were laminated one by one.

The materials of the hole injection layer, the hole transport layer, the emission layer (host), and the electron transport layer are as follows.

(Hole injection layer material)

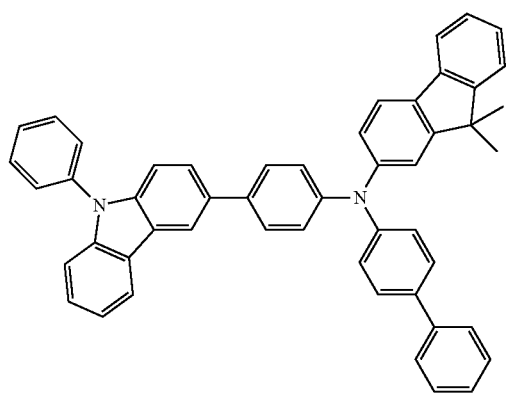

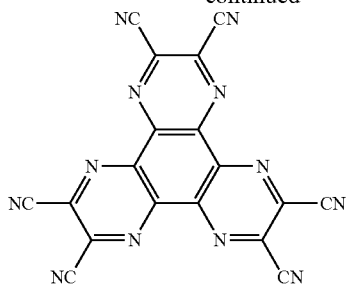

P-dopant
(Hole transport layer material)

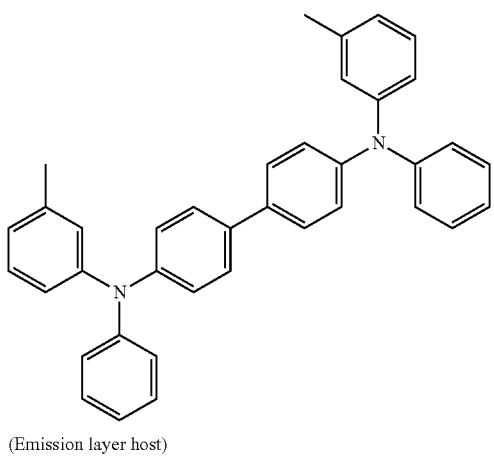

(Emission layer host)

H-8

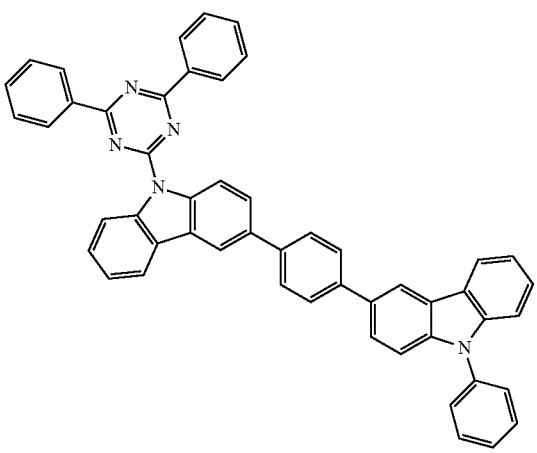

(Electron transport layer material)

ET1

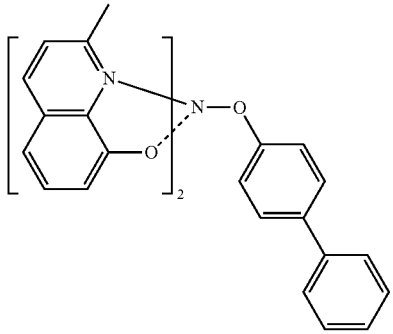

ET2

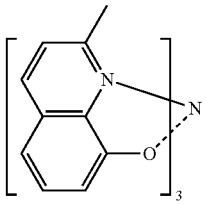

Then, the driving voltage, external quantum efficiency (EQE), and maximum light-emitting wavelength of the organic electroluminescence devices were measured. Evaluation results are listed in Table 2 below. The driving voltage, EQE, etc. are measured values at a current density of about 100 mA/cm$^2$.

TABLE 2

|  | Driving voltage (V) | EQE (%) | $\lambda_{MAX}$ |
|---|---|---|---|
| Example 1 | 6.3 | 2.52 | 900 |
| Example 2 | 5.9 | 2.57 | 900 |
| Comparative Example 1 | 7.9 | 0.50 | 968 |

Referring to the results of Table 2, it may be found that Example 1 and Example 2 had decreased driving voltage and increased efficiency when compared to Comparative Example 1. The compound according to an embodiment of the present disclosure emits NIR and has more favorable efficiency and driving life in contrast to PtPc which is an NIR emitting material.

The organic electroluminescence device and the organic electroluminescence display device including the heterocyclic compound according to an embodiment of the present disclosure are capable of emitting near-infrared rays with high efficiency.

As used herein, the term "and/or" includes any and all combinations of one or more of the associated listed items. Expressions such as "at least one of," when preceding a list of elements, modify the entire list of elements and do not modify the individual elements of the list.

As used herein, the terms "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present disclosure refers to "one or more embodiments of the present disclosure." As used herein, the terms "use," "using," and "used" may be considered synonymous with the terms "utilize," "utilizing," and "utilized," respectively. Also, the term "exemplary" is intended to refer to an example or illustration.

Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Although the exemplary embodiments of the present disclosure have been described, it is understood that the subject matter of the present disclosure should not be limited to these exemplary embodiments but various changes and modifications can be made by one ordinary skilled in the art within the spirit and scope of the present disclosure as hereinafter claimed.

What is claimed is:

1. A heterocyclic compound represented by the following Formula 1:

D₁-A-D₂                                    Formula 1 wherein in Formula 1, A is represented by the following Formula 2, D₁ is represented by the following Formula 3, and D₂ is represented by the following Formula 4:

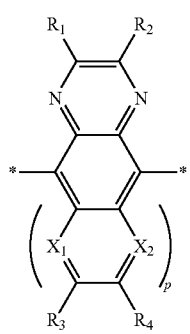

Formula 2

Y₁—(L₁)ᵩ—*                                Formula 3

*—(L₂)ᵣ—Y₂                                Formula 4 wherein in Formulae 2 to 4,
q and r are each independently an integer of 0 to 3,
p is 0 or 1,
$X_1$ and $X_2$ are each independently CR' or N,
R' and $R_1$ to $R_4$ are each independently a hydrogen atom, a deuterium atom, a substituted or unsubstituted alkyl group having 1 to 10 carbon atoms, or a substituted or unsubstituted aryl group having 6 to 30 carbon atoms for forming a ring,
$L_1$ and $L_2$ are each independently a substituted or unsubstituted arylene group having 6 to 30 carbon atoms for forming a ring, or a substituted or unsubstituted heteroarylene group having 2 to 30 carbon atoms for forming a ring,
$Y_1$ and $Y_2$ are each independently a substituted or unsubstituted arylamine group, a substituted or unsubstituted aryl group having 6 to 30 carbon atoms for forming a ring, or a substituted or unsubstituted heteroaryl group having 2 to 30 carbon atoms for forming a ring, and
at least one of $Y_1$ or $Y_2$ is an electron-donating group,
in case p is 0, $Y_1$ and $Y_2$ are each independently represented by the following Formula 5:

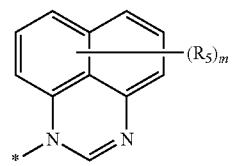

Formula 5 wherein in Formula 5,
$R_5$ is a hydrogen atom, a deuterium atom, a substituted or unsubstituted alkyl group having 1 to 10 carbon atoms, or a substituted or unsubstituted aryl group having 6 to 30 carbon atoms for forming a ring, and
m is an integer of 0 to 6, and
wherein the heterocyclic compound emits near-infrared rays in a wavelength region of about 750 nm to about 1,000 nm.

2. The heterocyclic compound of claim 1, wherein p is 1, and $X_1$ and $X_2$ are N.

3. The heterocyclic compound of claim 1, wherein at least one of $Y_1$ or $Y_2$ is represented by one of the above Formula 5, the following Formula 6 or the following Formula 7:

*—N(Ar₁)(Ar₂)                             Formula 6

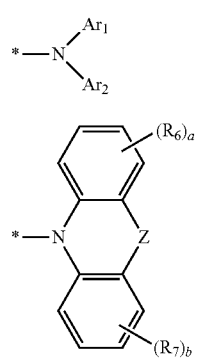

Formula 7 wherein in Formula 6,
$Ar_1$ and $Ar_2$ are each independently a substituted or unsubstituted aryl group having 6 to 30 carbon atoms for forming a ring,
wherein in Formula 7,
Z is a direct linkage, O, S, or $NR_8$,
$R_6$ to $R_8$ are each independently a hydrogen atom, a deuterium atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring, and
a and b are each independently an integer of 0 to 4.

4. The heterocyclic compound of claim 1, wherein at least one chosen from $R_1$ to $R_4$ is a substituted or unsubstituted alkyl group having 1 to 10 carbon atoms, or a substituted or unsubstituted aryl group having 6 to 30 carbon atoms for forming a ring.

5. The heterocyclic compound of claim 4, wherein at least one chosen from $R_1$ to $R_4$ is a substituted or unsubstituted methyl group or a substituted or unsubstituted phenyl group.

6. The heterocyclic compound of claim 1, wherein $D_1$ and $D_2$ are symmetric about A.

7. The heterocyclic compound of claim 6, wherein $X_1$ and $X_2$ are the same.

8. The heterocyclic compound of claim 1, wherein $L_1$ and $L_2$ are each independently represented by one of the following Formulae 8-1 to 8-4:

Formula 8-1

Formula 8-2
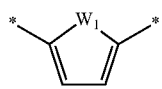

Formula 8-3
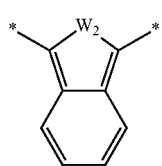

Formula 8-4
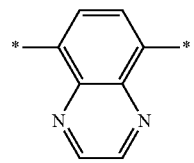

wherein in Formulae 8-2 and 8-3, $W_1$ and $W_2$ are each independently $NR_9$, S, or O, and $R_9$ is a hydrogen atom, a deuterium atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 2 to 30 carbon atoms for forming a ring.

9. The heterocyclic compound of claim 1, wherein $Y_1$ and $Y_2$ are different from each other.

10. The heterocyclic compound of claim 1, wherein the heterocyclic compound represented by Formula 1 is one selected from compounds represented in the following Compound Group 1:

Compound Group 1

1
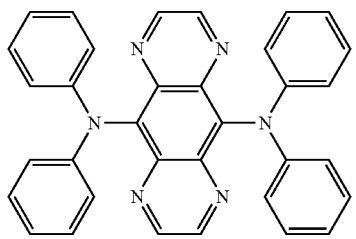

2
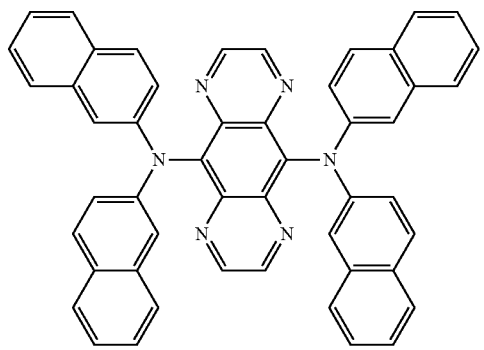

3
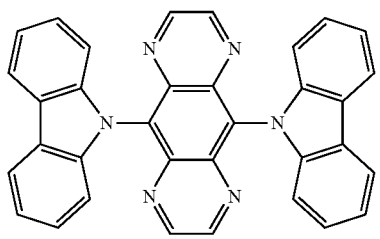

4
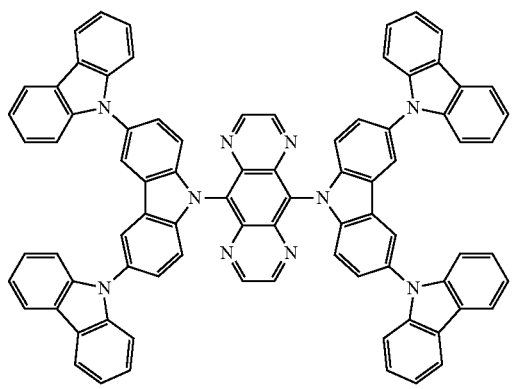

-continued
5
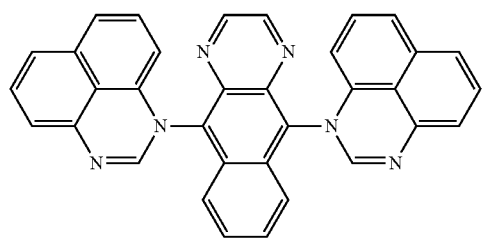
6
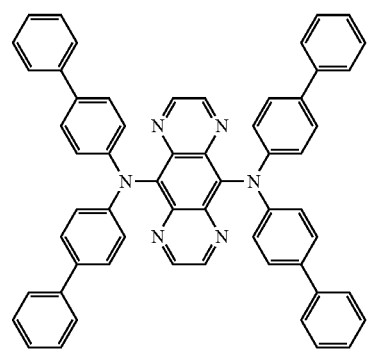
7
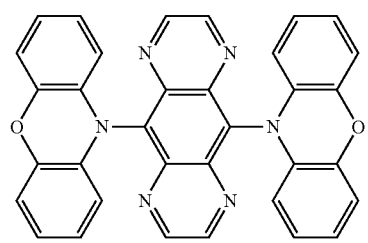
8
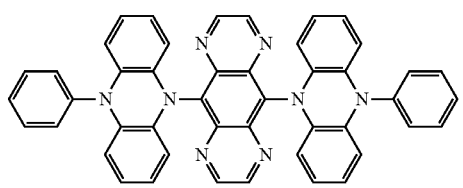
9
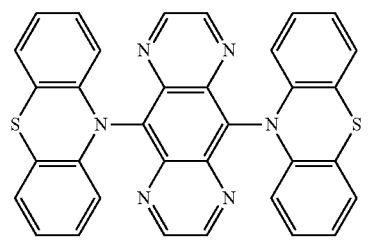
10
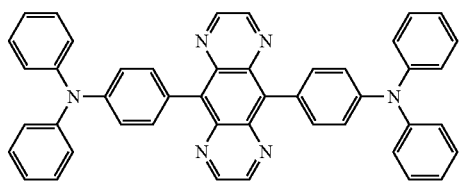
11
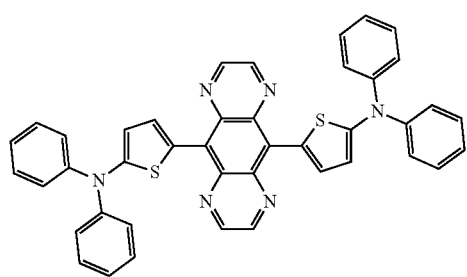
12
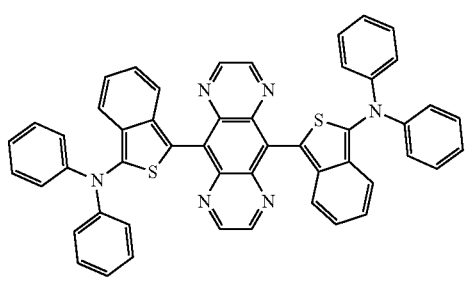
13
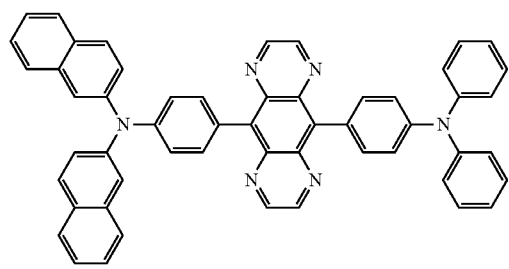
14
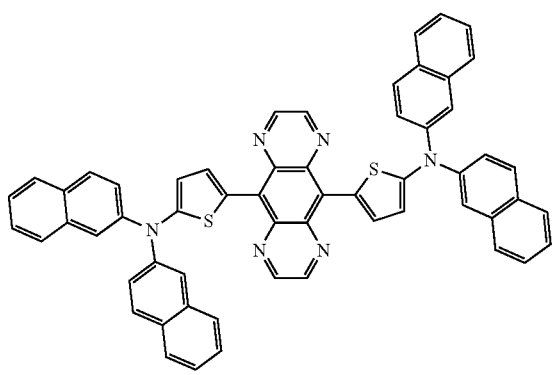

-continued
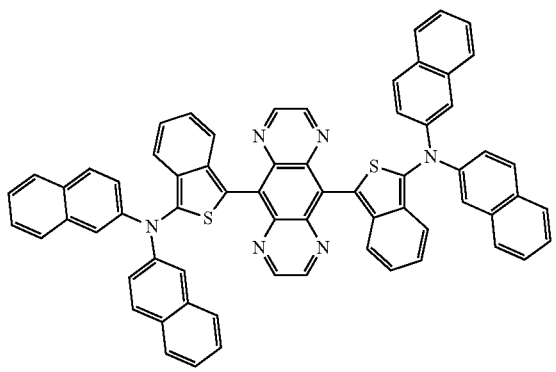# 15
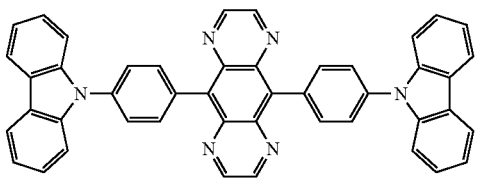# 16
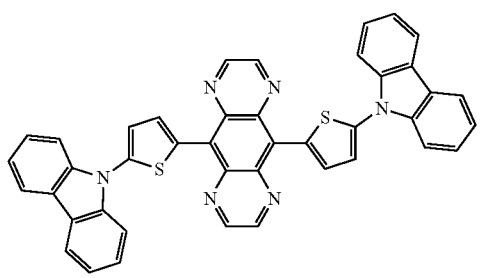# 17
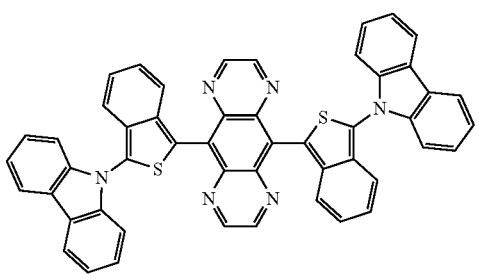# 18
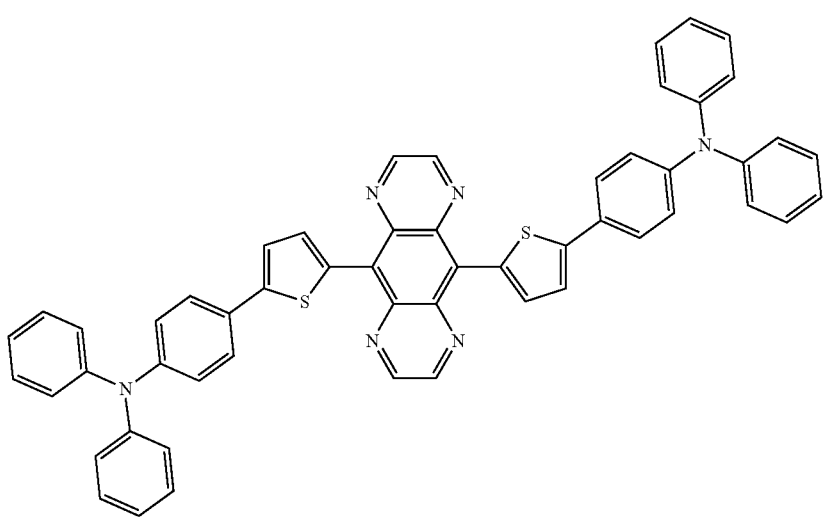# 19

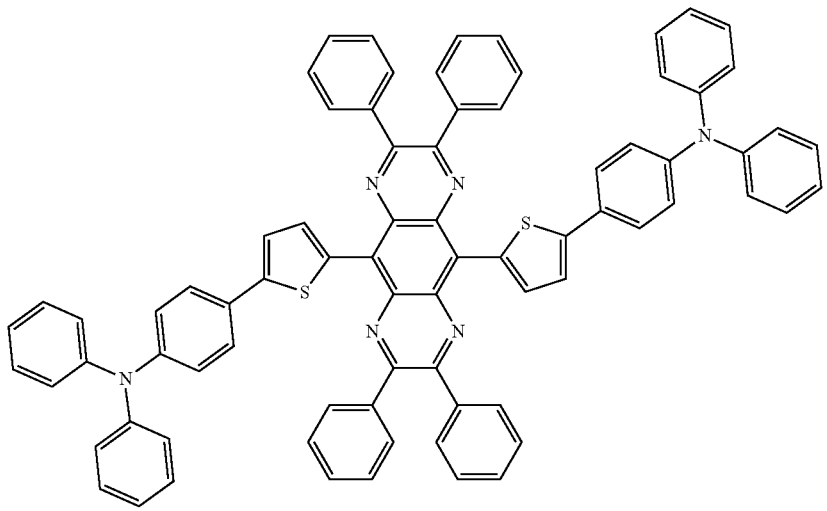
20
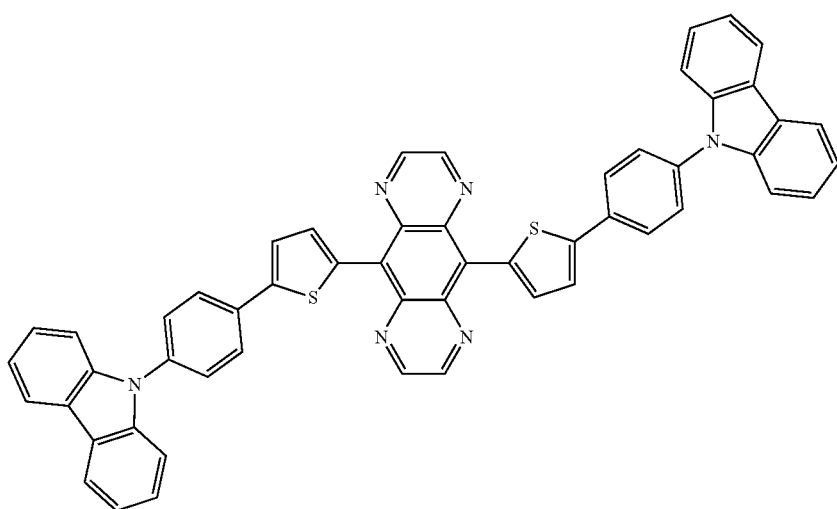
21
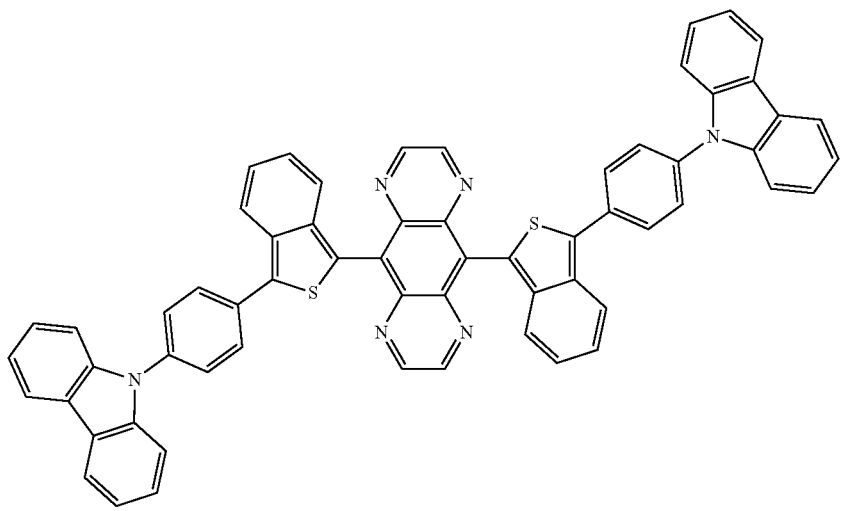
22

23
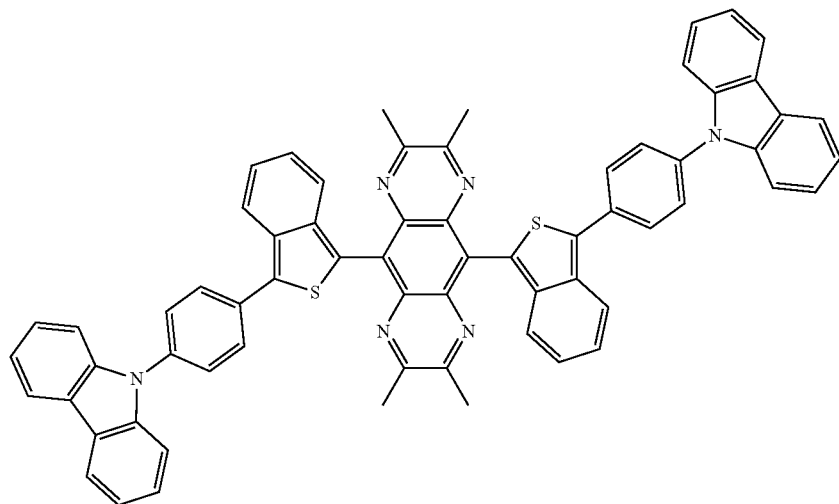
24
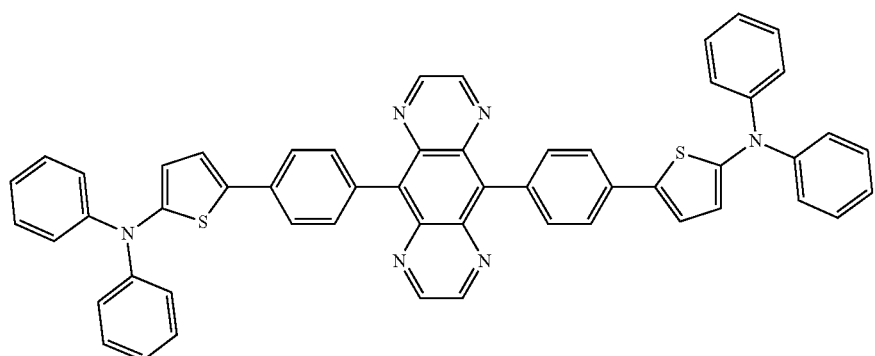
25
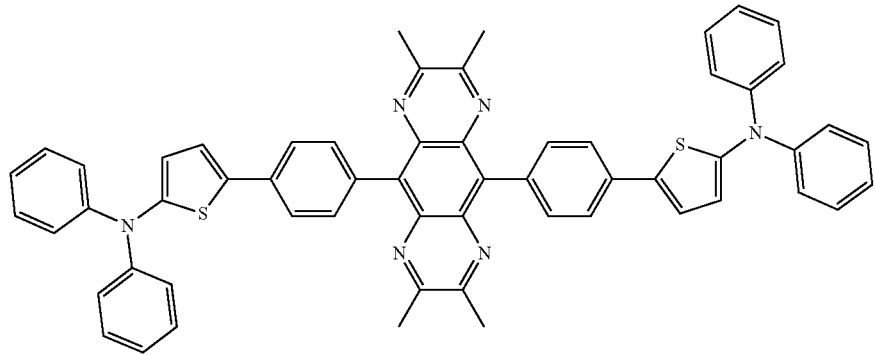
26
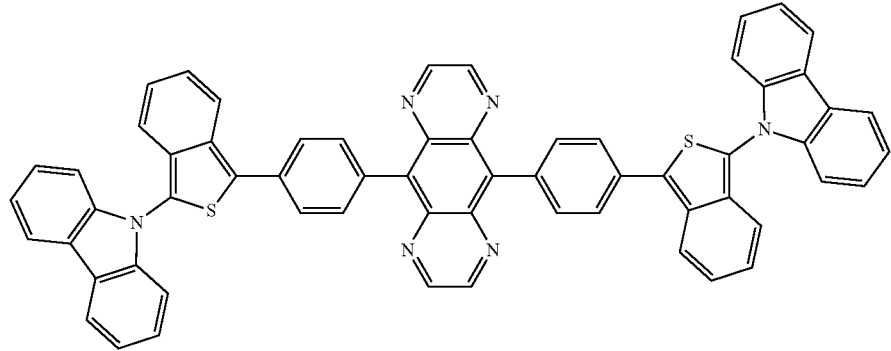

-continued
27
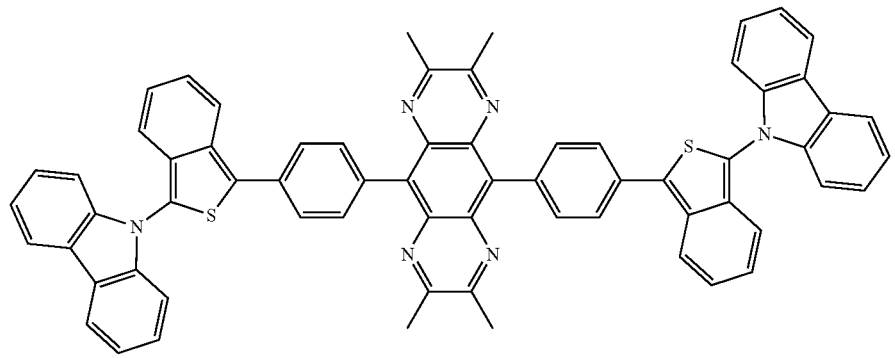
28
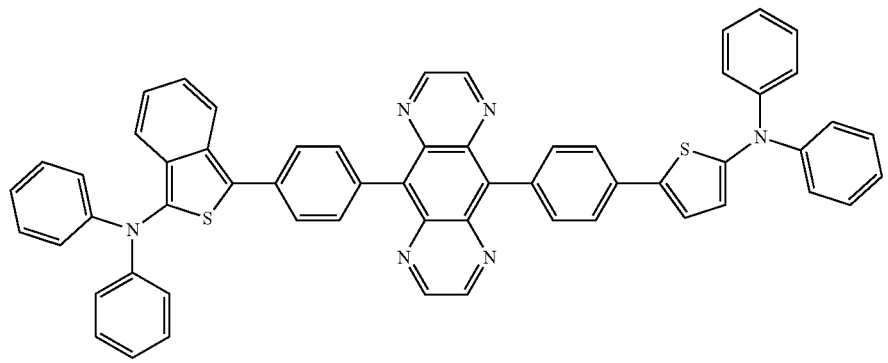
29
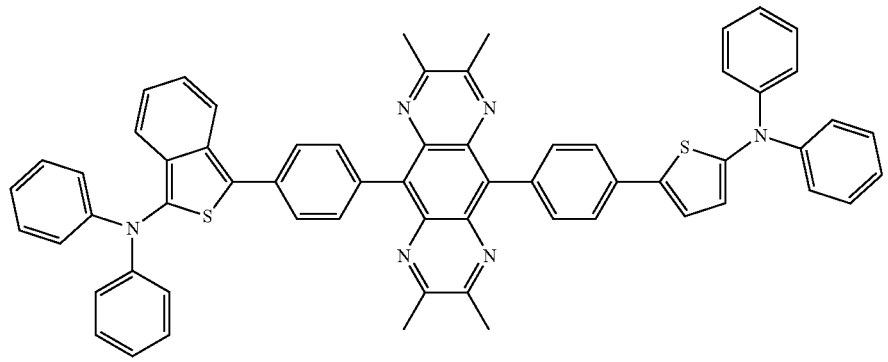
30 31
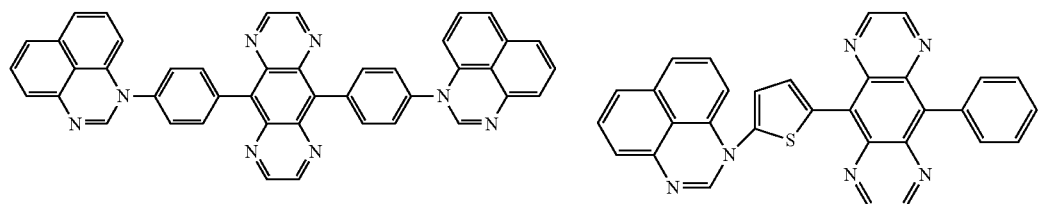
32 33
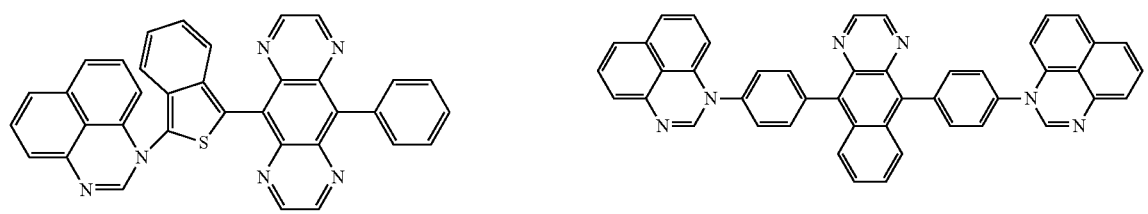

-continued
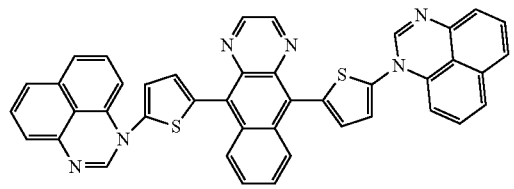
34
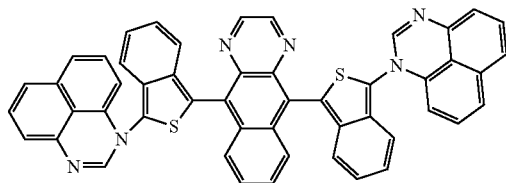
35
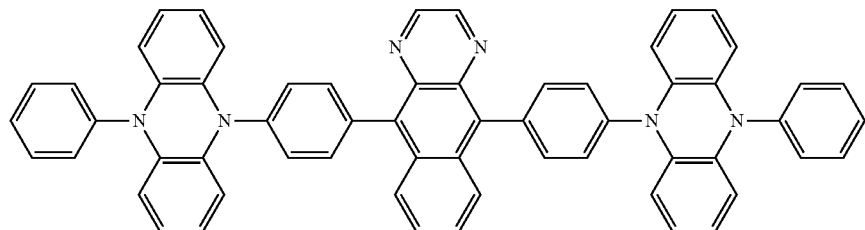
36
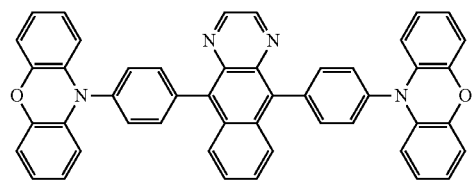
37
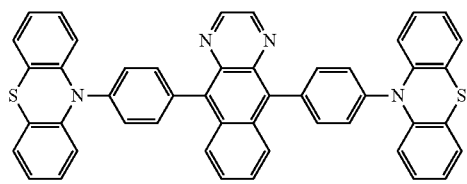
38
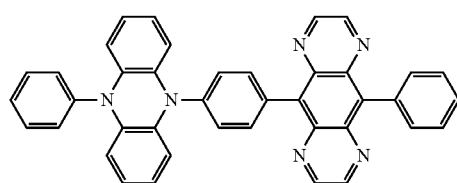
39
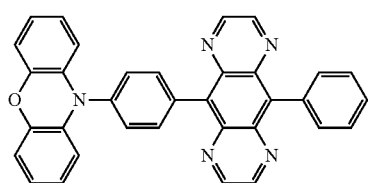
40
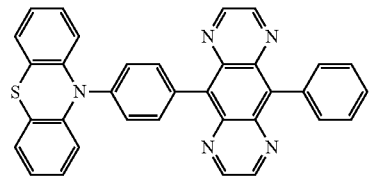
41
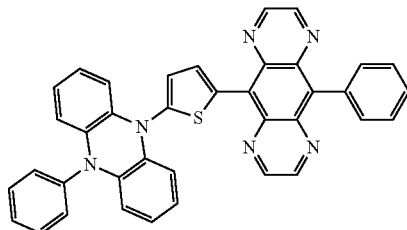
42
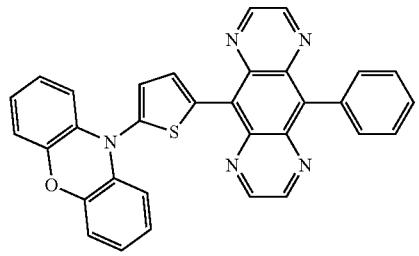
43
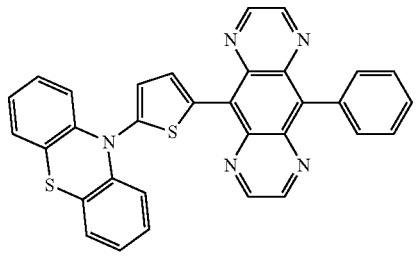
44

-continued
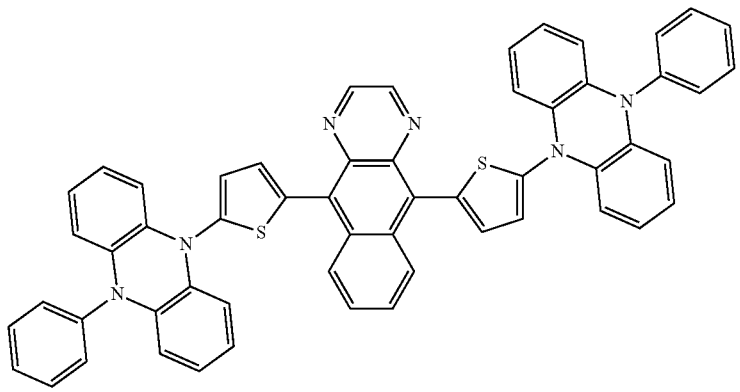
45
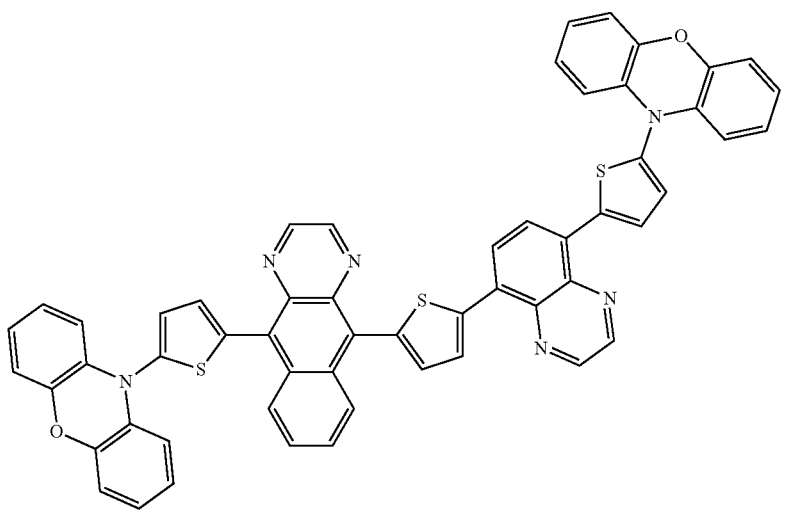
46
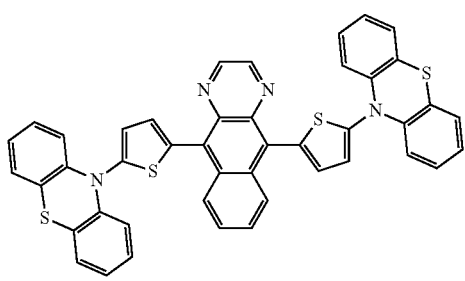
47
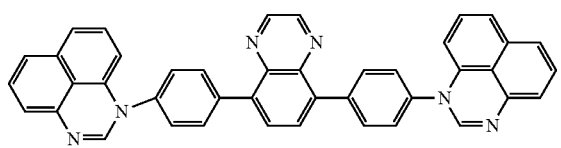
48
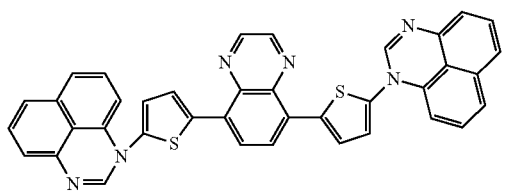
49
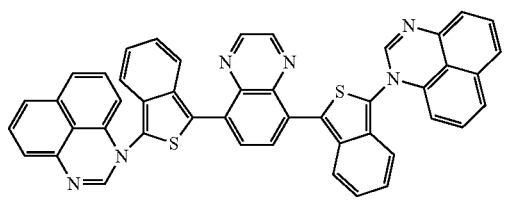
50
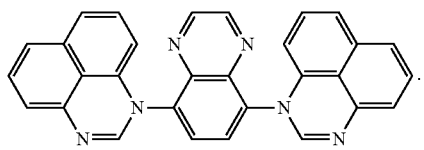
51

11. An organic electroluminescence device, comprising:
a first electrode;
a hole transport region provided on the first electrode;
an emission layer provided on the hole transport region;
an electron transport region provided on the emission layer; and
a second electrode provided on the electron transport region,
wherein the emission layer comprises a heterocyclic compound represented by the following Formula 1:

$$D_1\text{-}A\text{-}D_2 \qquad \text{Formula 1}$$

wherein in Formula 1, A is represented by the following Formula 2, $D_1$ is represented by the following Formula 3, and $D_2$ is represented by the following Formula 4:

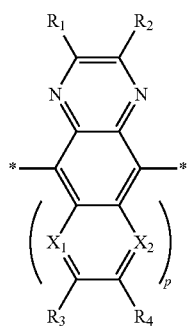

Formula 2

$$Y_1\text{---}(L_1)_q\text{---}* \qquad \text{Formula 3}$$

$$*\text{---}(L_2)_r\text{---}Y_2 \qquad \text{Formula 4}$$

wherein in Formulae 2 to 4,
q and r are each independently an integer of 0 to 3,
p is 0 or 1,
$X_1$ and $X_2$ are each independently CR' or N,
R' and $R_1$ to $R_4$ are each independently a hydrogen atom, a deuterium atom, a substituted or unsubstituted alkyl group having 1 to 10 carbon atoms, or a substituted or unsubstituted aryl group having 6 to 30 carbon atoms for forming a ring,
$L_1$ and $L_2$ are each independently a substituted or unsubstituted arylene group having 6 to 30 carbon atoms for forming a ring, or a substituted or unsubstituted heteroarylene group having 2 to 30 carbon atoms for forming a ring,
$Y_1$ and $Y_2$ are each independently a substituted or unsubstituted arylamine group, a substituted or unsubstituted aryl group having 6 to 30 carbon atoms for forming a ring, or a substituted or unsubstituted heteroaryl group having 2 to 30 carbon atoms for forming a ring, and
at least one of $Y_1$ or $Y_2$ is an electron-donating group,
in case p is 0, $Y_1$ and $Y_2$ are each independently represented by the following Formula 5:

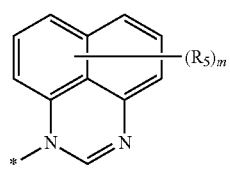

Formula 5 wherein in Formula 5,
$R_5$ is a hydrogen atom, a deuterium atom, a substituted or unsubstituted alkyl group having 1 to 10 carbon atoms, or a substituted or unsubstituted aryl group having 6 to 30 carbon atoms for forming a ring, and
m is an integer of 0 to 6,
wherein the emission layer comprises a host and a dopant and emits near-infrared rays in a wavelength region of about 750 nm to about 1,000 nm, and
wherein the dopant comprises the heterocyclic compound.

12. The organic electroluminescence device of claim 11, wherein p is 1, and $X_1$ and $X_2$ are N.

13. The organic electroluminescence device of claim 11, wherein at least one chosen from $R_1$ to $R_4$ is a substituted or unsubstituted alkyl group having 1 to 10 carbon atoms, or a substituted or unsubstituted aryl group having 6 to 30 carbon atoms for forming a ring.

14. The organic electroluminescence device of claim 11, wherein $D_1$ and $D_2$ are symmetric about A.

15. The organic electroluminescence device of claim 11, wherein the heterocyclic compound represented by Formula 1 is at least one selected from compounds represented in the following Compound Group 1:

Compound Group 1

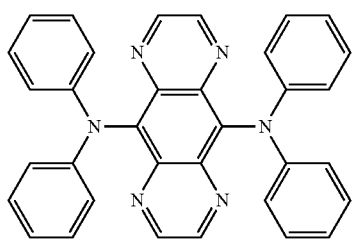

1

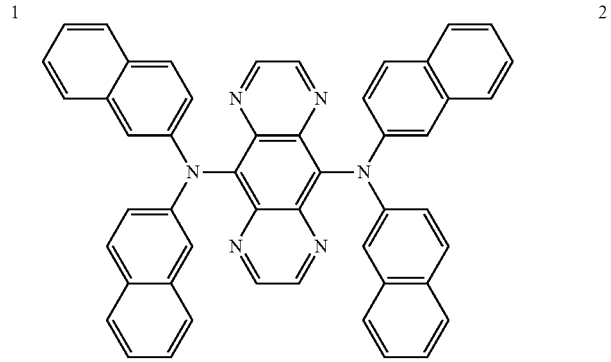

2

-continued
3
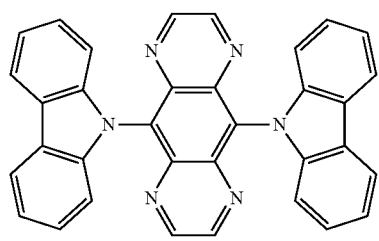
4
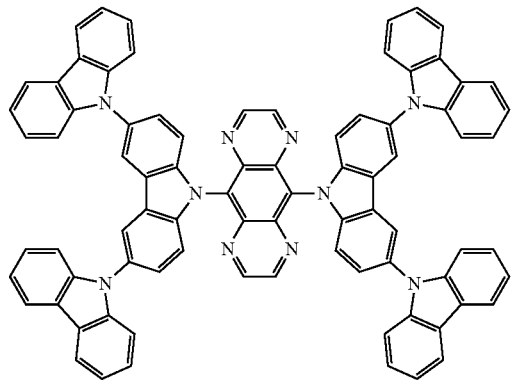
5
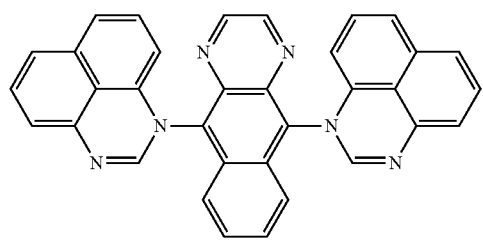
6
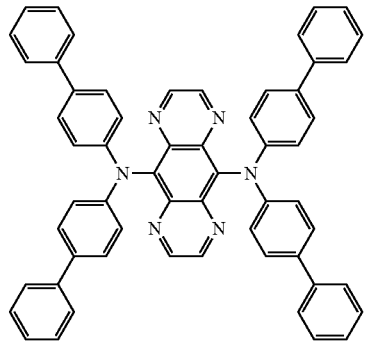
7
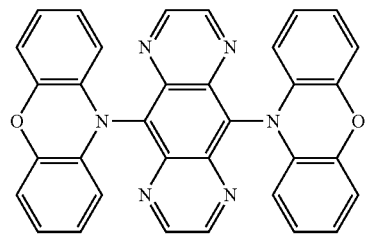
8
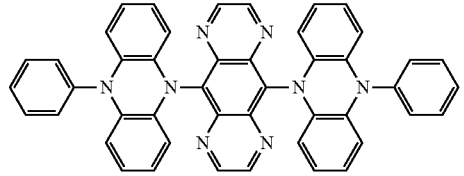
9
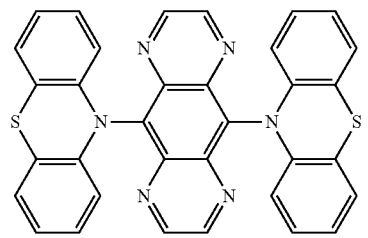
10
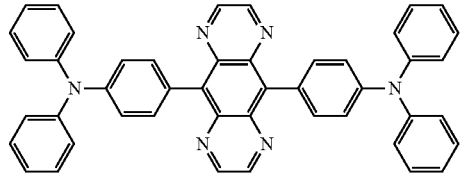
11
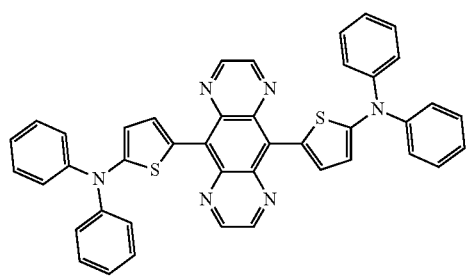
12
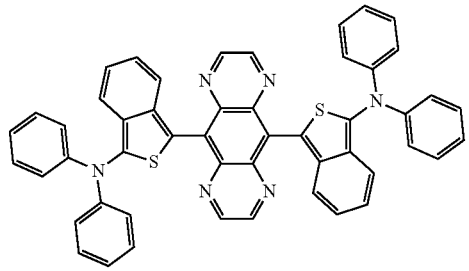

-continued
13
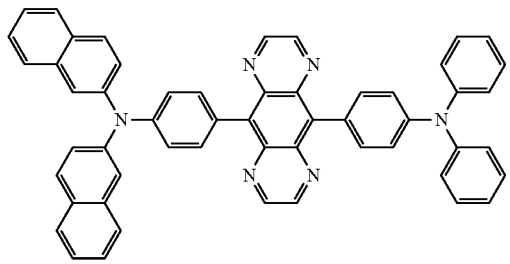
14
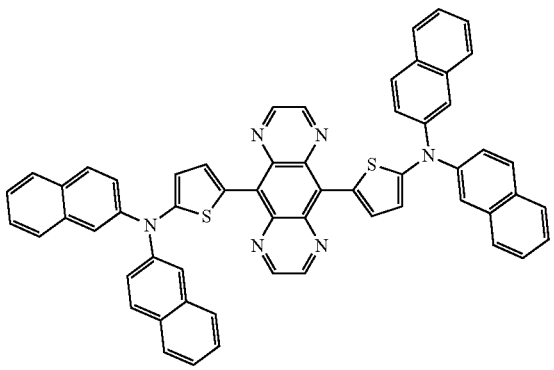
15
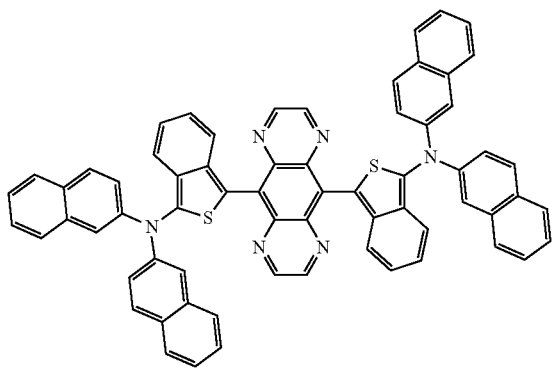
16
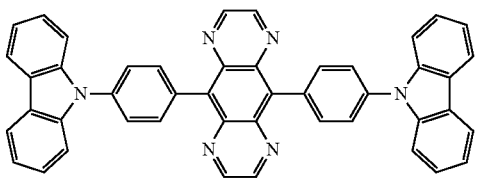
17
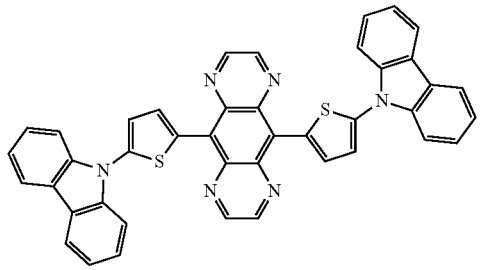
18
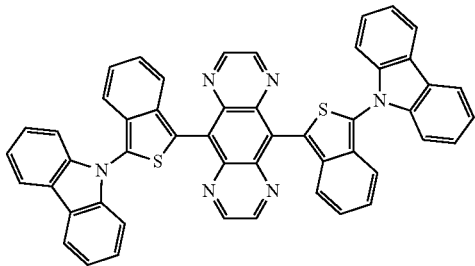
19
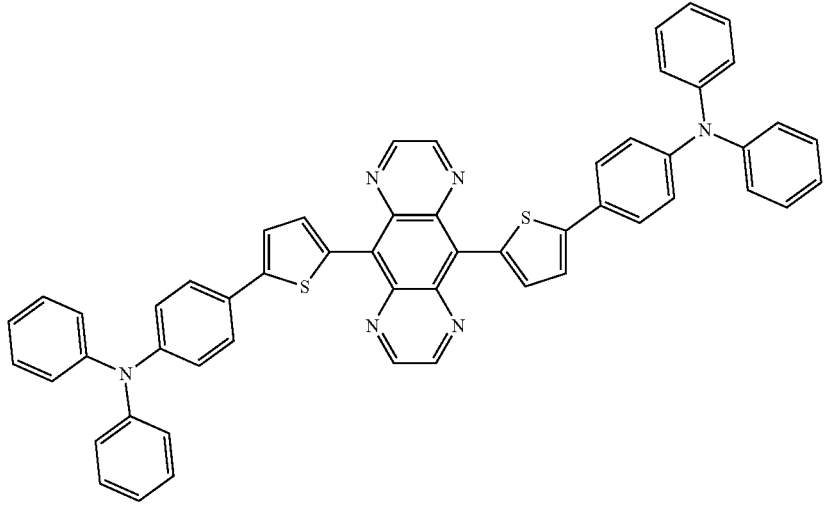

-continued
20
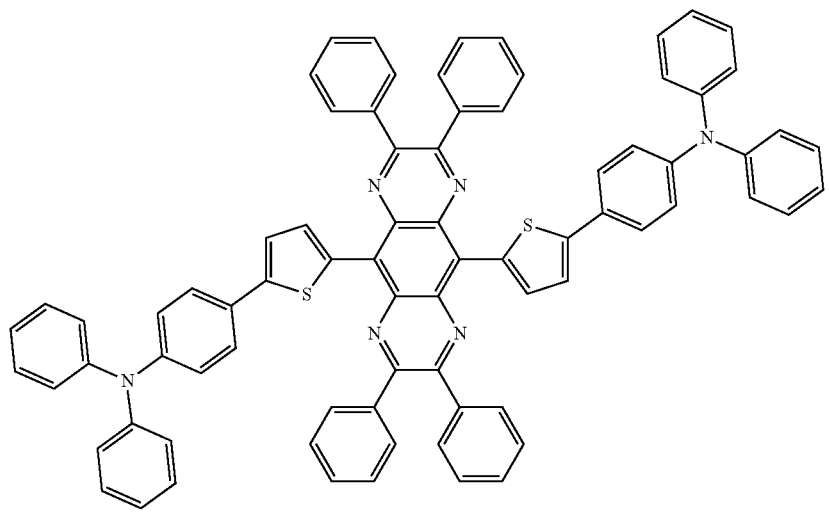
21
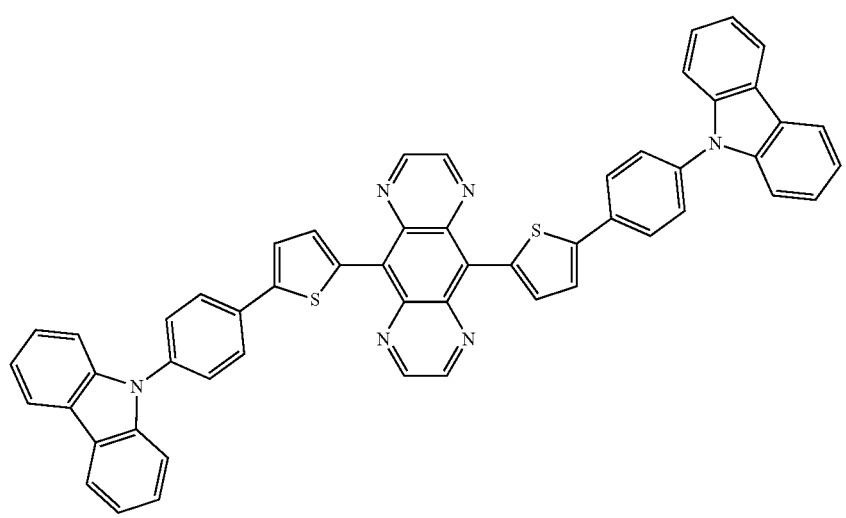
22
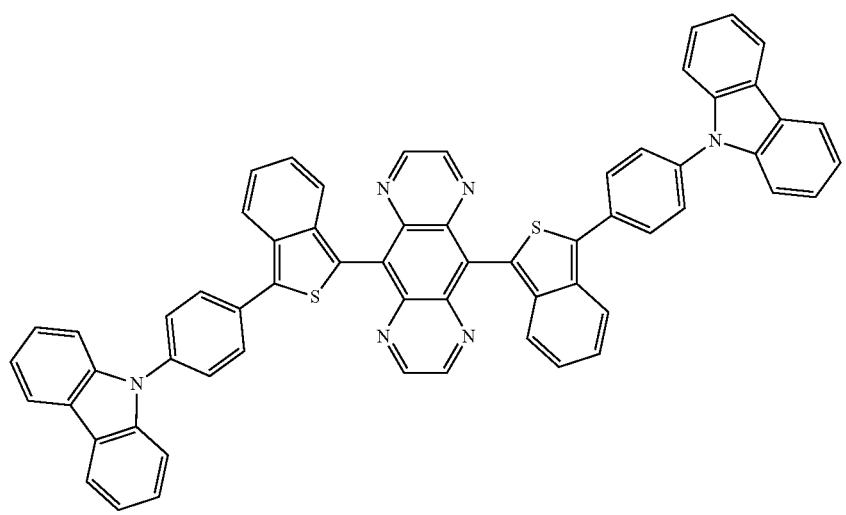

23
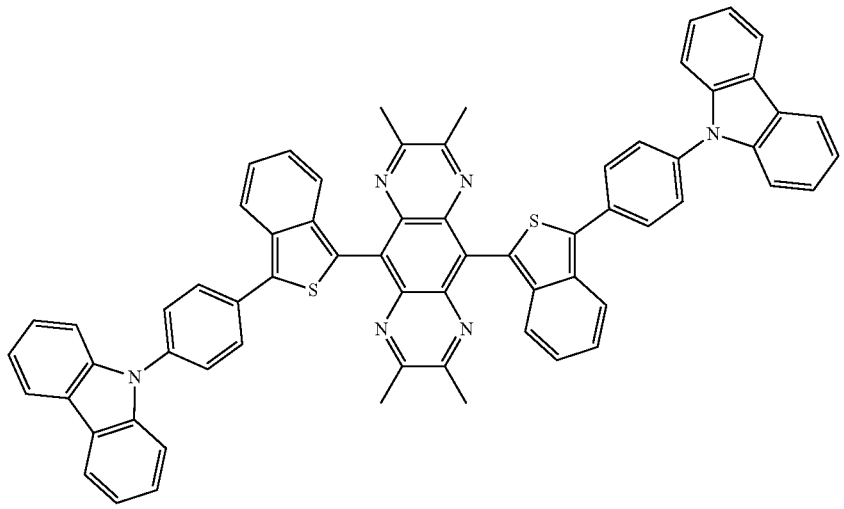
24
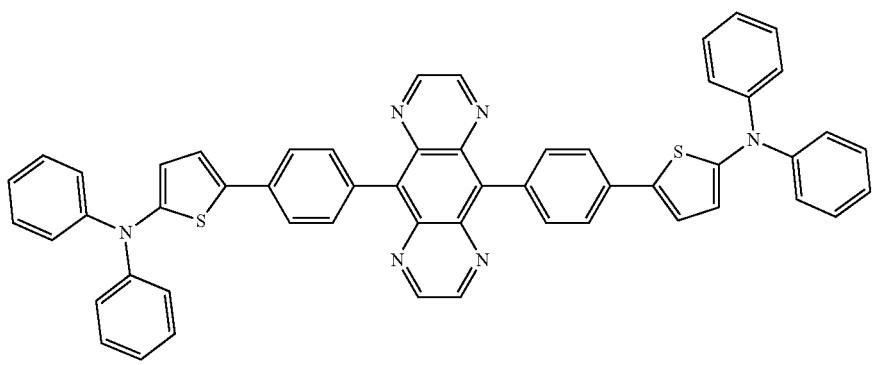
25
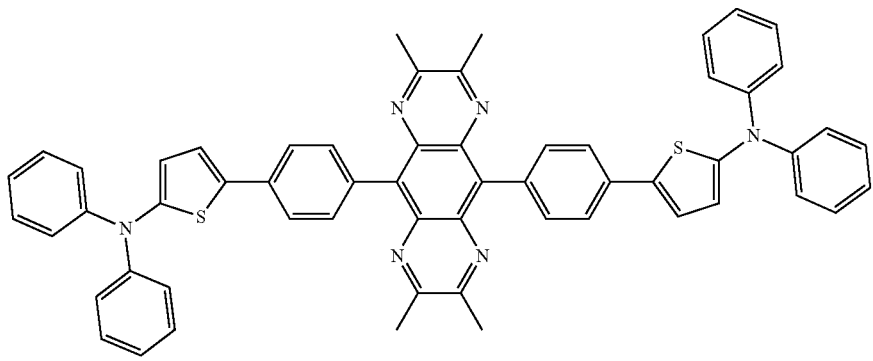
26
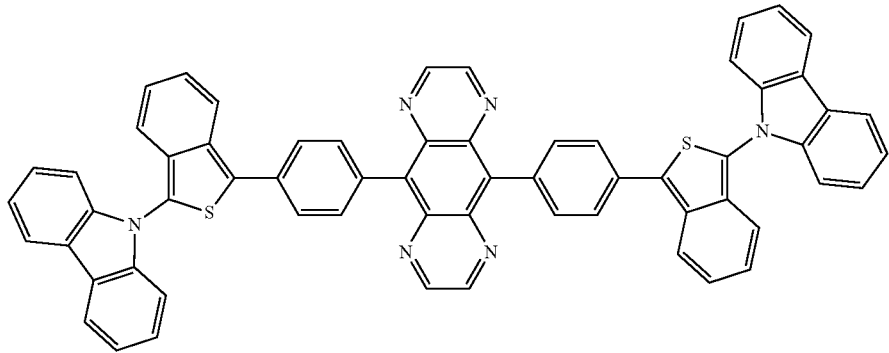

27
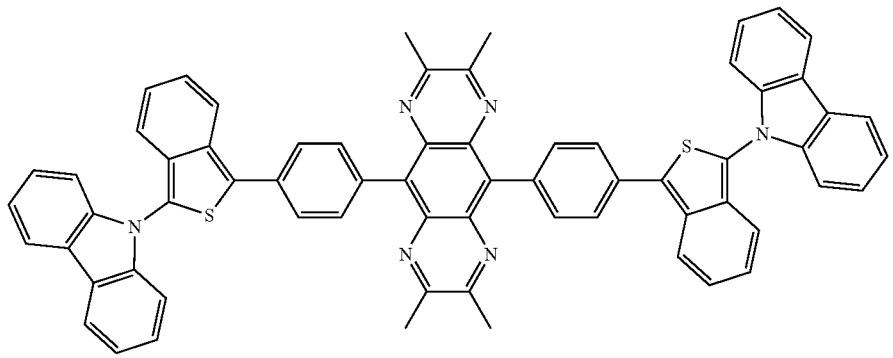
28
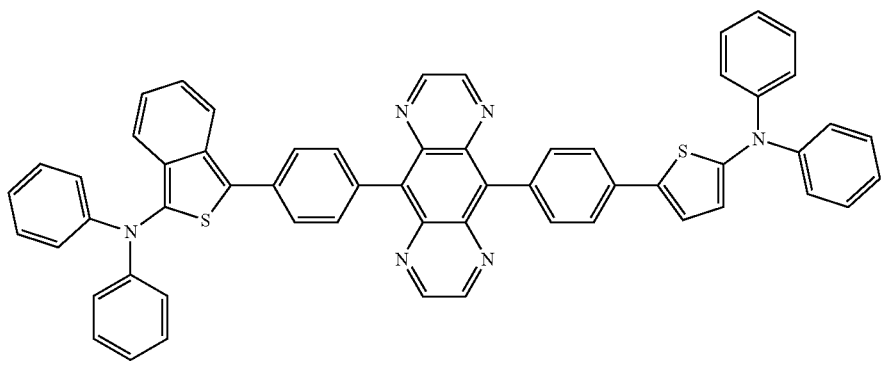
29
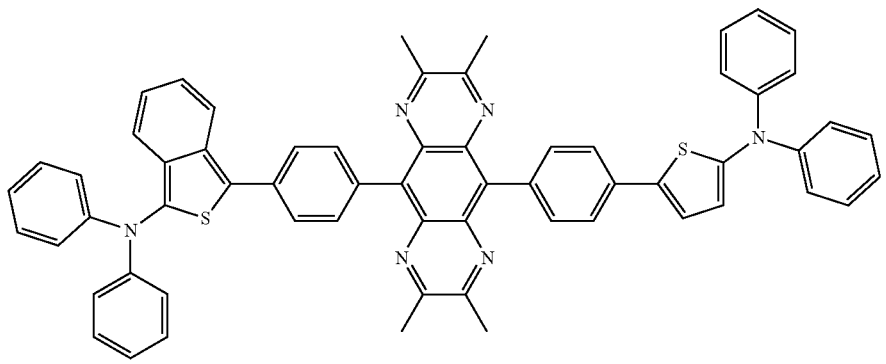
30 31
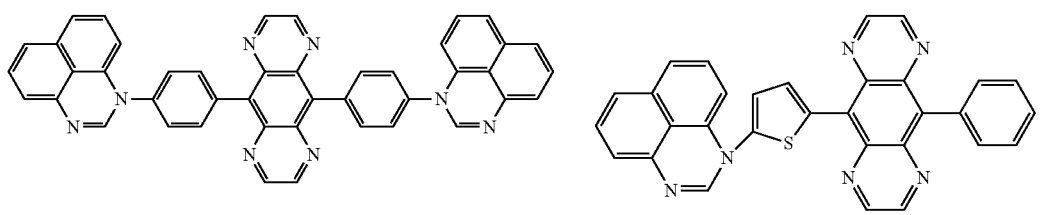
32 33
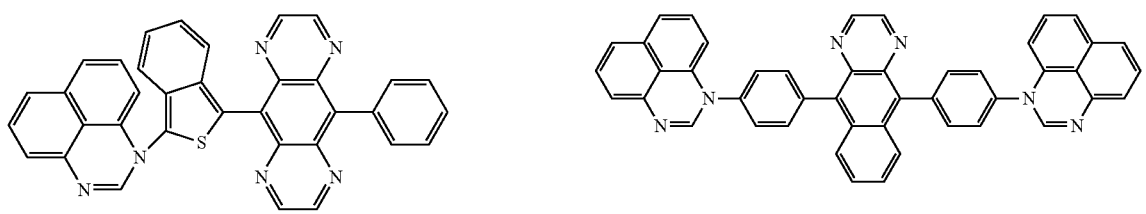

-continued
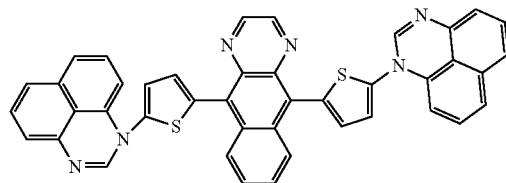
34
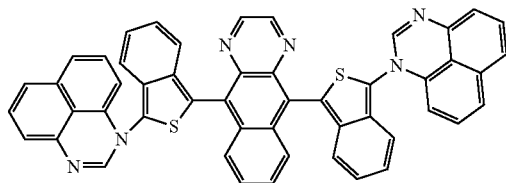
35
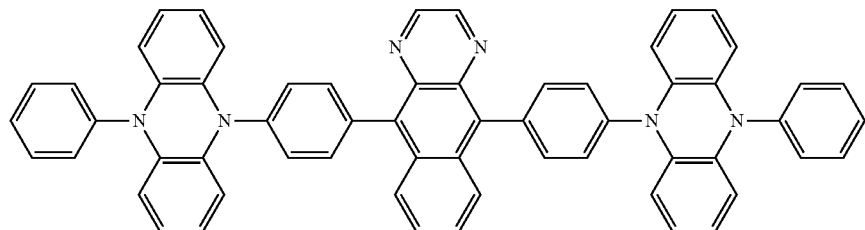
36
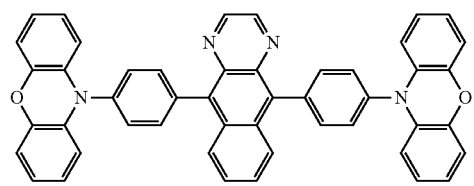
37
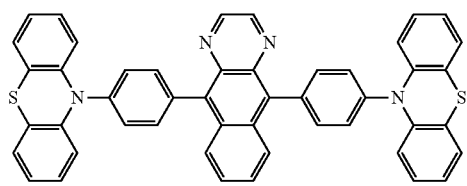
38
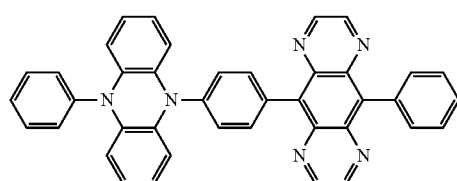
39
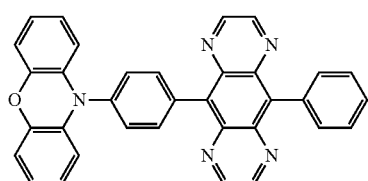
40
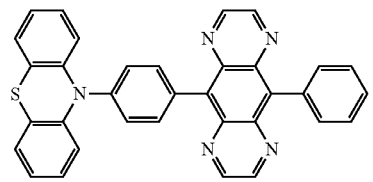
41
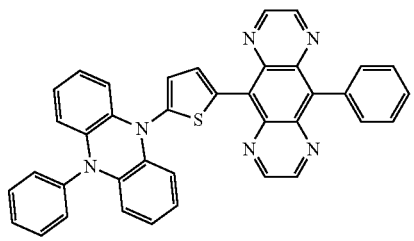
42
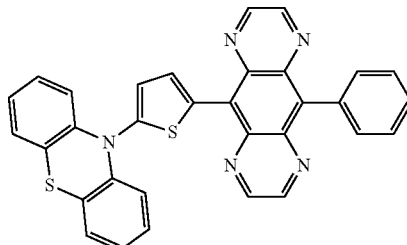
44

45
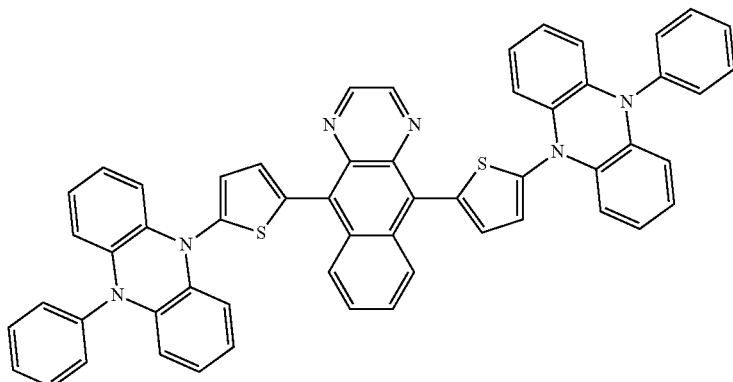
46
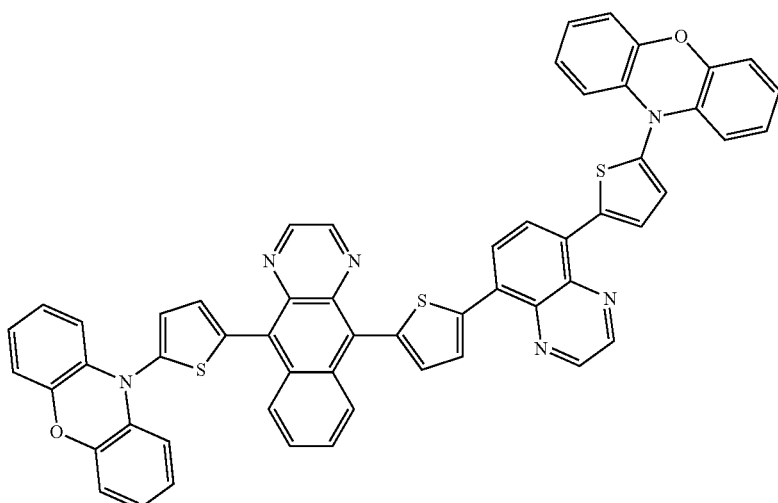
47
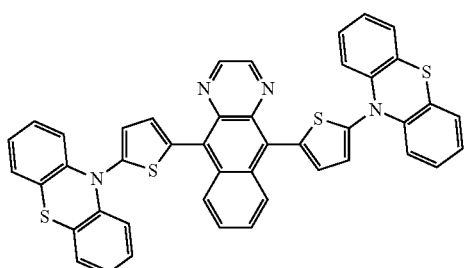
48
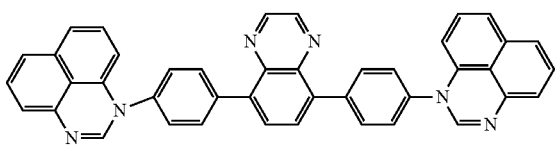
49
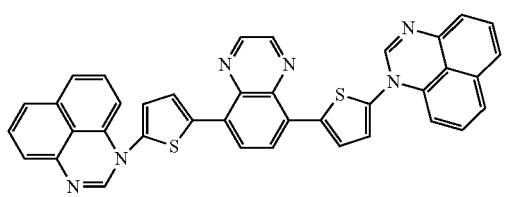
50
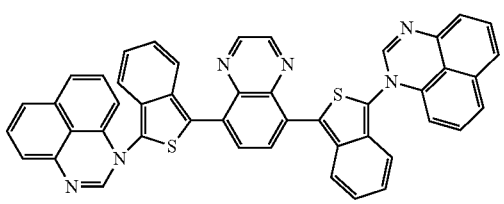
51
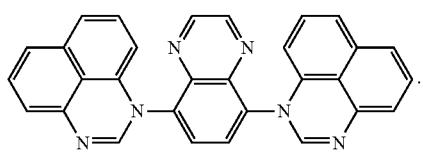
16. An organic electroluminescence display device, comprising:
a first pixel comprising a first organic light emitting diode which emits first visible rays;

a second pixel comprising a second organic light emitting diode which emits second visible rays;
a third pixel comprising a third organic light emitting diode which emits third visible rays; and
a fourth pixel comprising a fourth organic light emitting diode which emits near-infrared rays;
wherein the fourth organic light emitting diode comprises an emission layer comprising a heterocyclic compound represented by the following Formula 1:

$$D_1\text{-}A\text{-}D_2 \qquad \text{Formula 1}$$

wherein in Formula 1, A is represented by the following Formula 2, $D_1$ is represented by the following Formula 3, and $D_2$ is represented by the following Formula 4:

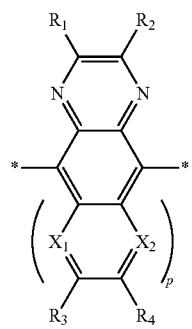

Formula 2

Formula 3

$$Y_1\text{---}(L_1)_q\text{---}*$$

Formula 4

$$*\text{---}(L_2)_r\text{---}Y_2$$

wherein in Formulae 2 to 4,
q and r are each independently an integer of 0 to 3,
p is 0 or 1,
$X_1$ and $X_2$ are each independently CR' or N,
R' and $R_1$ to $R_4$ are each independently a hydrogen atom, a deuterium atom, a substituted or unsubstituted alkyl group having 1 to 10 carbon atoms, or a substituted or unsubstituted aryl group having 6 to 30 carbon atoms for forming a ring, $L_1$ and $L_2$ are each independently a substituted or unsubstituted arylene group having 6 to 30 carbon atoms for forming a ring, or a substituted or unsubstituted heteroarylene group having 2 to 30 carbon atoms for forming a ring, $Y_1$ and $Y_2$ are each independently a substituted or unsubstituted arylamine group, a substituted or unsubstituted aryl group having 6 to 30 carbon atoms for forming a ring, or a substituted or unsubstituted heteroaryl group having 2 to 30 carbon atoms for forming a ring, and at least one of $Y_1$ or $Y_2$ is an electron-donating group, in case p is 0, $Y_1$ and $Y_2$ are each independently represented by the following Formula 5:

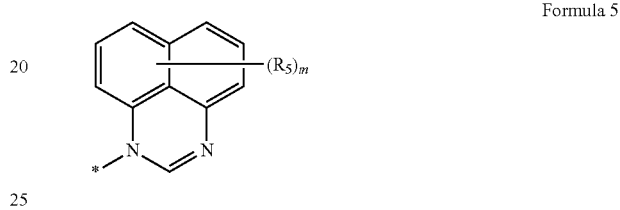

Formula 5 wherein in Formula 5,
$R_5$ is a hydrogen atom, a deuterium atom, a substituted or unsubstituted alkyl group having 1 to 10 carbon atoms, or a substituted or unsubstituted aryl group having 6 to 30 carbon atoms for forming a ring, and
m is an integer of 0 to 6.

17. The organic electroluminescence display device of claim 16, wherein the fourth organic light emitting diode emits near-infrared rays in a wavelength region of about 750 nm to about 1,000 nm.

18. The organic electroluminescence display device of claim 16, wherein $D_1$ and $D_2$ are symmetric about A, p is 1, $X_1$ and $X_2$ are N, and
at least one chosen from $R_1$ to $R_4$ is a substituted or unsubstituted alkyl group having 1 to 10 carbon atoms, or a substituted or unsubstituted aryl group having 6 to 30 carbon atoms for forming a ring.

19. The organic electroluminescence display device of claim 16, wherein the heterocyclic compound represented by Formula 1 is at least one selected from compounds represented in the following Compound Group 1:

Compound Group 1

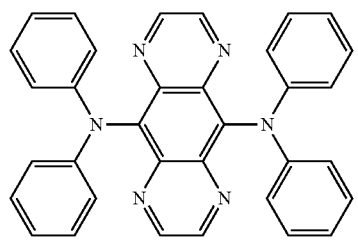

1

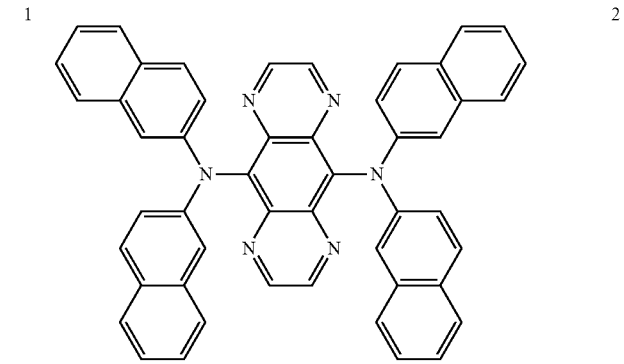

2

-continued
3
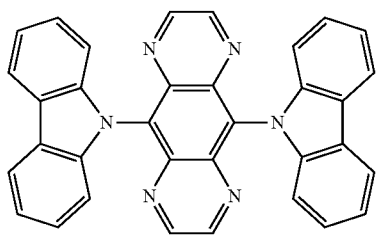
4
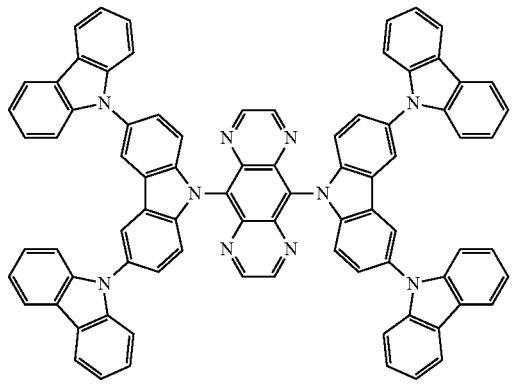
5
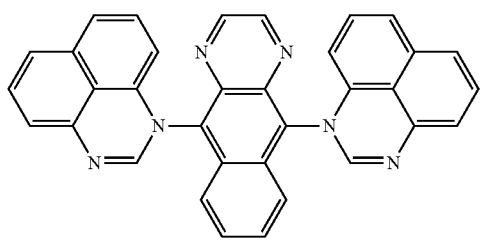
6
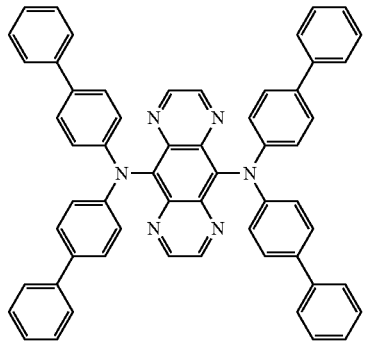
7
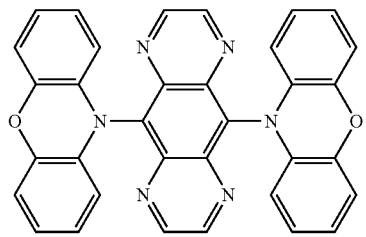
8
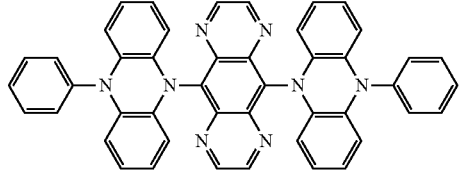
9
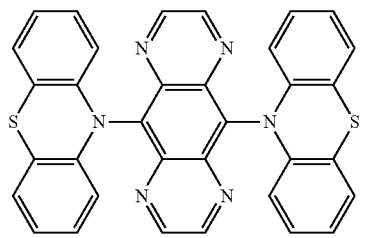
10
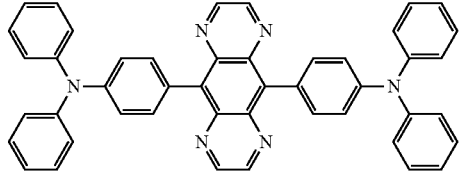
11
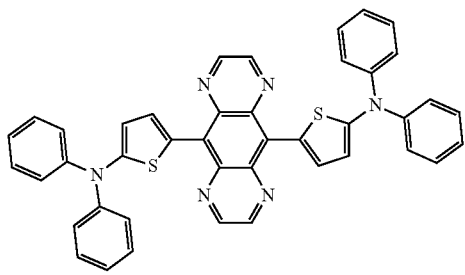
12
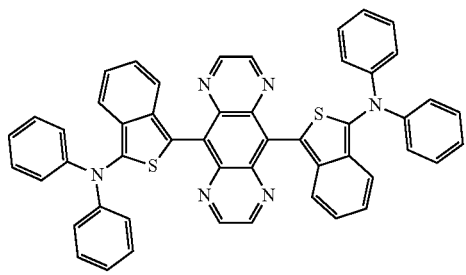

-continued
13
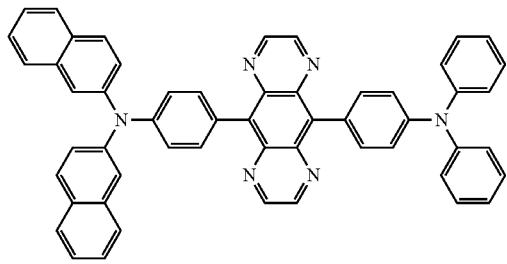
14
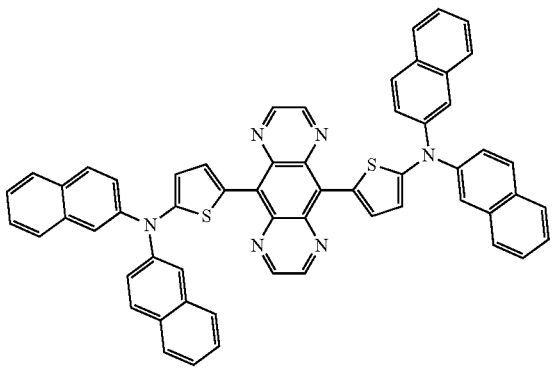
15
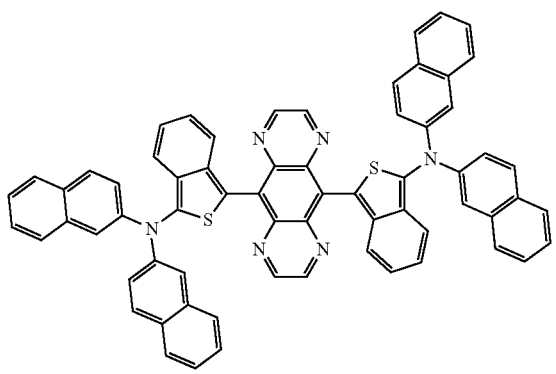
16
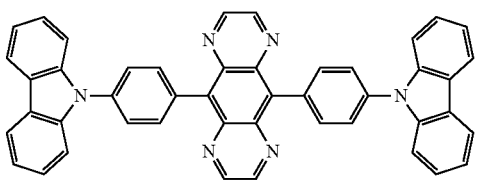
17
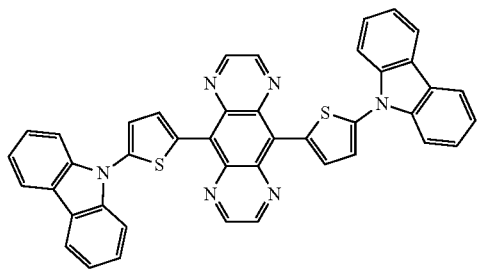
18
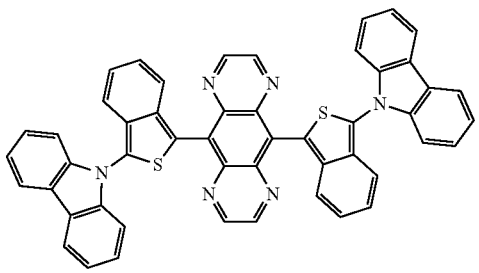
19
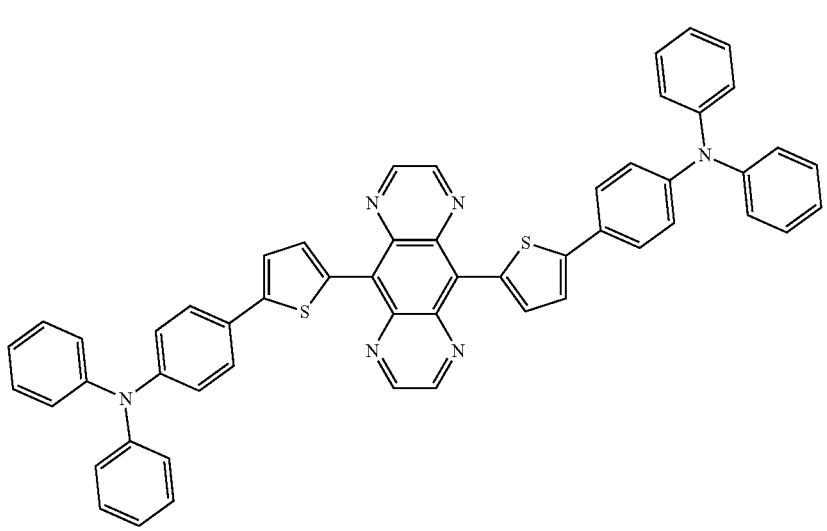

20
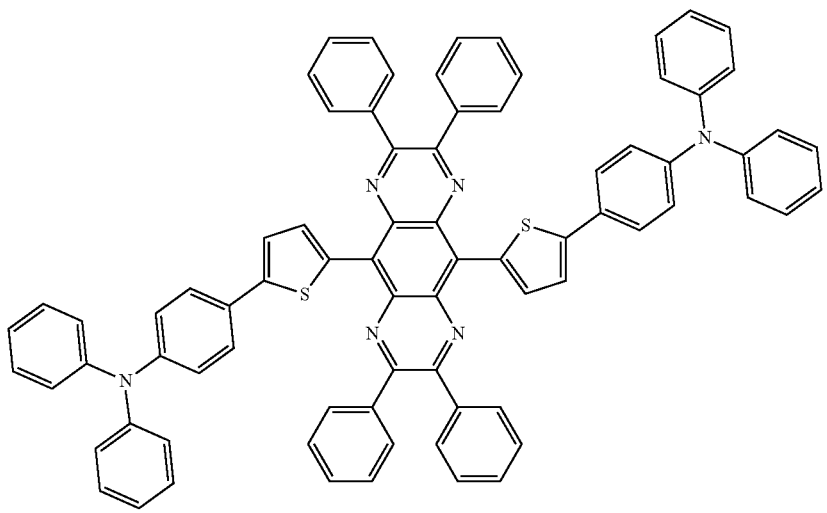
21
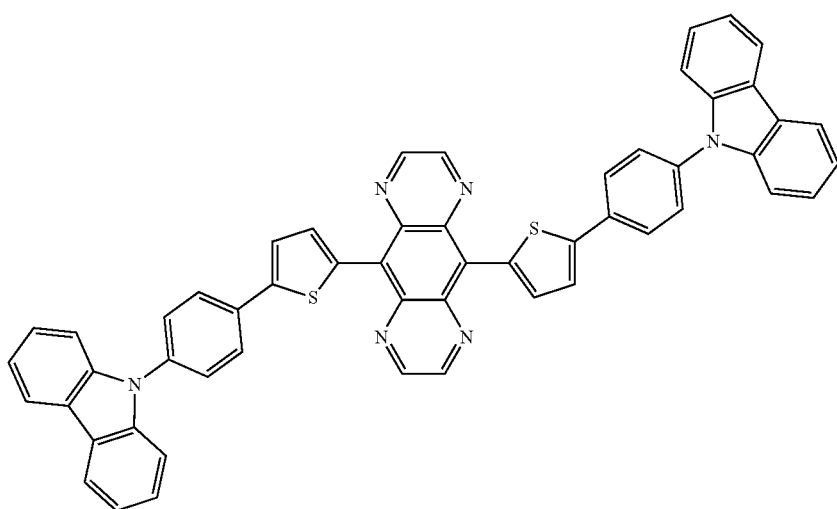
22
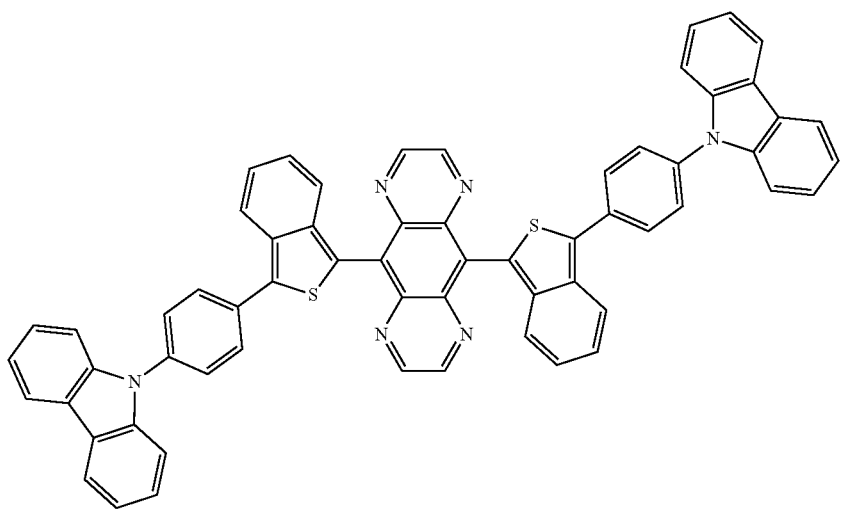

23
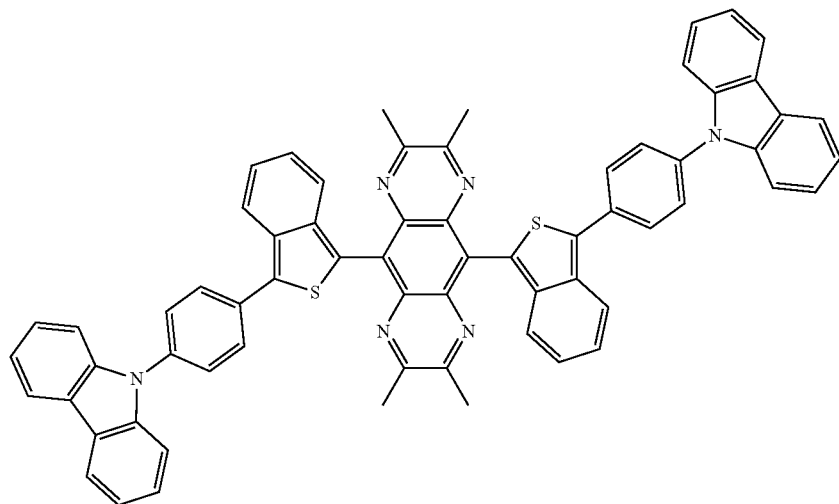
24
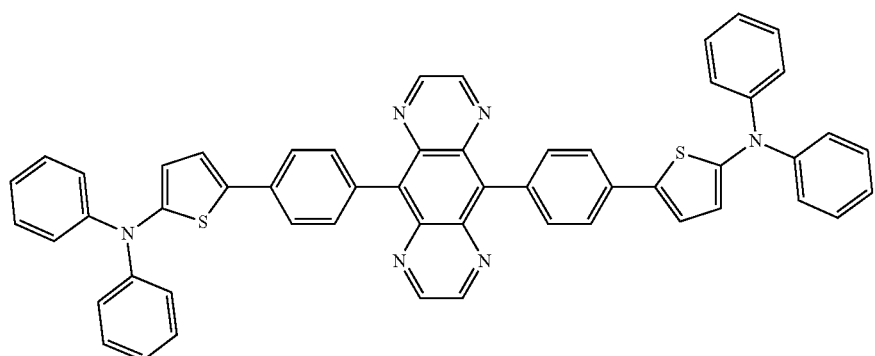
25
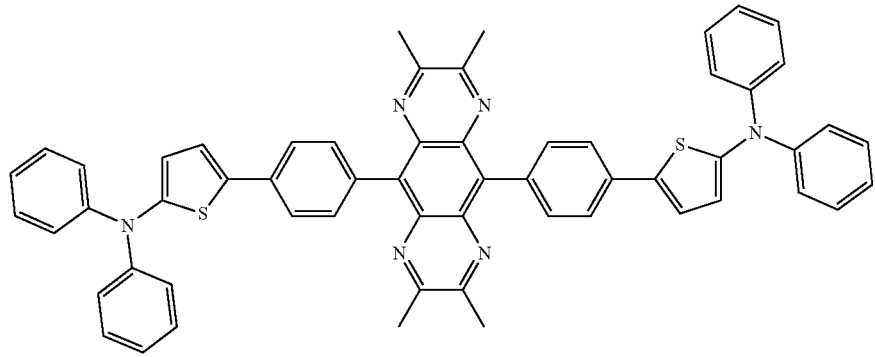
26
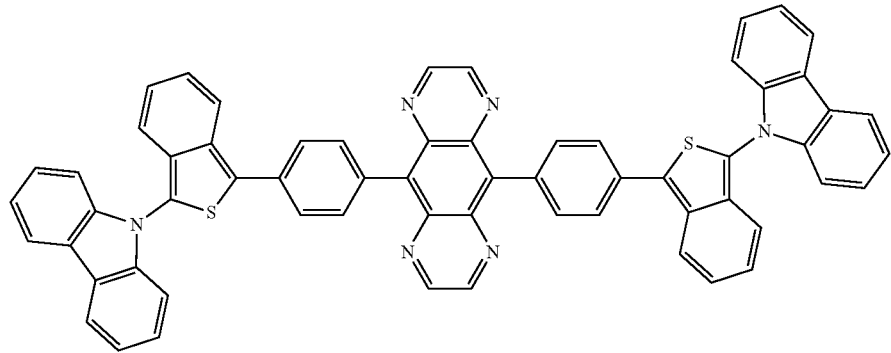

-continued
27
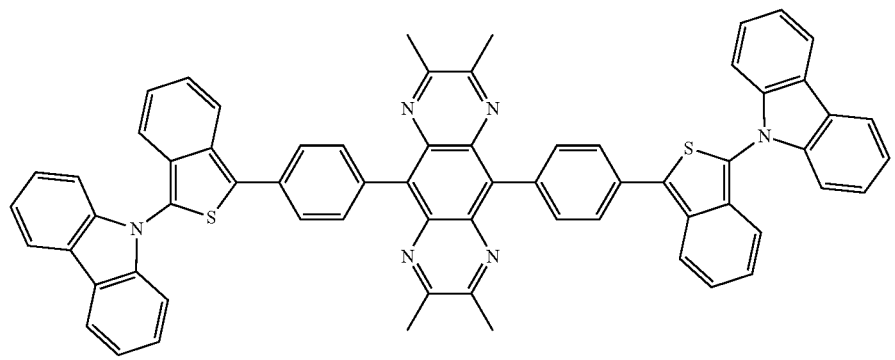
28
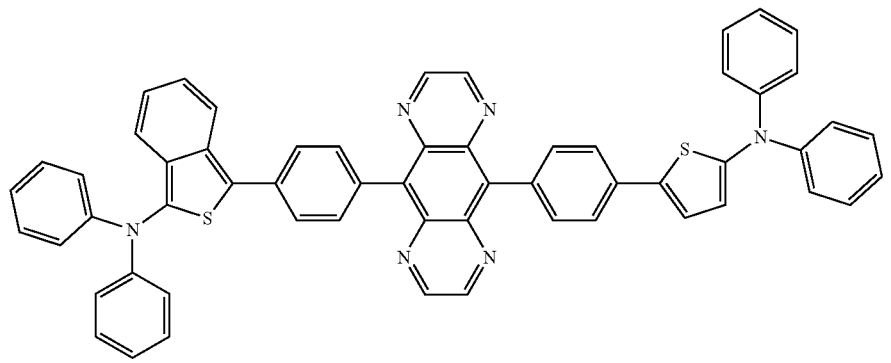
29
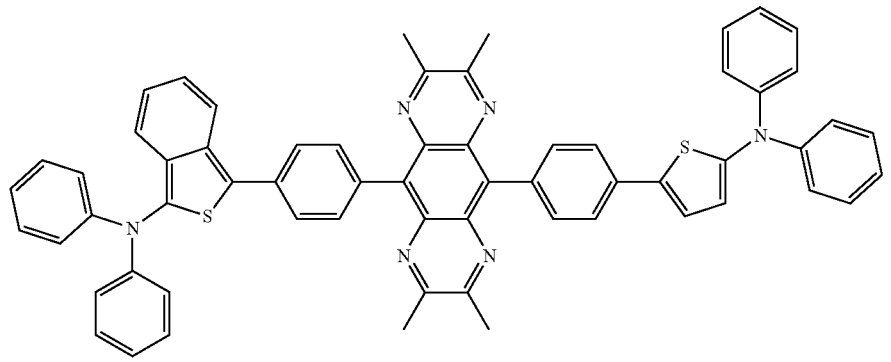
30 31
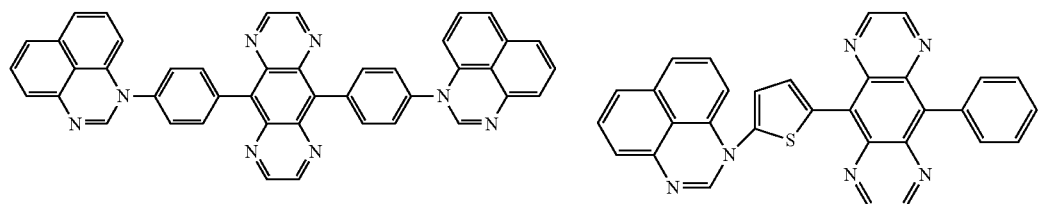
32 33
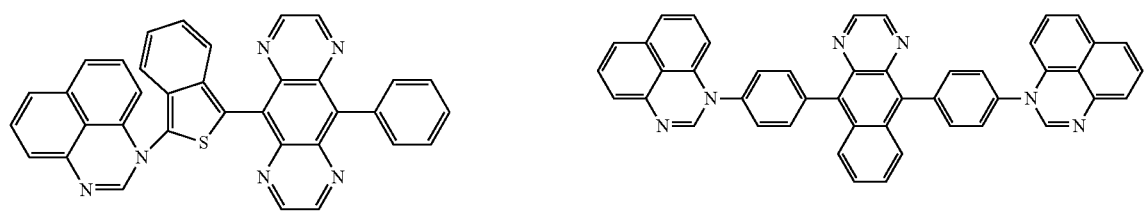

-continued
34
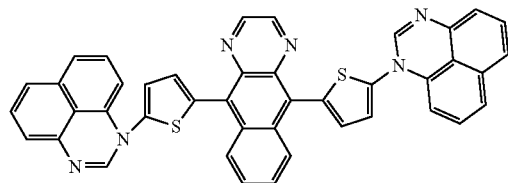
35
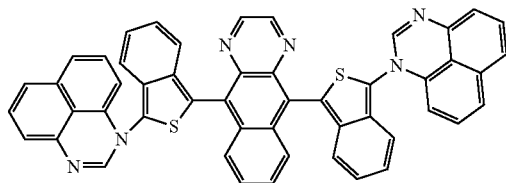
36
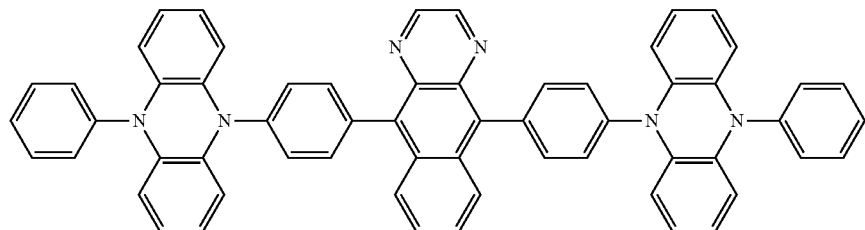
37
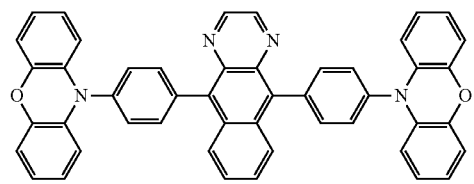
38
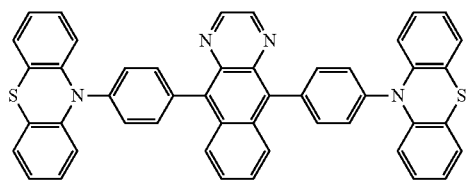
39
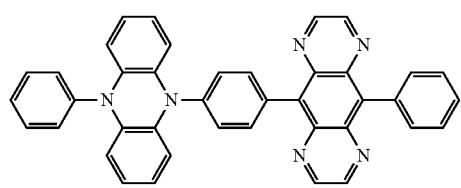
40
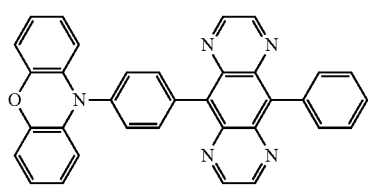
41
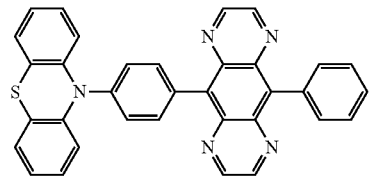
42
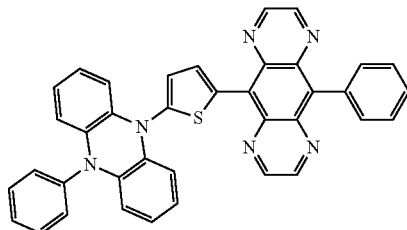
43
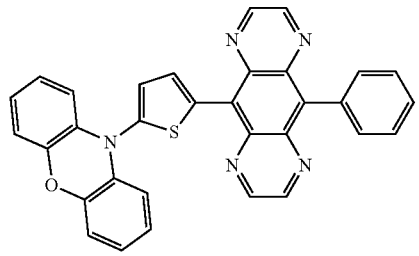
44
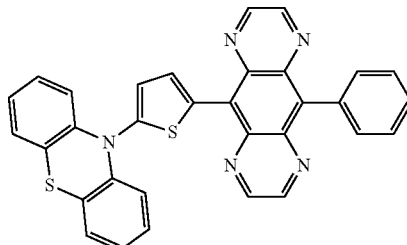

-continued
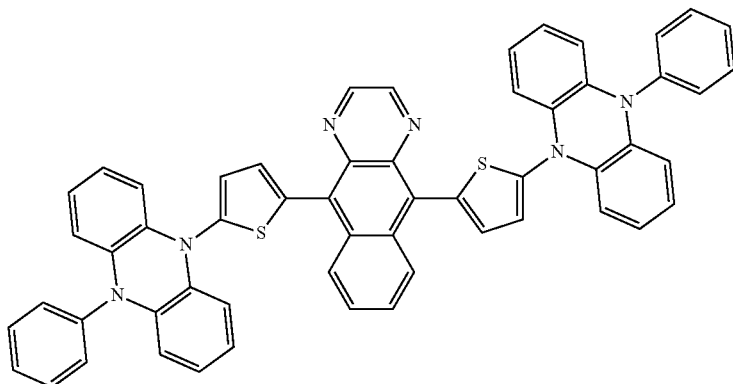
45
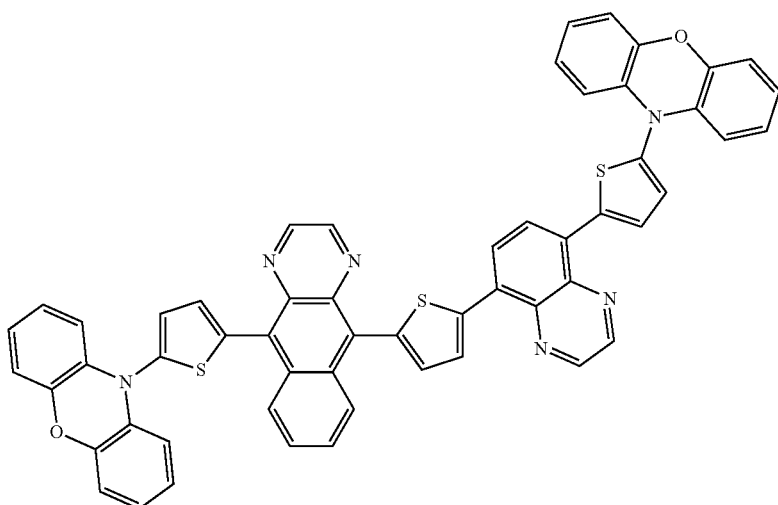
46
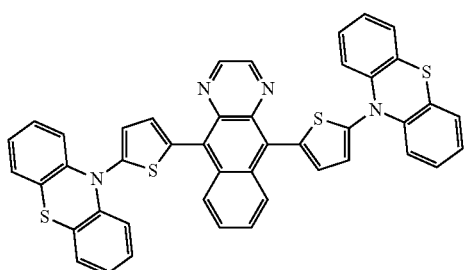
47
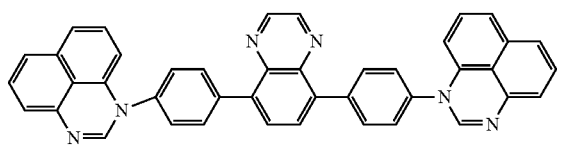
48
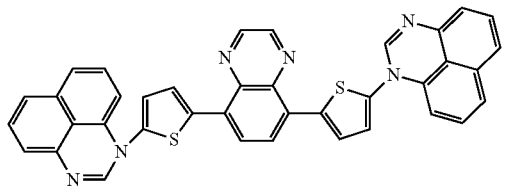
49
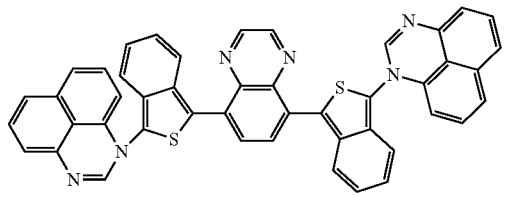
50
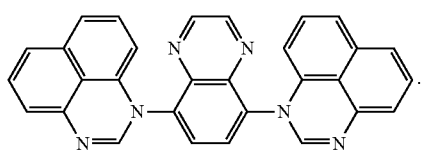
51
* * * * *